US009278920B2

(12) United States Patent
Riedl et al.

(10) Patent No.: US 9,278,920 B2
(45) Date of Patent: Mar. 8, 2016

(54) PLEUROMUTILIN DERIVATIVES FOR USE IN THE TREATMENT OF DISEASES MEDIATED BY MICROBES

(75) Inventors: Rosemarie Riedl, Vienna (AT); Klaus Thirring, Vienna (AT); Werner Heilmayer, Zillingtal (AT)

(73) Assignee: Nabriva Therapeutics AG, Vienna (AT)

( * ) Notice: Subject to any disclaimer, the term of this patent is extended or adjusted under 35 U.S.C. 154(b) by 0 days.

(21) Appl. No.: 13/821,446

(22) PCT Filed: Aug. 11, 2011

(86) PCT No.: PCT/AT2011/000342
§ 371 (c)(1),
(2), (4) Date: Jun. 17, 2013

(87) PCT Pub. No.: WO2012/031307
PCT Pub. Date: Mar. 15, 2012

(65) Prior Publication Data
US 2013/0274329 A1    Oct. 17, 2013

(30) Foreign Application Priority Data

Sep. 9, 2010    (EP) .................................. 10450143

(51) Int. Cl.
| | |
|---|---|
| C07C 323/52 | (2006.01) |
| A61K 31/215 | (2006.01) |
| A61P 31/00 | (2006.01) |
| A61K 31/235 | (2006.01) |
| A61K 45/06 | (2006.01) |

(52) U.S. Cl.
CPC ............. C07C 323/52 (2013.01); A61K 31/235 (2013.01); A61K 45/06 (2013.01); C07C 2101/04 (2013.01); C07C 2101/08 (2013.01); C07C 2101/18 (2013.01); C07C 2102/42 (2013.01); C07C 2102/44 (2013.01); C07C 2103/99 (2013.01)

(58) Field of Classification Search
CPC ............. C07C 323/52; C07C 2101/04; C07C 2101/08; C07C 2101/18; C07C 2102/42; C07C 2102/44; C07C 2103/99; A61K 31/215
USPC ........... 514/511, 530; 560/153, 119, 125, 121
See application file for complete search history.

(56) References Cited

U.S. PATENT DOCUMENTS

| | | | |
|---|---|---|---|
| 8,071,643 B2 * | 12/2011 | Mang et al. .................... | 514/529 |
| 8,088,823 B2 | 1/2012 | Ascher et al. | |
| 8,153,689 B2 * | 4/2012 | Mang et al. .................... | 514/529 |
| 8,222,447 B2 * | 7/2012 | Mang et al. .................... | 560/125 |
| 2005/0215637 A1 | 9/2005 | Ascher et al. | |
| 2012/0046276 A1 | 2/2012 | Ascher et al. | |
| 2014/0256731 A1 * | 9/2014 | Mang et al. ................. | 514/239.5 |

FOREIGN PATENT DOCUMENTS

| | | |
|---|---|---|
| WO | 03/082260 A2 | 10/2003 |
| WO | 2007/014409 A1 | 2/2007 |
| WO | 2008/113089 A1 | 9/2008 |
| WO | 2010/025482 A1 | 3/2010 |

OTHER PUBLICATIONS

International Search Report dated Jul. 11, 2011 issued in International Application No. PCT/AT2011/000342 (2 sheets).
Written Opinion dated Nov. 7, 2011 issued in International Application No. PCT/AT2011/000342 (7 pages).
Berner, H. et al., "Synthese ab-trans-anellierter derivate des tricyclischen diterpens pleuromutilin durch intramolekulare 1,5-hydrid-verschiebung", Tetrahedron, vol. 36, No. 12,1807-1811 (1980).
Clinical and Laboratory Standards Institute (CLSI, formerly NCCLS), "Methods for Antimicrobial Susceptibility Testing of Anaerobic Bacteria; Approved Standard—Sixth Edition", M11-A6, vol. 24, No. 2 (2004).
Clinical and Laboratory Standards Institute (CLSI, formerly NCCLS), "Methods for Dilution Antimicrobial Susceptibility Tests for Bacteria that Grow Aerobically; Approved Standard; Seventh Edition", M7-A7, vol. 6, No. 2 (2006).
International Preliminary Report on Patentability dated Mar. 12, 2013 issued in International Application No. PCT/AT2011/000342 (7 pages).
"The Merck Index—An Encyclopedia of Chemicals, Drugs, and Biologicals", Item 7617, Pleuromutilin, 13th ed., O'Neil, M. et al. eds, 1351 (2001).

\* cited by examiner

*Primary Examiner* — Sreeni Padmanabhan
*Assistant Examiner* — Irina Neagu
(74) *Attorney, Agent, or Firm* — Fitzpatrick, Cella, Harper & Scinto

(57) ABSTRACT

Compounds selected from the group of N-unsubstituted or N-alkylated or N-acylated 14-O-[(amino($C_{0-4}$)alkyl-hydroxy-cycloalkyl- or bicycloalkylsulfanyl)-acetyl]-mutilins which are 14-O-[(amino($C_{0-4}$)alkyl-hydroxy-cyclobutylsulfanyl)-acetyl]-mutilins, 14-O-[(amino($C_{0-4}$)alkyl-hydroxy-cyclopentylsulfanyl)-acetyl]-mutilins, 14-O-[(amino($C_{0-4}$)alkyl-hydroxy-cycloheptylsulfanyl)-acetyl]-mutilins, 14-O-[(amino($C_{0-4}$)alkyl-hydroxy-cyclooctylsulfanyl)-acetyl]-mutilins, or 14-O-[(amino($C_{0-4}$)alkyl-hydroxy-bicycloalkylsulfanyl)-acetyl]-mutilins, optionally in the form of a salt and/or a solvate, a pharmaceutical compositions comprising such compounds and their use as pharmaceuticals, e.g. for the treatment of microbial infections and for the treatment of acne, optionally in combination with other pharmaceutically active agents.

12 Claims, No Drawings

PLEUROMUTILIN DERIVATIVES FOR USE IN THE TREATMENT OF DISEASES MEDIATED BY MICROBES

This application is a National Stage entry of International Application No. PCT/AT2011/000342 filed on Aug. 11, 2011, which claims priority to European Patent Application No. EP 10450143.2, filed on Sep. 9, 2010.

The present invention relates to organic compounds, namely pleuromutilins.

Pleuromutilin, a compound of formula

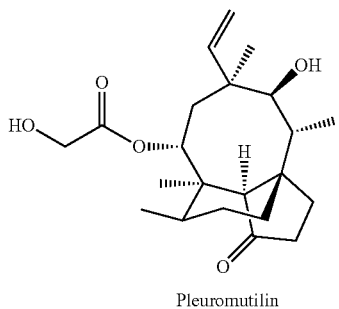 [SMILES: C=C[C@]1(C)C[C@@H](OC(=O)CO)[C@]2(C)C(C)CC[C@]3(CCC(=O)[C@H]32)[C@@H](C)[C@@H]1O]

Pleuromutilin is a naturally occurring antibiotic, e.g. produced by the basidiomycetes *Pleurotus mutilus* and *P. passeckerianus*, see e.g. The Merck Index, 13th edition, item 7617.

A number of further pleuromutilins having the principle ring structure of pleuromutilin and being substituted at the primary hydroxy group have been developed, e.g. as antimicrobials. From WO 2007/014409 pleuromutilin derivatives, e.g. 14-O-[((mono- or dialkylamino)-cycloalkylsulfanyl)-acetyl]-mutilins, from WO 2008/113089 e.g. 14-O-[(amino-hydroxy-cyclohexylsulfanyl)-acetyl]-mutilins and from WO 2010/025482 e.g. N-acylated 14-O-[(amino-hydroxy-cyclohexylsulfanyl)-acetyl]-mutilins are known.

We have now found pleuromutilins with interesting antimicrobial activity.

In one aspect the present invention provides compounds selected from the group of N-unsubstituted, or N-alkylated, or N-acylated 14-O-[(amino($C_{0-4}$)alkyl-hydroxy-cycloalkyl- and bicycloalkylsulfanyl)-acetyl]-mutilins which are 14-O-[(amino($C_{0-4}$)alkyl-hydroxy-cyclobutylsulfanyl)-acetyl]-mutilins, 14-O-[(amino($C_{0-4}$)alkyl-hydroxy-cyclopentylsulfanyl)-acetyl]-mutilins, 14-O-[(amino($C_{0-4}$)alkyl-hydroxy-cycloheptylsulfanyl)-acetyl]-mutilins, 14-O-[(amino($C_{0-4}$)alkyl-hydroxy-cyclooctylsulfanyl)-acetyl]-mutilins, or 14-O-[(amino($C_{0-4}$)alkyl-hydroxy-bicycloalkylsulfanyl)-acetyl]-mutilins.

The term "amino($C_{0-4}$)alkyl-" as used herein means that the amino group is either bound to alkyl of 1 to 4 C-atoms or, in case of $C_0$, directly to the (bi)cycloalkylring In one particular aspect the present invention provides 14-O-[(amino($C_{0-4}$)alkyl-hydroxy-cyclobutylsulfanyl)-acetyl]-mutilins and/or 14-O-[(amino($C_{0-4}$)alkyl-hydroxy-cyclopentylsulfanyl)-acetyl]-mutilins.

In another particular aspect the present invention provides 14-O-[(amino($C_{0-4}$)alkyl-hydroxy-cycloheptylsulfanyl)-acetyl]-mutilins and/or 14-O-[(amino($C_{0-4}$)alkyl-hydroxy-cyclooctylsulfanyl)-acetyl]-mutilins.

In a further particular aspect the present invention provides 14-O-[amino($C_{0-4}$)alkyl-hydroxy-cyclopentylsulfanyl)-acetyl]-mutilins and/or 14-O-[amino($C_{0-4}$)alkyl-hydroxy-bicycloalkylsulfanyl)-acetyl]-mutilins, e.g. 14-O-[amino($C_{0-4}$) alkyl-hydroxy-bicycloalkylsulfanyl)-acetyl]-mutilins wherein one ring of the bicyclic alkyl is a cyclopentyl ring, such as 14-O-[amino($C_{0-4}$)alkyl-hydroxy-bicyclo[3.2.0]heptylsulfanyl)-acetyl]-mutilins and 14-O-[amino($C_{0-4}$)alkyl-hydroxy-octahydropentalenylsulfanyl]-acetyl}-mutilins.

In a further particular aspect the present invention provides 14-O-[(amino($C_{0-4}$)alkyl-hydroxy-bicycloalkylsulfanyl)-acetyl]-mutilins, e.g. 14-O-[(amino($C_{0-4}$)alkyl-hydroxy-bicycloalkylsulfanyl)-acetyl]-mutilins wherein one ring of the bicyclic alkyl is a cyclopentyl ring, such as 14-O-[(amino($C_{0-4}$)alkyl-hydroxy-bicyclo[3.2.0]heptylsulfanyl)-acetyl]-mutilins and 14-O-[(amino($C_{0-4}$)alkyl-hydroxy-octahydropentalenylsulfanyl)-acetyl}-mutilins.

In an amino($C_{0-4}$)alkyl-group as indicated herein alkyl may be not present for the case of $C_0$; or may be $C_1$alkyl; or may be $C_2$alkyl, or may be $C_3$alkyl, or may be $C_4$alkyl.

In another aspect the present invention provides a compound of formula (I)

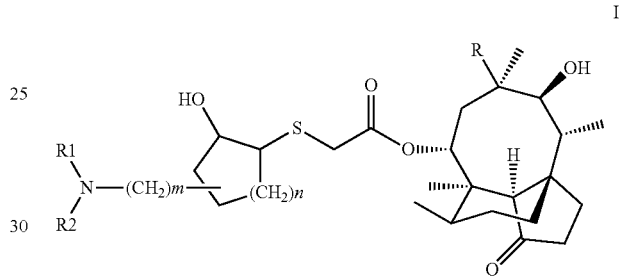

I or of formula (II)

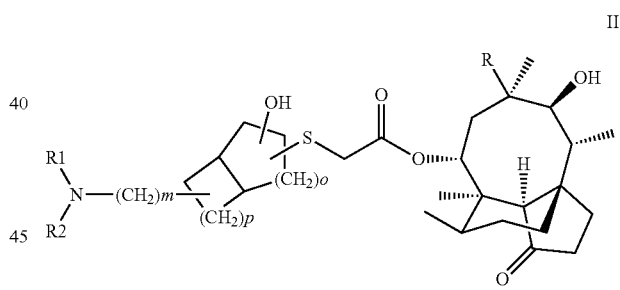

II wherein
m is 0, 1, 2, 3 or 4;
n is 0, 1, 3 or 4;
o is 0, 1, 2, 3 or 4;
p is 0, 1, 2, 3 or 4;
R is ethyl or vinyl;
$R_1$ is hydrogen or ($C_{1-6}$)alkyl,
$R_2$ is hydrogen or
  ($C_{3-6}$)cycloalkyl, or
  unsubstituted ($C_{1-6}$)alkyl, or
  ($C_{1-6}$)alkyl substituted by one or more of
    hydroxy; preferably one or two,
    methoxy,
    halogen,
    ($C_{3-6}$)cycloalkyl, or
$R_1$ and $R_2$ together with the nitrogen atom to which they are attached form a 5 to 7 membered heterocyclic ring containing at least 1 nitrogen atom or 1 nitrogen and 1 additional heteroatom e.g. selected from N or O, or $R_2$ is a group of formula

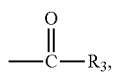

wherein
$R_3$ is hydrogen, straight chain or branched $(C_{1-8})$alkyl or $(C_{3-8})$cycloalkyl, or
$R_3$ is that part of an natural amino acid in D or in L form which remains if the carboxylic acid group is split off, or
$R_3$ is that part of a non natural amino acid in D or in L form which remains if the carboxylic acid group is split off.

Preferred compounds of the present invention are compounds of formula (III)

III

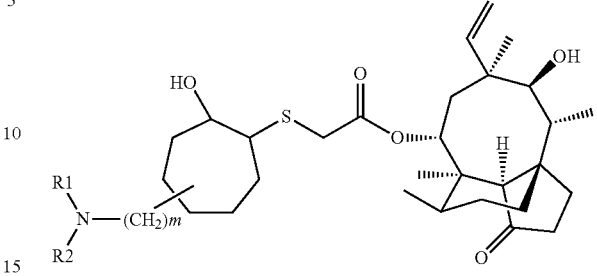

or of formula (IV)

IV

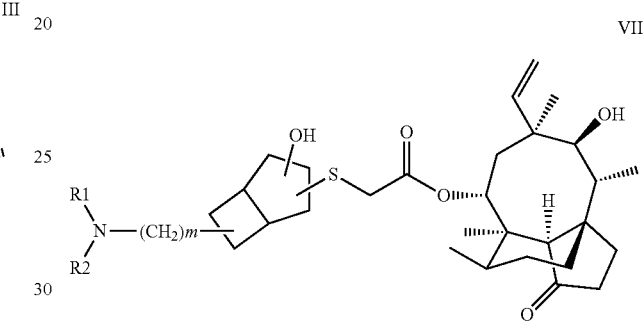

wherein m, n, o, p, $R_1$ and $R_2$ are as defined above, e.g. o is 1; e.g. p is 1 or 2.

More preferred compounds of the present invention are compounds of formula (V)

V

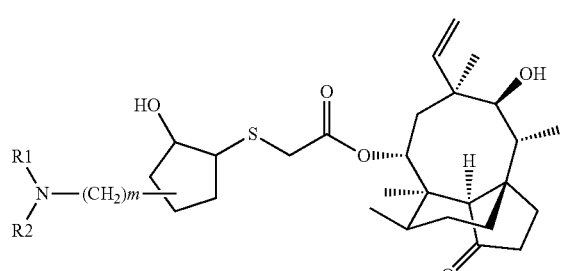

or of formula (VI)

VI

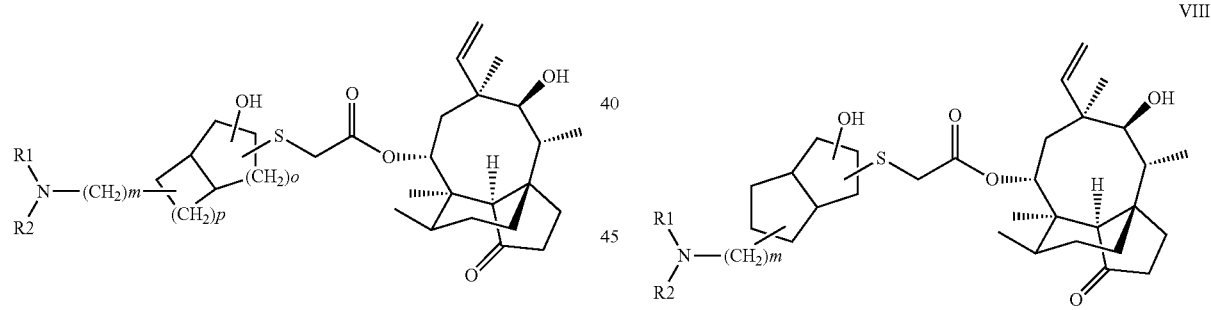

or of formula (VII)

VII or of formula (VIII)

VIII wherein m, $R_1$ and $R_2$ are as defined as defined above.

In another aspect the present invention provides a compound of Examples 1 to 17 below, such as a compound of formula I or II, e.g. a compound selected from the group consisting of 14-O-{[(1R, 2R, 4R)-4-Amino-2-hydroxy-cyclopentylsulfanyl]-acetyl}-mutilin and the (1S, 2S, 4S) diastereomer thereof, 14-O-{[(1R, 2R, 4S)-4-Amino-2-hydroxy-cyclopentylsulfanyl]-acetyl}-mutilin and the (1S, 2S, 4R) diastereomer thereof, 14-O-{[(1R, 2R, 4R)-4-Aminomethyl-2-hydroxy-cyclopentylsulfanyl]-acetyl}-mutilin and the (1S, 2S, 4S) diastereomer thereof, 14-O-{[(1R, 2R, 4S)-4-Aminomethyl-2-hydroxy-cyclopentylsulfanyl]-acetyl}-mutilin and the (1S, 2S, 4R) diastereomer thereof, 14-O-{[(1R, 2R, 4S)-4-[(2,2-Dimethyl-propylamino)-methyl]-2-hydroxy-cyclopentylsulfanyl]-acetyl}-mutilin and the (1S, 2S, 4R) diastereomer thereof, 14-O-{[(1R, 2R, 4S)-2-Hydroxy-4-[(2,2,2-trifluoro-acetylamino)-methyl]-cyclopentylsulfanyl]-acetyl}-mutilin and the (1S, 2S, 4R) diastereomer thereof, 14-O-{[(1R, 2R, 3S)-2-Hydroxy 3-[2-(2,2,2-trifluoro-acetylamino)-ethyl]-cyclopentylsulfanyl]-acetyl}-mutilin and the (1S, 2S, 3R) diastereomer thereof, 14-O-{[(1R, 2R, 3S)-3-(2-Amino-ethyl)-2-hydroxy-cyclopentylsulfanyl]-acetyl}-mutilin and the (1S, 2S, 3R) diastereomer thereof, 14-O-{[(1R, 2R, 5R)-5-Hydroxy-2-[2-(2,2,2-trifluoro-acetylamino)-ethyl]-cyclopentylsulfanyl]-acetyl}-mutilin and the (1S, 2S, 5S) diastereomer thereof, 14-O-{[(1R, 2R, 5R)-2-(2-Amino-ethyl)-5-hydroxy-cyclopentylsulfanyl]-acetyl}-mutilin and the (1S, 2S, 5S) diastereomer thereof, 14-O-{[(1R, 2R, 5R)-2-[2-(2,2-Dimethyl-propylamino)-ethyl]-5-hydroxy-cyclopentylsulfanyl]-acetyl}-mutilin and the (1S, 2S, 5S) diastereomer thereof, 14-O-{[(1R, 2R, 5R)-5-Amino-2-hydroxy-cycloheptylsulfanyl]-acetyl}-mutilin and the (1S, 2S, 5S), (1R, 2R, 5S)-(1S, 2S, 5R) diastereomers thereof, 14-O-{[(1R, 2S, 3S, 5R, 6S)-6-Amino-2-hydroxy-bicyclo[3.2.0]hept-3-ylsulfanyl]-acetyl}-mutilin and the (1S, 2R, 3R, 5S, 6R) diastereomer thereof, 14-O-{[(1R, 2S, 3S, 5R, 6S)-6-Formylamino-2-hydroxy-bicyclo[3.2.0]hept-3-ylsulfanyl]-acetyl}-mutilin and the (1S, 2R, 3R, 5S, 6R) diastereomer thereof, 14-O-{[(1R, 2S, 3S, 5R, 6S)-6-(2-Amino-acetylamino)-2-hydroxy-bicyclo[3.2.0]hept-3-ylsulfanyl]-acetyl}-mutilin and the (1S, 2R, 3R, 5S, 6R) diastereomer thereof, 14-O-{[(1R, 2S, 3S, 5R, 6S)-6-Cyclopropylamino-2-hydroxy-bicyclo[3.2.0]hept-3-ylsulfanyl]-acetyl}-mutilin and the (1S, 2R, 3R, 5S, 6R) diastereomer thereof, and 14-O-{[4-Acetylamino-6a-hydroxy-octahydropentalen-1-ylsulfanyl]-acetyl}-mutilin.

A compound provided by the present invention is herein also designated as "compound(s) of (according to) the present invention". A compound of the present invention includes a compound in any form, e.g. in free form, in the form of a salt, in the form of a solvate and in the form of a salt and a solvate.

According to another aspect, the present invention provides a compound of the present invention in the form of a salt, e.g. and/or solvate.

A salt of a compound of the present invention includes preferably pharmaceutically acceptable salts, although pharmaceutically unacceptable salts are included, e.g. for preparation/isolation/purification purposes.

A salt of a compound of the present invention includes a base salt or an acid addition salt. Pharmaceutically acceptable acid addition salts include salts of a compound of the present invention with an acid, e.g. hydrogen fumaric acid, fumaric acid, hydrogen tartaric acid, tartaric acid, hydrogen ethane-1,2-disulfonic acid, ethane-1,2-disulfonic acid, hydrogen maleic acid, maleic acid, hydrogen naphthalin-1,5-disulfonic acid, hydrogen naphthalin-1,5-disulfonic acid, acetic acid, hydrogen malic acid, malic acid, lactic acid, hydrogen succinic acid, succinic acid, salicylic acid, hydrogen azelaic acid, azelaic acid, 2-[(2,6-dichlorophenyl)-amino]-benzene acetic acid, hydrogen sulfuric acid, sulfuric acid, dihydrogen phosphoric acid, hydrogen phosphoric acid, phosphoric acid, dihydrogen citric acid, hydrogen citric acid, citric acid, deuterochloric acid, hydrochloric acid, preferably hydrochloric acid.

A compound of the present invention in free form may be converted into a corresponding form of a salt, and vice versa. A compound of the present invention in free form or in the form of a salt and in the form of a solvate may be converted into a corresponding compound in free form or in the form of a salt in non-solvated form, and vice versa.

A compound of the present invention may exist in the form of isomers and mixtures thereof, e.g. optical isomers, diastereoisomers, cis/trans conformers. A compound of the present invention may e.g. contain asymmetric carbon atoms and may thus exist in the form of enantiomers or diastereoisomers and mixtures thereof, e.g. racemates or diastereomeric mixtures. Any asymmetric carbon atom may be present in the (R)-, (S)- or (R,S)-configuration, preferably in the (R)- or (S)-configuration.

For example, in a compound of formula I or II the carbon atom of the cycloalkyl ring which is attached to S group, the carbon atom of the cycloalkyl ring which is attached to the OH group, and the carbon atom of the cycloalkyl ring to which the $(CH_2)_m N(R_1R_2)$ group is attached, are all asymmetric carbon atoms. Substituents attached to such asymmetric carbon atoms may thus exist in (R) and (S) configuration, including mixtures thereof. For example, if in a compound of formula I or II $R_2$ is substituted alkyl and that substituent is attached to a carbon atom of the side chain of such alkyl, the carbon atom to which such substituent is attached is an asymmetric carbon atom and such substituent may be in the (R)- and (S)-configuration, including mixtures thereof.

The configuration of asymmetric carbon atoms of the mutilin-tricyclus is preferably the same as in natural pleuromutilin.

Isomeric mixtures may be separated as appropriate, e.g. according, e.g. analogously, to a method as conventional, to obtain pure isomers. The present invention includes a compound of the present invention in any isomeric form and in any isomeric mixture. The present invention also includes tautomers of a compound of the present invention, where tautomers can exist.

Any compound provided according to the present invention may be obtained as appropriate, e.g. according to, e.g. analogously to a method as conventional or as described herein.

E.g. a compound of the present invention may be obtained by reacting a compound PLEU-Tos as defined below with an appropriate amino($C_{0-4}$)alkyl-hydroxy-mercapto-cyclobutane, amino($C_{0-4}$)alkyl-hydroxy-mercapto-cyclopentane, amino($C_{0-4}$)alkyl-hydroxy-mercapto-cycloheptane, amino($C_{0-4}$)alkyl-hydroxy-mercapto-cyclooctane or amino($C_{0-4}$)alkyl-hydroxy-mercapto-bicycloalkane, wherein the amine group is protected, e.g. by Boc, in organic solvent, e.g. polar organic solvent, such as acetonitrile, in the presence of a base and/or coupling agent, such as e.g. DBN; and deprotecting the amine, group, e.g. by treatment with an acid, e.g. HCl. The deprotected amine group can be optionally acylated by reaction with a carboxylic acid, e.g. an amino acid, in the presence of a coupling reagent, or with activated carboxylic acid or carboxylic acid derivative, such as an anhydride of the carboxylic acid or carboxylic acid halogenide. The deprotected amine group from above can be optionally alkylated, e.g. by reductive amination or via an alkylating agent.

An amino($C_{0-4}$)alkyl-hydroxy-mercapto-cyclobutane, amino($C_{0-4}$)alkyl-hydroxy-mercapto-cyclopentane, amino ($C_{0-4}$)alkyl-hydroxy-mercapto-cycloheptane amino($C_{0-4}$) alkyl-hydroxy-mercapto-cyclooctane, or amino($C_{0-4}$)alkyl-hydroxy-mercapto-bicycloalkane, wherein the amine group is protected may be obtained from an N-protected amino ($C_{0-4}$)alkyl-cyclobutene, N-protected amino($C_{0-4}$)alkyl-cyclopentene, N-protected amino($C_{0-4}$)alkyl-cycloheptene, N-protected amino($C_{0-4}$)alkyl-cyclooctene, N-protected amino($C_{0-4}$)alkyl-bicycloalkene, respectively via epoxidation, ring opening of the epoxide obtained with a sulfur donating agent e.g. thiobenzoic acid, tritylthiol, thioacetic acid, preferably with thiobenzoic acid, followed by deprotection of the thiol function e.g. with hydrazine hydrate.

The compounds of the present invention exhibit pharmacological activity, e.g. in vitro, in vivo activity, and are therefore useful as pharmaceuticals.

For example, the compounds of the present invention show antimicrobial, e.g. antibacterial, activity against gram positive bacteria, such as coagulase positive Staphylococci, e.g. *Staphylococcus aureus*, coagulase negative Staphylococci, e.g. *Staphylococcus epidermidis, Staphylococcus haemolyticus*, and Streptococci, e.g. *Streptococcus pyogenes, Streptococcus pneumoniae*, Enterococci, e.g. *Enterococcus faecium* and *Listeria monocytogenes* and against gram negative bacteria such as *Moraxella*, e.g. *Moraxella catarrhalis*, and *Haemophilus*, e.g. *Haemophilus influenzae*, and *Legionella*, e.g. *Legionella pneumophila*, Neisseriaceae, e.g. *Neisseria gonorrhoeae*, as well as against Mycoplasms, *Chlamydia* and obligatory anaerobes, e.g. *Bacteroides fragilis, Clostridium difficile, Fusobacterium* spp., and *Propionibacterium* spp.

The in vitro activity against aerobic bacteria was determined by Agar Dilution Test or Microdilution Test according to the Clinical and Laboratory Standards Institute (CLSI, former NCCLS) Document M7-A7 Vol. 26, No. 2: "Methods for Dilution Antimicrobial Susceptibility Tests for Bacteria that Grow Aerobically—Approved Standard; Seventh Edition (2006)"; and the test against anaerobic bacteria was performed according to the Clinical and Laboratory Standards Institute (CLSI, former NCCLS), Document, M11-A6, Vol. 24, No. 2: "Methods for Antimicrobial Susceptibility Testing of Anaerobic Bacteria—Approved Standard; Sixth Edition (2004)" and the in vivo activity was tested by the septicemia mouse model against *Staphylococcus aureus*.

Compounds of the present invention are therefore suitable for the treatment and prevention of diseases which are mediated by microbes, e.g. by bacteria. Diseases which may also be treated include e.g. diseases mediated by *Helicobacter*, such as *Helicobacter pylori*, and diseases mediated by *Mycobacterium tuberculosis*. Diseases which may also be treated include in general inflammatory diseases, where microbes are mediating said inflammation, e.g. including acne.

In another aspect the present invention provides a compound of the present invention for use as a pharmaceutical, preferably as an antimicrobial, such as an antibiotic, e.g. an anti-anaerobic.

In another aspect the present invention provides a compound of the present invention for use in acne treatment.

In a further aspect the present invention provides a compound of the present invention for use in the preparation of a medicament for the treatment of diseases, mediated by microbes, such as bacterials, for example
- diseases mediated by bacteria, e.g. selected from Staphylococci, Streptococci, Enterococci;
- diseases mediated by bacteria, e.g. selected from *Moraxella, Haemophilus, Legionella*, Neisseriaceae;
- diseases mediated by *Helicobacter*;
- diseases mediated by *Mycobacterium tuberculosis*;
- e.g. diseases mediated by Mycoplasms, *Chlamydia* and obligatory anaerobes;

and for the treatment of acne.

In a further aspect the present invention provides a method of treatment of diseases mediated by microbes which comprises administering to a subject in need of such treatment an effective amount of a compound of the present invention e.g. in the form of a pharmaceutical composition.

In a further aspect the present invention provides a method of treatment of acne which comprises administering to a subject in need of such treatment an effective amount of a compound of the present invention e.g. in the form of a pharmaceutical composition.

Treatment includes treatment and prophylaxis.

For antimicrobial and acne treatment, the appropriate dosage will, of course, vary depending upon, for example, the chemical nature and the pharmacokinetic data of a compound of the present invention employed, the individual host, the mode of administration and the nature and severity of the conditions being treated. However, in general, for satisfactory results in larger mammals, for example humans, an indicated daily dosage is in the range of about 0.5 mg to 3 g of a compound of the present invention conveniently administered, for example, in divided doses up to four times a day.

A compound of the present invention may be administered by any conventional route, for example enterally, e.g. including nasal, buccal, rectal, oral administration; parenterally, e.g. including intravenous, intramuscular, subcutaneous administration; or topically, e.g. including epicutaneous, intranasal, intratracheal administration, e.g. in form of coated or uncoated tablets, capsules, injectable solutions or suspensions, e.g. in the form of ampoules, vials, in the form of creams, ointments, gels, pastes, inhaler powder, foams, tinctures, lipsticks, drops, sprays, or in the form of suppositories, e.g. in analogous manner to macrolides, such as erythromycins, e.g. clarithromycin or azithromycin.

A compound of the present invention may be administered in the form of a pharmaceutically acceptable salt, e.g. an acid addition salt or a base addition salt, e.g. a metal salt, or in free form, optionally in the form of a solvate. A compound of the present invention in the form of a salt exhibits the same order of activity as the compound in free form, optionally in the form of a solvate.

A compound of the present invention may be used for pharmaceutical treatment according to the present invention alone or in combination with one or more other pharmaceutically active agents. Such other pharmaceutically active agents include e.g. other antibiotics and antiinflammatory agents, and, if a compound of the present invention is used in the treatment of acne, other pharmaceutically agents include furthermore agents which are active against acne.

Combinations include fixed combinations, in which two or more pharmaceutically active agents are in the same formulation; kits, in which two or more pharmaceutically active agents in separate formulations are sold in the same package, e.g. with instruction for co-administration; and free combinations in which the pharmaceutically active agents are packaged separately, but instruction for simultaneous or sequential administration are given.

In another aspect the present invention provides a pharmaceutical composition comprising a compound of the present invention in free form or in the form of a pharmaceutically acceptable salt and/or in the form of a solvate as such or in association with at least one pharmaceutical, excipient, e.g. carrier or diluent, e.g. including fillers, binders, disintegrators, flow conditioners, lubricants, sugars and sweeteners, fragrances, preservatives, stabilizers, wetting agents and/or emulsifiers, solubilizers, salts for regulating osmotic pressure and/or buffers.

In another aspect the present invention provides a pharmaceutical composition according to the present invention, further comprising another pharmaceutically active agent.

Such pharmaceutical compositions may be manufactured according, e.g. analogously, to a method as conventional, e.g. by mixing, granulating, coating, dissolving or lyophilizing processes. Unit dosage form may contain, for example, from about 0.5 mg to about 2000 mg, such as 10 mg to about 500 mg.

The compounds of the present invention are additionally suitable as veterinary agents, e.g. veterinary active compounds, e.g. in the prophylaxis and in the treatment of microbial, e.g. bacterial diseases, in animals, such as fowl, pigs and calves, e.g., and for diluting fluids for artificial insemination and for egg-dipping techniques.

In another aspect the present invention provides a compound of the present invention for use as a veterinary agent.

In a further aspect the present invention provides a compound of the present invention for the preparation of a veterinary composition which is useful as a veterinary agent.

In another aspect the present invention provides a veterinary method for the prophylaxis and the treatment of microbial, e.g. bacterial diseases which comprises administering to a subject in need of such treatment an effective amount of a compound of the present invention, e.g. in the form of a veterinary composition.

The compounds of Examples 1 to 17 following thereafter exhibit MICs≤2 μg/mL against *Staphylococcus aureus* ATCC49951 and *Streptococcus pneumoniae* ATCC49619.

The trivial name mutilin refers to the IUPAC systematic name (1S, 2R, 3S, 4S, 6R, 7R, 8R, 14R)-3,6-dihydroxy-2,4,7,14-tetramethyl-4-vinyl-tricyclo[5.4.3.0$^{1,8}$]tetradecan-9-one. In the examples, pleuromutilin derivatives are numbered in analogy to the mutilin numbering system described by H. Berner (Berner, H.; Schulz, G.; Schneider H. *Tetrahedron* 1980, 36, 1807-1811.):

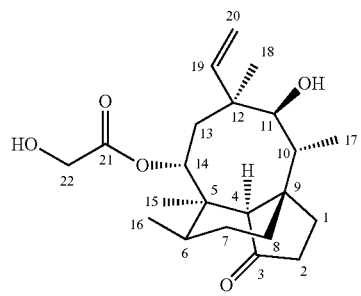 [SMILES: C=C[C@]1(C)C[C@@H](OC(=O)CO)[C@]2(C)C(C)CC[C@]3(CCC(=O)[C@H]32)[C@@H](C)[C@@H]1O]

Herein, including the examples the following abbreviations are used:
° C. degree Celsius
$^1$H NMR proton nuclear magnetic resonance spectroscopy
Boc,boc tert-butoxycarbonyl
BnBu$_3$NCl benzyltri-n-butylammonium chloride
Bu$_4$NCl tetrabutylammonium chloride hydrate
CyH cyclohexane
d day(s)
DBN 1,5-diazobicyclo[4.3.0]non-5-ene
DCM dichloromethane
DIPE diisopropylether
DMAP 4-(dimethylamino)-pyridine
DMF N,N-dimethylformamide
DMSO dimethylsulfoxide
DTT 1,4-dithio-DL-threitol
EDC N-(3-dimethylaminopropyl)-N'-ethylcarbodiimide hydrochloride
ESI+ electrospray ionization in positive mode
ESI− electrospray ionization in negative mode
EtOAc ethyl acetate
h hour(s)
HCl hydrochloric acid
heptane n-heptane
HOBT 1-hydroxybenzotriazole
HV high vacuum
LAH lithium aluminium hydride
M molarity
mCPBA metachloroperoxybenzoic acid
MeOH methanol
MIC minimum inhibitory concentration
min minutes
MS mass spectrometry
MTBE methyl tert-butyl ether
m/z mass/charge ratio
Ph phenyl
Rf retention factor, retardation factor
rt room temperature
TLC thin layer chromatography
TEA, Et$_3$N triethylamine
TFA trifluoroacetic acid
THF tetrahydrofuran
PLEU-Tos is a compound of formula

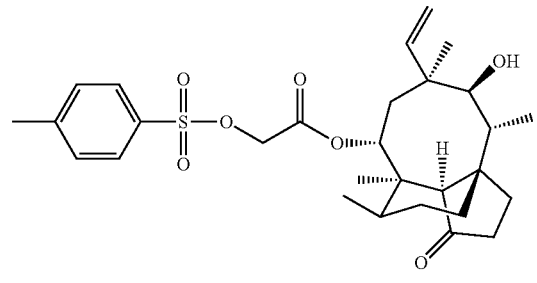

PLEU-Tos

PLEU is a residue of formula

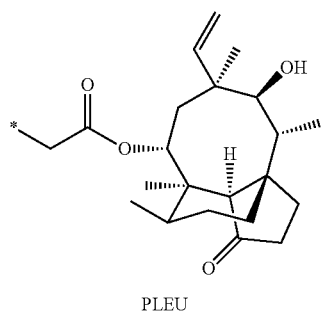 [SMILES: *CC(=O)O[C@@H]1C[C@@](C)(C=C)[C@@H](O)[C@H](C)[C@]23CCC(=O)[C@H]2[C@@]1(C)C(C)CC3]

PLEU

In the following examples all temperatures are in degrees Celsius (° C.) and are uncorrected.

EXAMPLE 1

14-O-{[(1R, 2R, 4R)-4-Amino-2-hydroxy-cyclopentylsulfanyl]-acetyl}-mutilin hydrochloride and the (1S, 2S, 4S) diastereomer thereof

A. syn and anti tert-Butyl (6-Oxa-bicyclo[3.1.0]hex-3-yl)-carbamate

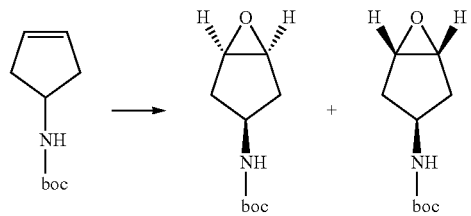

6.63 g of mCPBA (70%) was added at 0° C. to a solution of 4.7 g of N-Boc-cyclopent-3-enyl amine in 80 mL of DCM. The solution obtained was stirred at rt for 1.5 h, charged with 20 mL of 20% sodium thiosulfate, stirred for 10 min, DCM was added, phases obtained were separated and the organic layer obtained was washed with saturated NaHCO$_3$ solution. The aqueous layer obtained was extracted twice with DCM, the combined organic layers obtained were dried over magnesium sulfate and solvent was evaporated. 5.2 g of the crude product was obtained which was recrystallized twice from heptane. 917 mg of syn epoxide was obtained in the form of white needles. The mother liquors obtained were subjected to chromatography (silica, toluene/EtOAc=9:1-7:1). 3.51 g of anti epoxide in the form of a white amorphous solid was obtained.

Syn epoxide: $^1$H NMR (400MHz, DMSO-d$_6$, δ, ppm, characteristic signals): 1.36 (s, 9H), 6.79 (d, 1H, J=8Hz), 1.47 (dd, 1H, J=8Hz and 14Hz), 2.17 (dd, 1H, J=8Hz and 14Hz), 3.44 (s, 2H), 3.54 (m, 1H). MS-ESI+ (m/z): 200 (M+H). TLC: toluene/EtOAc=3:1, Rf=0.4.

Anti epoxide: $^1$H NMR (400MHz, DMSO-d$_6$, δ, ppm, characteristic signals): 1.35 (s, 9H), 1.78 (d, 2H, J=15Hz), 1.98 (dd, 1H, J=8Hz and 15Hz), 3.51 (s, 2H), 3.89 (q, 1H, J=8and 16Hz), 5.70 (d, 1H, J=8Hz). MS-ESI+ (m/z): 200 (M+H). TLC: toluene/EtOAc=3:1, Rf=0.45.

B. Thiobenzoic acid S-((1R, 2R, 4R)-4-tert-butoxycarbonylamino-2-hydroxy-cyclopentyl)ester and the (1S, 2S, 4S) diastereomer thereof

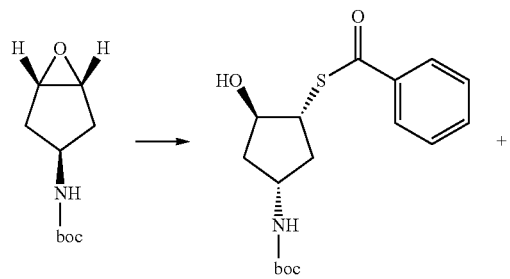

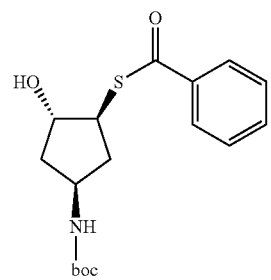

9.88 mL of thiobenzoic acid was added dropwise to a solution of 2.81 g of the anti epoxide from Example 1 Step A in 50 mL of toluene. To the mixture obtained 248 mg of Bu$_4$NCl was added and the resulting solution was stirred for 16 h at rt. To the mixture obtained 2 mL of thiobenzoic acid together with 500 mg of Bu$_4$NCl was added and stirring was continued for another 22 h. The mixture obtained was charged with saturated NaHCO$_3$ solution and stirred for 15 min. To the mixture obtained EtOAc was added, the phases obtained were separated and the organic phase obtained was washed 4 times with saturated NaHCO$_3$ solution, dried and solvent was evaporated. The evaporation residue obtained was subjected to chromatography (silica, toluene/EtOAc=98:2-8:1) to yield 4.65 g of Example 1, Step B products in the form of a white solid.

$^1$H NMR (200MHz, DMSO-d$_6$, δ, ppm, characteristic signals): 1.38 (s, 9H), 1.48 (m, 1H), 1.77 (m, 1H), 2.20 (m, 2H), 3.68-4.02 (m, 3H), 5.27 (d, 1H, J=6Hz), 6.98 (bd, 1H, J=8Hz), 7.40-7.92 (m, 5H). MS-ESI+ (m/z): 338 (M+H). TLC: DCM/MeOH=95:5, Rf=0.3.

C. 14-O-{[(1R, 2R, 4R)-4-tert-Butoxycarbonylamino-2-hydroxy-cyclopentylsulfanyl]-acetyl}-mutilin and the (1S, 2S, 4S) diastereomer

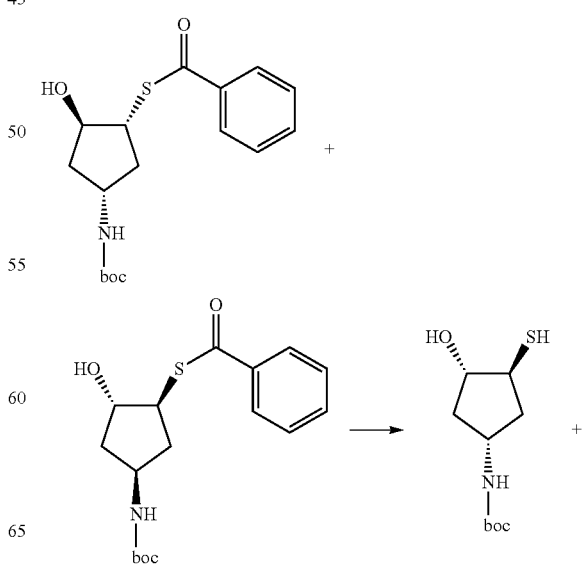

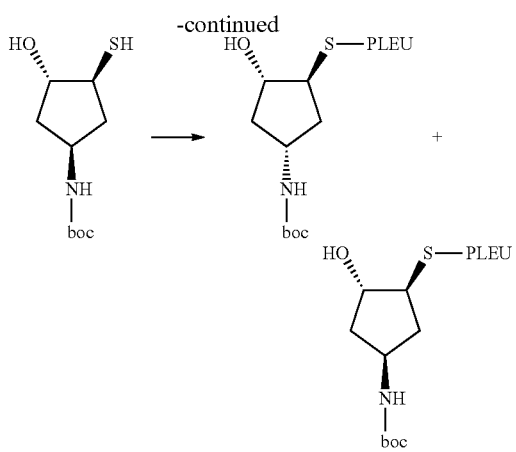

To a solution of 600 mg of Example 1, Step B products in 3 mL of DCM was added 180 μL of hydrazine monohydrate in two portions and the solution obtained was stirred for 20 min at rt. To the mixture obtained 4 mL of 1 M HCl was added, the mixture obtained was stirred for 5 min, diluted with DCM and the layers obtained were separated. The organic layer obtained was dried and solvent was evaporated to dryness. The evaporation residue obtained was dissolved in 10 mL of acetonitrile. To the mixture obtained 219 μL of DBN and 799 mg of pleuromutilin tosylate were added and the solution obtained was stirred for 1 h at rt. To the mixture obtained EtOAc was added, phases formed were separated and the organic phase obtained was washed with brine, dried and solvent was evaporated to dryness. The evaporation residue obtained was subjected to chromatography (silica, toluene/EtOAc=3:1-1:1). 797 mg of Example 1, Step C products in the form of white foam was obtained.

$^1$H NMR (200MHz, DMSO-$d_6$, δ, ppm, characteristic signals): 0.62 (d, 3H, J=6Hz), 0.82 (d, 3H, J=6Hz), 1.14 (s, 3H), 1.37 (s, 12H), 2.42 (bs, 1H), 3.06 (m, 1H), 3.36 (m, 3H), 3.77 (m, 2H), 4.53 (d, 1H, J=6Hz), 5.08 (m, 3H), 5.54 (bd, 1H, J=8Hz), 6.14 (dd, 1H, J=11 and 18Hz), 6.82 (t, 1H, J=4Hz). MS-ESI+ (m/z): 594 (M+H). TLC: DCM/MeOH=95:5, Rf=0.45.

D. 14-O-{[(1R, 2R, 4R)-4-tert-Amino-2-hydroxy-cyclopentylsulfanyl]-acetyl}-mutilin hydrochloride and the (1S, 2S, 4S) diastereomer

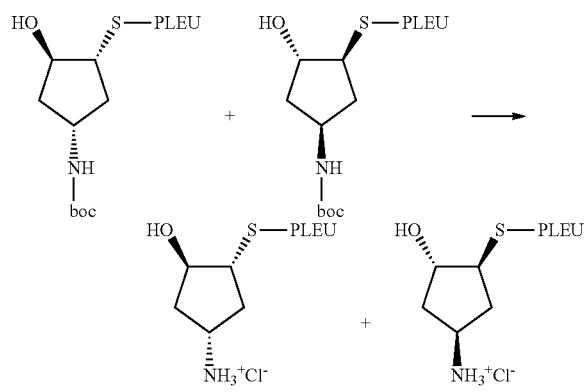

780 mg of Example 1, Step C products was dissolved in 10 mL of DCM, 8 mL of 1 M HCl in diethylether was added and the mixture obtained was stirred for 16 h at rt. To the mixture obtained 2 mL of 1 M HCl in diethylether was added and the mixture obtained was stirred for 8 h. From the mixture obtained solvent was evaporated, the solid evaporation residue obtained was triturated with diethylether and the mixture obtained was filtered. 579 mg of the Example 1, Step D products was obtained in the form of a white solid.

$^1$H NMR (200MHz, DMSO-$d_6$, δ, ppm, characteristic signals): 0.63 (d, 3H, J=6Hz), 0.82 (d, 3H, J=6Hz), 1.06 (s, 3H), 1.37 (s, 3H), 2.42 (bs, 1H), 3.12-3.60 (m, 5H), 3.90 (m, 1H), 4.59 (bs, 1H), 5.06 (m, 2H), 5.53 (bs, 1H), 5.60 (bd, 1H, J=12Hz), 6.13 (dd, 1H, J=11 and 18Hz), 8.06 (bs, 3H). MS-ESI+ (m/z): 494 (M+H). TLC: DCM/MeOH=6:1+1% NH$_4$OH, Rf=0.5.

EXAMPLE 2

14-O-{[(1R, 2R, 4S)-4-Amino-2-hydroxy-cyclopentylsulfanyl]-acetyl}-mutilin hydrochloride and the (1S, 2S, 4R) diastereomer thereof A. Thiobenzoic acid S-((1R, 2R, 4S)-4-tert-butoxycarbonylamino-2-hydroxy-cyclopentyl)ester and the (1S, 2S, 4R) diastereomer thereof

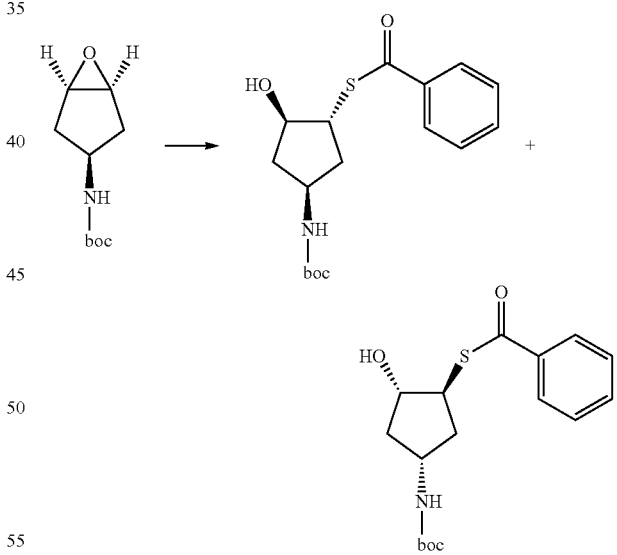

1.04 g of the syn epoxide from Example 1, Step A was treated according to the method of Example 1 Step B to obtain after chromatography (silica, toluene/EtOAc=98:2-7:1) 1.51 g of Example 2, Step A products in the form of a white solid.

$^1$H NMR (200MHz, DMSO-$d_6$, δ, ppm, characteristic signals): 1.37 (s, 9H), 1.45 (m, 1H), 1.80 (m, 2H), 2.55 (m, 1H), 3.60 (m, 1H), 4.02 (m, 2H), 5.19 (d, 1H, J=4Hz), 6.98 (d, 1H, J=6Hz), 7.40-7.90 (m, 5H). MS-ESI+ (m/z): 675 (2M+H), 338 (M+H). TLC: DCM/MeOH=95:5, Rf=0.25.

B. 14-O-{[(1R, 2R, 4S)-4-tert-Butoxycarbonylamino-2-hydroxy-cyclopentylsulfanyl]-acetyl}-mutilin and the (1S, 2S, 4R) diastereomer

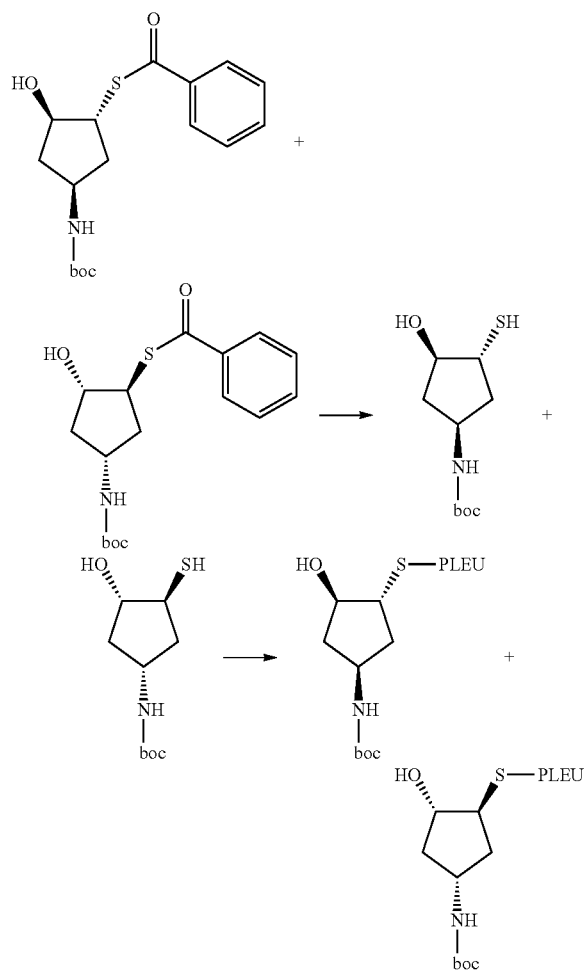

400 mg of Example 2, Step A products was treated according to the method of Example 1, Step C to obtain after chromatography (silica, toluene/EtOAc=2:1-1:2) 510 mg of Example 2, Step B products in the form of a white solid.

¹H NMR (200MHz, DMSO-d₆, δ, ppm, characteristic signals): 0.62 (d, 3H, J=6Hz), 0.82 (d, 3H, J=6Hz), 1.12 (s, 3H), 1.36 (s, 12H), 2.42 (bs, 1H), 2.89 (m, 1H), 3.40 (m, 3H), 3.90 (m, 1H), 4.54 (d, 1H, J=6Hz), 4.99 (d, 1H, J=4Hz), 5.08 (m, 2H), 5.54 (bd, 1H, J=8Hz), 6.14 (dd, 1H, J=11 and 18Hz), 6.88 (bd, 1H, J=8Hz). MS-ESI+ (m/z): 594 (M+H). TLC: DCM/MeOH=95:5, Rf=0.4.

C. 14-O-{[(1R, 2R, 4S)-4-tert-Amino-2-hydroxy-cyclopentylsulfanyl]-acetyl}-mutilin hydrochloride and the (1S, 2S, 4R) diastereomer

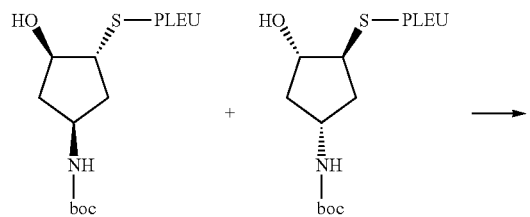

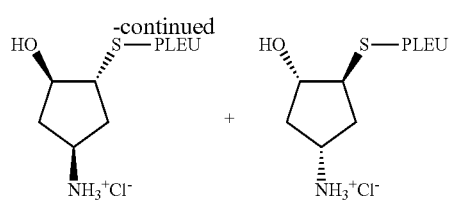

490 mg of the Example 2, Step B products was treated according to the method of Example 1 Step D to obtain 405 mg of Example 2, Step C products in the form of a white solid.

¹H NMR (200MHz, DMSO-d₆, δ, ppm, characteristic signals): 0.64 (d, 3H, J=6Hz), 0.82 (d, 3H, J=6Hz), 1.06 (s, 3H), 1.37 (s, 3H), 2.42 (bs, 1H), 2.97 (m, 1H), 3.43 (m, 3H), 4.00 (m, 1H), 4.58 (d, 1H, J=6Hz), 5.08 (m, 2H), 5.26 (d, 1H, J=4Hz), 5.55 (bd, 1H, J=9Hz), 6.13 (dd, 1H, J=11 and 18Hz), 8.10 (bs, 3H). MS-ESI+ (m/z): 494 (M+H). TLC: DCM/MeOH=6:1+1% NH₄OH, Rf=0.5.

EXAMPLE 3

14-O-{[(1R, 2R, 4R)-4-Aminomethyl-2-hydroxy-cyclopentylsulfanyl]-acetyl}-mutilin hydrochloride and the (1S, 2S, 4S) diastereomer thereof

A. Cyclopent-3-enyl-methanol

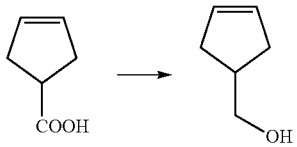

3.66 g of LAH was suspended in 100 mL of THF and to the suspension obtained 10.49 g of cyclopent-3-enecarboxylic acid dissolved in 40 mL of THF was added dropwise. The mixture obtained was kept at reflux for 2 h, cooled to rt and slowly water and 10% sulfuric acid were added. The mixture obtained was extracted with diethylether, the organic phase obtained was dried and solvent was carefully evaporated using a cold water bath. 10 g of Example 3, Step A product (still contains THF) was obtained in the form of a colorless liquid.

¹H-NMR (200MHz, CDCl₃, δ, ppm, characteristic signals): 1.73 (s, 1H), 2.10 (m, 2H), 2.50 (m, 3H), 3.49 (d, 2H, J=16Hz), 5.66 (s, 2H). TLC: toluene/EtOAc=3:1, Rf=0.35.

B. Methanesulfonic acid cyclopent-3-enylmethyl ester

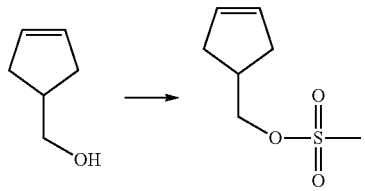

10.75 g of cyclopent-3-enyl-methanol from Example 3 Step A was dissolved in 200 mL of THF and to the mixture obtained 21 mL of N-methylmorpholine was added. To the mixture obtained 25.26 g of methanesulfonic anhydride was added in portions and the mixture obtained was stirred for 20 h at rt. To the mixture obtained EtOAc was added, phases obtained were separated and the organic phase obtained was washed with saturated NaHCO₃ solution and 1 M HCl. The organic phase obtained was dried and solvent was evaporated. 18.37 g of Example 3, Step B product was obtained in the form of a slightly yellow oil.

¹H-NMR (200MHz, CDCl₃, δ, ppm, characteristic signals): 2.12 (m, 2H), 2.55 (m, 2H), 2.70 (m, 1H), 3.01 (s, 3H), 4.12 (d, 2H, J=8Hz), 5.66 (s, 2H). MS-ESI+ (m/z): 375 (2M+Na), 199 (M+Na). TLC: toluene/EtOAc=3:1, Rf=0.5.

C. tert-Butyl Cyclopent-3-enylmethyl-carbamate

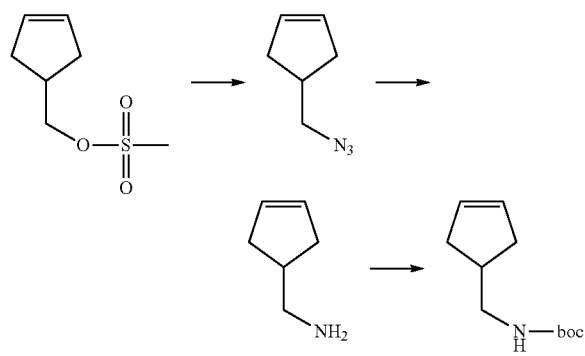

To 18.37 g of Example 3, Step B product dissolved in 200 mL of DMF was added 27.1 g of sodium azide and the reaction mixture obtained was stirred at 60° C. for 20 h. To the mixture obtained diethylether was added, the mixture obtained was washed with water, dried and solvent was carefully evaporated using a cold water bath. The crude azide product obtained still contains DMF and is used for the next step without further purification. 18.6 g of this crude azide product was dissolved in 150 mL of THF and 5 mL of water. To the mixture obtained 26.17 g of triphenylphosphine was added and the reaction mixture obtained was stirred at 80° C. for 4 h. The mixture obtained was allowed to cool down to 4° C. using an ice bath and 18.3 g of Boc-anhydride dissolved in 50 mL of THF was added. The mixture obtained was stirred at rt for 1.5 h, solvent was evaporated and the evaporation residue obtained was subjected to chromatography (silica, toluene/EtOAc=99:1-95:5). 13.16 g of Example 3, Step C product in the form of a colorless oil was obtained.

¹H-NMR (200 MHz, CDCl₃, δ, ppm, characteristic signals): 1.44 (s, 9H), 2.03 (m, 2H), 2.45 (m, 3H), 3.09 (bs, 2H), 5.65 (s, 2H). MS-ESI+ (m/z): 395 (2M+H), 142 (M–tBu). TLC: toluene/EtOAc=9:1, Rf=0.5.

D. Syn and anti tert-Butyl (6-Oxa-bicyclo[3.1.0]hex-3-ylmethyl)-carbamate

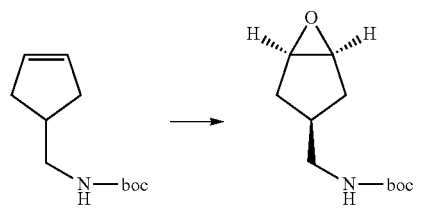

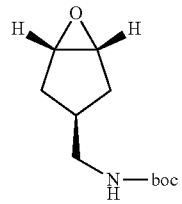

19.17 g of mCPBA was added in portions at 0° C. to a solution of 14.61 g of Example 3, Step C product in 130 mL of DCM. The solution obtained was stirred at rt for 1 h, poured onto 20% sodium thiosulfate and the mixture obtained was stirred for 10 min. To the mixture obtained DCM was added, the phases obtained were separated and the organic layer obtained was washed with saturated NaHCO₃ solution. The aqueous layer obtained was extracted with DCM and the combined organic layers were dried over MgSO₄ and solvent was evaporated. The evaporation residue obtained was subjected to chromatography (silica, CyH/EtOAc=95:5-8:1) and the fractions obtained were recrystallized from EtOAc/mixed heptanes and again subjected to chromatography (silica, CyH/EtOAc=9:1-6:1). 4.21 g of anti epoxide and 10.03 g of syn epoxide of Example 3, Step D product in the form of white solids were obtained.

Anti epoxide: ¹H-NMR (200 MHz, DMSO-d₆, δ, ppm, characteristic signals): 1.36 (s, 9H), 1.70 (m, 4H), 2.05 (m, 1H), 2.75 (dd, 2H, J=6Hz and 8Hz), 3.44 (s, 2H), 6.83 (t, 2H, J=6Hz). MS-ESI+ (m/z): 427 (2M+H), 214 (M+H), 158 (M–tBu). TLC: CyH/EtOAc=8:1, Rf=0.55.

Syn epoxide: ¹H-NMR (200 MHz, DMSO-d₆, δ, ppm, characteristic signals): 1.28 (m, 2H), 1.37 (s, 9H), 1.73 (m, 1H), 1.94 (m, 2H), 2.89 (t, 2H, J=6Hz), 3.41 (s, 2H), 6.84 (t, 1H, J=8Hz). MS-ESI+ (m/z): 449 (2M+Na), 214 (M+H), 158 (M–tBu). TLC: CyH/EtOAc=8:1, Rf=0.45.

E. Thiobenzoic acid S-[(1R, 2R, 4R)-4-(tert-butoxy-carbonylamino-methyl)-2-hydroxy-cyclopentyl]ester and the (1S, 2S, 4S) diastereomer thereof

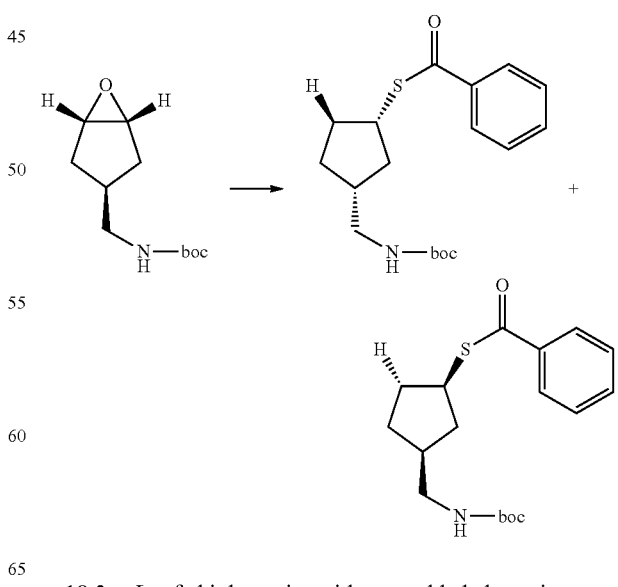

18.2 mL of thiobenzoic acid was added dropwise to a solution of 4.18 g of anti epoxide from Example 3, Step D in 110 mL of toluene containing 461 mg of Bu$_4$NCl. The reaction mixture obtained was stirred for 20 h at rt. To the mixture obtained saturated NaHCO$_3$ solution, and after 10 min, EtOAc was added, the phases obtained were separated and the organic phase obtained was washed twice with saturated NaHCO$_3$ solution, dried and solvent was evaporated. The evaporation residue obtained was subjected to chromatography (silica, toluene/EtOAc=97:3-9:1-7:1). 5.79 g of Example 3, Step E products in the form of a colorless oil were obtained.

$^1$H-NMR (200 MHz, DMSO-d$_6$, δ, ppm, characteristic signals): 1.26 (m, 1H), 1.36 (s, 9H), 1.70 (m, 1H), 2.05 (m, 2H), 2.18 (m, 1H), 2.96 (m, 2H), 3.70 (m, 1H), 4.00 (m, 1H), 5.18 (d, 1H, J=4Hz), 6.90 (t, 1H, J=6Hz), 7.45-7.92 (m, 5H). MS-ESI+ (m/z): 352 (M+H), 296 (M−tBu). TLC: DCM/MeOH=95:5, Rf=0.35.

F. 14-O-{[(1R, 2R, 4R)-4-tert-Butoxycarbonylaminomethyl-2-hydroxy-cyclopentylsulfanyl]-acetyl}-mutilin and the (1S, 2S, 4S) diastereomer thereof

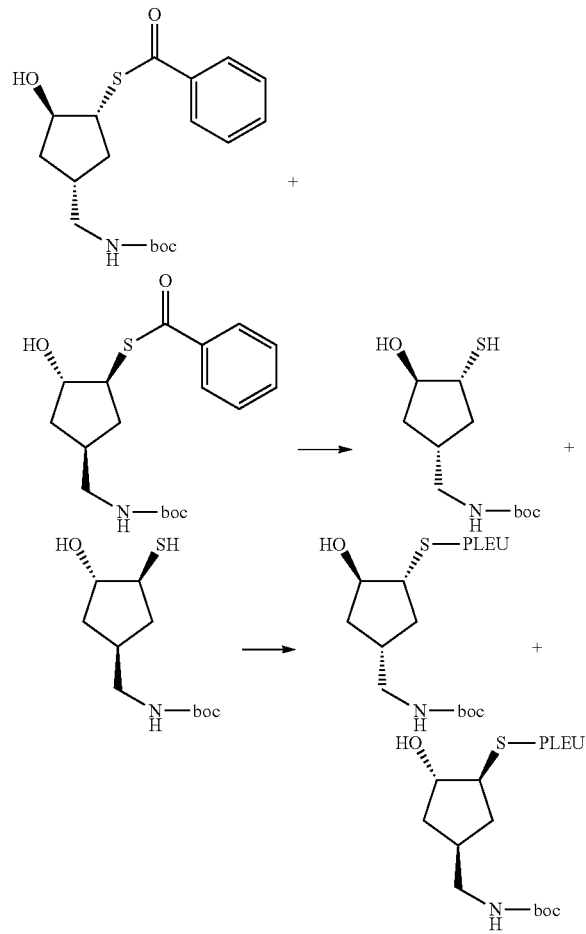

To a solution of 5.53 g of Example 3, Step E products in 80 mL of acetonitrile was added 1.56 mL of hydrazine monohydrate and the solution obtained was stirred for 30 min at rt. To the mixture obtained 25 mL of 1 M HCl was added and the mixture obtained was stirred for 5 min, diluted with DCM and the layers obtained were separated. The organic layer obtained was dried and solvent was evaporated. The evaporation residue obtained was dissolved in 100 mL of acetonitrile. To the mixture obtained 2.06 mL of DBN and 7.53 g of pleuromutilin tosylate was added and the solution obtained was stirred for 4 h at rt. To the mixture obtained EtOAc was added, the phases obtained were separated and the organic phase obtained was washed with brine, dried and solvent was evaporated. The evaporation residue obtained was subjected to chromatography (silica using DCM/MeOH=100:2). 7.16 g of Example 3, Step F products in the form of a white foam was obtained.

$^1$H-NMR (200 MHz, DMSO-d$_6$, δ, ppm, characteristic signals): 0.63 (d, 3H, J=6Hz), 0.82 (d, 3H, J=6Hz), 1.06 (s, 3H), 1.37 (s, 12H), 2.41 (bs, 1H), 2.87 (t, 2H, J=6Hz), 2.99 (m, 1H), 3.45 (m, 3H), 3.83 (m, 1H), 4.53 (d, 1H, J=6Hz), 4.98 (d, 1H, J=4Hz), 5.08 (m, 2H), 5.55 (d, 1H, J=8Hz), 6.14 (dd, 1H, J=11 and 18Hz), 6.84 (t, 1H, J=6Hz). MS-ESI+ (m/z): 608 (M+H). TLC: DCM/MeOH=95:5, Rf=0.35.

G. 14-O-{[(1R, 2R, 4R)-4-Aminomethyl-2-hydroxy-cyclopentylsulfanyl]-acetyl}-mutilin and the (1S, 2S, 4S) diastereomer thereof

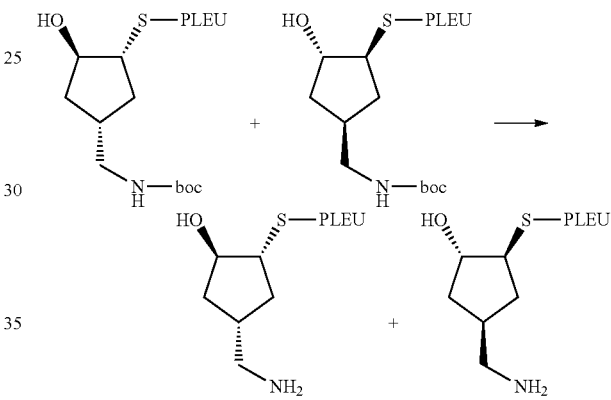

1 g of Example 3, Step F products was dissolved in 20 mL of DCM and to the mixture obtained 5 mL of 2 M HCl in diethylether was added. The mixture obtained was kept for 16 h at rt, solvent was evaporated and the evaporation residue obtained was subjected to chromatography (silica, DCM/MeOH/NH$_4$OH 100:8:0.8). 155 mg of the free base Example 3, Step G products in the form of a white foam was obtained.

$^1$H-NMR (200 MHz, DMSO-d$_6$, δ, ppm, characteristic signals): 0.63 (d, 3H, J=6Hz), 0.82 (d, 3H, J=6Hz), 1.06 (s, 3H), 1.37 (s, 12H), 2.42 (bs, 1H), 3.04 (m, 2H), 3.30-3.45 (m, 4H), 3.83 (m, 1H), 4.54 (d, 1H, J=6Hz), 5.06 (m, 2H), 5.55 (d, 1H, J=8Hz), 6.14 (dd, 1H, J=11 and 18Hz). MS-ESI+ (m/z): 508 (M+H). TLC: DCM/MeOH=9:1+1% NH$_4$OH, Rf=0.15.

H. 14-O-{[(1R, 2R, 4R)-4-Aminomethyl-2-hydroxy-cyclopentylsulfanyl]-acetyl}-mutilin hydrochloride and the (1S, 2S, 4S) diastereomer thereof

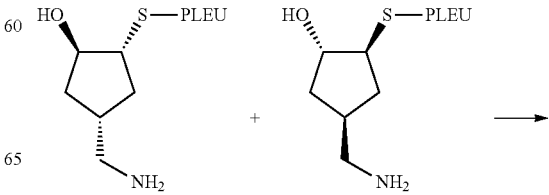

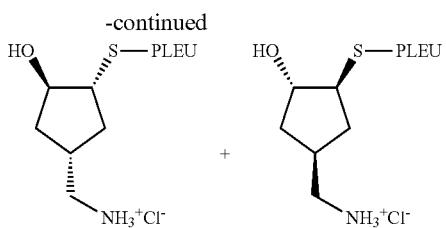

150 mg of the free base from Example 3, Step G was dissolved in 5 mL of DCM, 1 mL of 1 M HCl in diethylether was added, after 10 min solvent was evaporated and the hydrochloride of Example 3, Step H products was obtained in the form of a white solid in quantitative yield.

$^1$H-NMR (200 MHz, DMSO-$d_6$, δ, ppm, characteristic signals): 0.64 (d, 3H, J=6Hz), 0.82 (d, 3H, J=6Hz), 1.06 (s, 3H), 1.37 (s, 3H), 2.42 (bs, 1H), 2.75 (m, 1H), 3.10 (m, 1H), 3.30-3.45 (m, 3H), 3.59 (d, 1H, J=8Hz), 3.92 (m, 1H), 4.57 (d, 1H, J=6Hz), 5.08 (m, 2H), 5.55 (d, 1H, J=8Hz), 6.14 (dd, 1H, J=11 and 18Hz), 7.87 (bs, 3H). MS-ESI+ (m/z): 508 (M+H). TLC: DCM/MeOH=9:1+1% NH$_4$OH, Rf=0.15.

EXAMPLE 4

14-O-{[(1R, 2R, 4S)-4-Aminomethyl-2-hydroxy-cyclopentylsulfanyl]-acetyl}-mutilin hydrochloride and the (1S, 2S, 4R) diastereomer thereof A. Thiobenzoic acid S-[(1R, 2R, 4S)-4-(tert-butoxy-carbonylamino-methyl)-2-hydroxy-cyclopentyl]ester and the (1S, 2S, 4R) diastereomer thereof

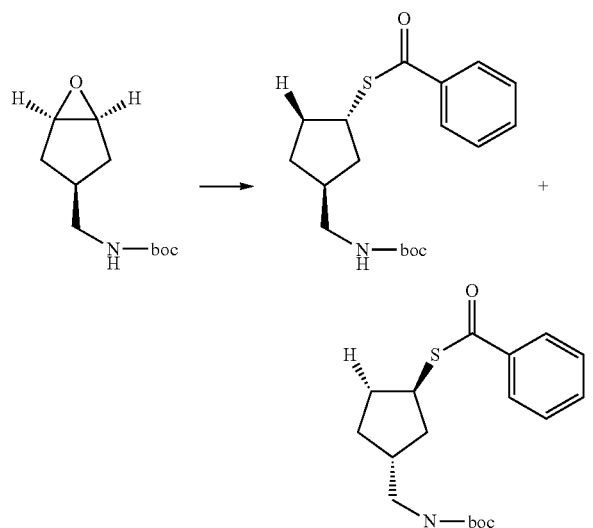

5 g of the syn epoxide from Example 3, Step D was treated according to the method of Example 3, Step E to obtain after chromatography (silica, toluene/EtOAc=9:1-7:1) 7.11 g of Example 4, Step A products in the form of a amorphous white solid.

$^1$H-NMR (200 MHz, DMSO-$d_6$, δ, ppm, characteristic signals): 1.27 (m, 1H), 1.37 (s, 9H), 1.62 (m, 2H), 2.30 (m, 2H), 2.89 (m, 2H), 3.63 (m, 1H), 4.00 (m, 1H), 5.11 (d, 1H, J=4Hz), 6.92 (t, 1H, J=6Hz), 7.50-7.95 (m, 5H). MS-ESI+ (m/z): 752 (2M+Na), 703 (2M+H), 352 (M+H), 296 (M−tBu). TLC: DCM/MeOH=95:5, Rf=0.4.

B. 14-O-{[(1R, 2R, 4S)-4-tert-Butoxycarbonylami-nomethyl-2-hydroxy-cyclopentylsulfanyl]-acetyl}-mutilin and the (1S, 2S, 4R) diastereomer thereof

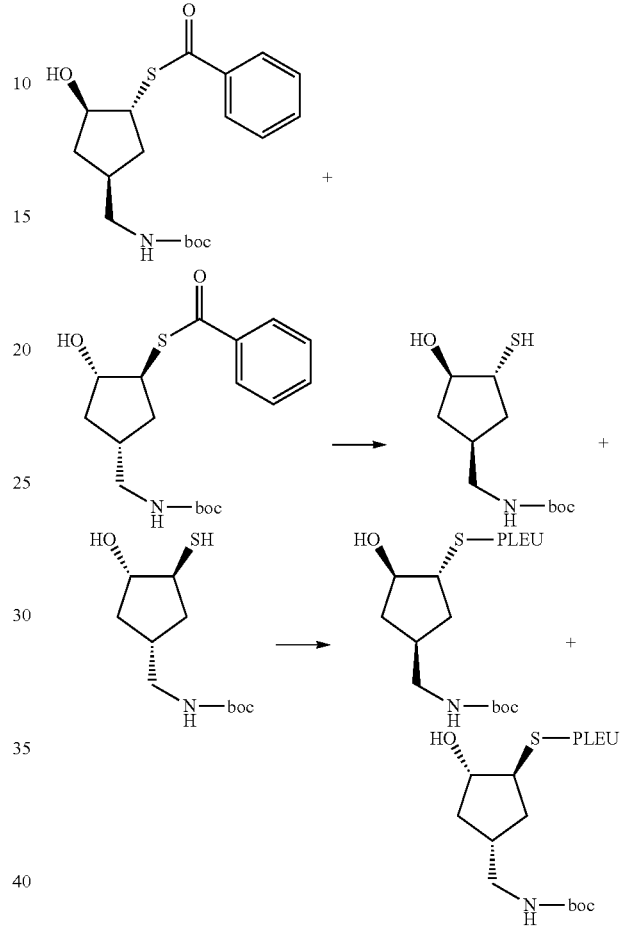

7 g of the Example 4, Step A products was treated according to the method of Example 3, Step F to obtain after chromatography (silica, DCM/MeOH=100:2) 9.41 g of the Example 4, Step B products in the form of a white foam.

$^1$H-NMR (200 MHz, DMSO-$d_6$, δ, ppm, characteristic signals): 0.63 (d, 3H, J=6Hz), 0.82 (d, 3H, J=6Hz), 1.06 (s, 3H), 1.37 (s, 12H), 2.42 (bs, 1H), 2.84 (t, 2H, J=6Hz), 2.93 (m, 1H), 3.25-3.48 (m, 3H), 3.87 (m, 1H), 4.53 (d, 1H, J=6Hz), 4.89 (d, 1H, J=6Hz), 5.08 (m, 2H), 5.55 (d, 1H, J=8Hz), 6.14 (dd, 1H, J=11 and 18Hz), 6.86 (t, 1H, J=4Hz). MS-ESI+ (m/z): 608 (M+H). TLC: DCM/MeOH=95:5, Rf=0.35.

C. 14-O-{[(1R, 2R, 4S)-4-Aminomethyl-2-hydroxy-cyclopentylsulfanyl]-acetyl}-mutilin and the (1S, 2S, 4R) diastereomer thereof

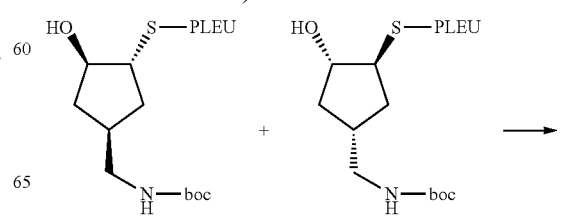

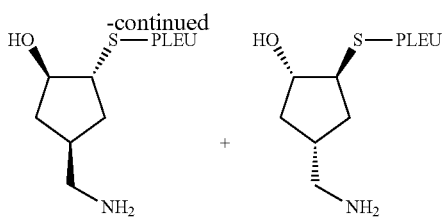

2 g of Example 4, Step B products was treated according to the method of Example 3, Step G to obtain after chromatography (silica, DCM/MeOH/NH$_4$OH 100:8:0.8) 906 mg of the free base of Example 4, Step C products.

TLC: DCM/MeOH=9:1+1% NH$_4$OH, Rf=0.15.

D. 14-O-{[(1R, 2R, 4S)-4-Aminomethyl-2-hydroxy-cyclopentylsulfanyl]-acetyl}-mutilin hydrochloride and the (1S, 2S, 4R) diastereomer thereof

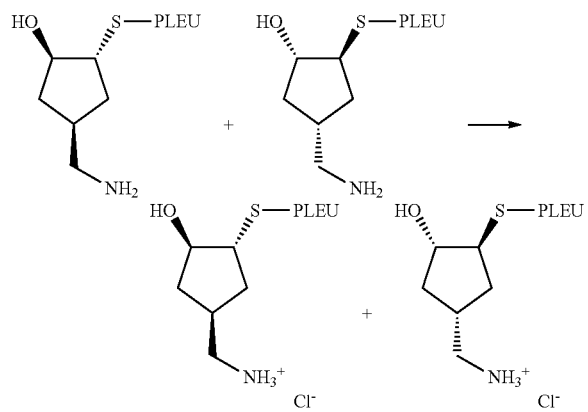

200 mg of Example 4, Step C products was dissolved in 5 mL of DCM and to the mixture obtained 1 mL of 1 M HCl in diethylether was added. After 10 min from the mixture obtained solvent was evaporated to dryness and 166 mg of the hydrochloride of Example 4 Step, D products was obtained in the form of a white amorphous solid.

$^1$H-NMR (200 MHz, DMSO-d$_6$, δ, ppm, characteristic signals): 0.63 (d, 3H, J=6Hz), 0.82 (d, 3H, J=6Hz), 1.06 (s, 3H), 1.37 (s, 3H), 2.42 (bs, 1H), 2.75 (t, 2H, J=6Hz), 3.01 (m, 1H), 3.40 (m, 3H), 3.95 (m, 1H), 4.56 (d, 1H, J=6Hz), 5.06 (m, 3H), 5.55 (d, 1H, J=6Hz), 6.14 (dd, 1H, J=11 and 18Hz), 7.87 (bs, 3H). MS-ESI+ (m/z): 508 (M+H). TLC: DCM/MeOH=9:1+1% NH$_4$OH, Rf=0.15.

EXAMPLE 5

14-O-{[(1R, 2R, 4S)-4-[(2,2-Dimethyl-propylamino)-methyl]-2-hydroxy-cyclopentylsulfanyl]-acetyl}-mutilin hydrochloride and the (1S, 2S, 4R) diastereomer thereof

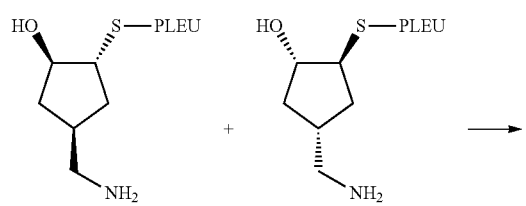

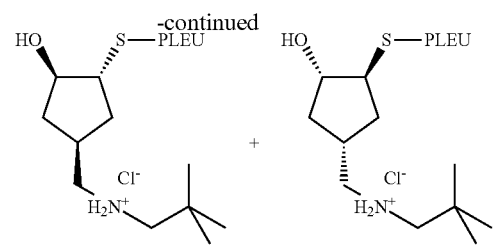

300 mg of Example 4, Step C products was dissolved in 15 mL of dry DCM containing molecular sieves. To the mixture obtained 42 mg of pivalaldehyde was added at rt, after 1 h the reaction mixture was charged with 136 mg of sodium triacetoxyborohydride and stirring was continued for another 23 h. To the mixture obtained DCM was added and the mixture obtained was washed with saturated NaHCO$_3$ solution, dried and solvent was evaporated. The evaporation residue obtained was subjected to chromatography (silica, DCM/MeOH=95:5-9:1). 68 mg of the free base products of Example 5 was obtained in the form of a white foam, was dissolved in 3 mL of DCM and to the mixture obtained 300 μL of 2 M HCl in diethylether was added. The mixture obtained was stirred and solvent was evaporated to dryness. 52 mg of the Example 5 title compounds in the form of a hydrochloride was obtained in the form of a white solid.

$^1$H-NMR (200 MHz, DMSO-d$_6$, δ, ppm, characteristic signals): 0.64 (d, 3H, J=6Hz), 0.82 (d, 3H, J=6Hz), 1.06 (s, 3H), 1.07 (s, 9H), 1.45 (s, 3H), 2.42 (bs, 1H), 2.73 (m, 2H), 2.90 (m, 2H), 3.02 (m, 1H), 3.30-3.45 (m, 3H), 3.92 (m, 1H), 4.58 (d, 1H, J=6Hz), 5.08 (m, 3H), 5.55 (d, 1H, J=8Hz), 6.15 (dd, 1H, J=11 and 18Hz), 8.39 (bs, 3H). MS-ESI– (m/z): 622 (M+HCOO$^-$), MS-ESI– (m/z): 578 (M+). TLC: DCM/MeOH=9:1, Rf=0.25.

EXAMPLE 6

14-O-{[(1R, 2R, 4S)-2-Hydroxy-4-[(2,2,2-trifluoro-acetylamino)-methyl]-cyclopentylsulfanyl]-acetyl}-mutilin and the (1S, 2S, 4R) diastereomer thereof

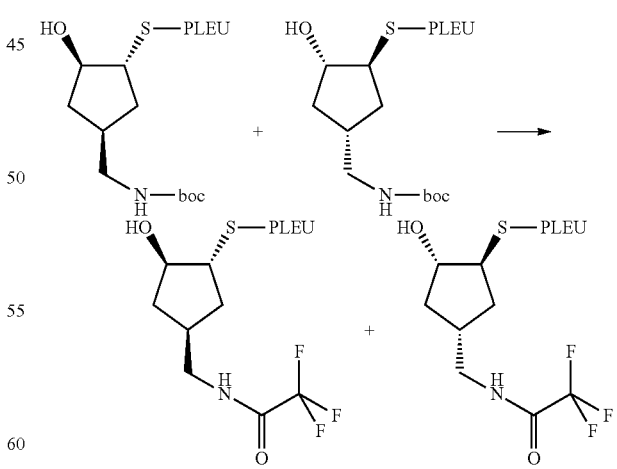

2 g (3.29 mmol) of Example 4, Step B products was dissolved in 20 mL of DCM and 2 mL of TFA was added. The mixture obtained was stirred for 7 h at rt. To the mixture obtained saturated NaHCO$_3$ solution was added, the phases obtained were separated and the organic phase obtained was extracted with DCM, dried and solvent was evaporated. The evaporation residue obtained was subjected to chromatography (silica, DCM using CH$_2$Cl$_2$/MeOH=98:2). 70 mg of the Example 6 title compounds in the form of a white foam was obtained.

$^1$H-NMR (200 MHz, DMSO-d$_6$, δ, ppm, characteristic signals): 0.63 (d, 3H, J=6Hz), 0.82 (d, 3H, J=6Hz), 1.06 (s, 3H), 1.37 (s, 3H), 2.41 (bs, 1H), 2.97 (m, 1H), 3.13 (t, 2H, J=6 Hz), 3.35 (m, 2H), 3.42 (m, 1H), 3.89 (m, 1H), 4.54 (d, 1H, J=6 Hz), 4.95 (d, 1H, J=6 Hz), 5.08 (m, 2H), 5.55 (d, 1H, J=8 Hz), 6.14 (dd, 1H, J=11 and 18 Hz), 9.45 (t, 1H, J=6 Hz). MS-ESI-(m/z): 648 (M+HCOO$^-$). TLC: DCM/MeOH=9:1, Rf=0.65.

EXAMPLE 7

14-O-{[(1R, 2R, 3S)-2-Hydroxy-3-[2-(2,2,2-trifluoro-acetylamino)-ethyl]-cyclopentylsulfanyl]-acetyl}-mutilin and the (1S, 2S, 3R) diastereomer thereof A. 2-Cyclopent-2-enyl-ethanol

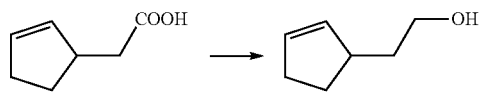

3.1 g of LAH was suspended in 100 mL of THF and to the mixture obtained 9.55 g of cyclopent-2-enyl-acetic acid dissolved in 40 mL of THF was added dropwise. The mixture obtained was kept at reflux for 1.5 h, cooled to rt and water and 10% sulfuric acid was added slowly. The mixture obtained was extracted with diethylether, the organic phase obtained was dried and solvent was carefully evaporated using a cold water bath. 11 g of Example 7, Step A product (still containing THF) in the form of a colorless liquid was obtained.

$^1$H-NMR (200 MHz, CDCl$_3$, δ, ppm, characteristic signals): 1.42 (m, 1H), 1.49 (s, 1H), 1.62 (m, 2H), 2.06 (m, 1H), 2.32 (m, 1H), 2.76 (m, 1H), 3.69 (t, 2H, J=6Hz), 5.70 (m, 2H). TLC: toluene/EtOAc=3:1, Rf=0.4.

B. Methanesulfonic acid 2-cyclopent-2-enyl-ethyl ester

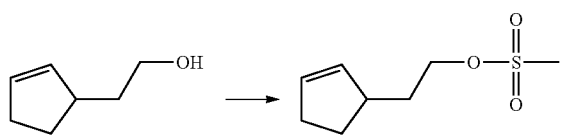

The crude cyclopent-3-enyl-ethanol obtained according to Example 7, Step A was dissolved in 200 mL of THF and to the mixture obtained 14.67 mL of N-methylmorpholine was added. To the mixture obtained 17.77 g of methanesulfonic anhydride was added in portions and the reaction mixture obtained was stirred for 20 h at rt. To the mixture obtained 1.5 mL of N-methylmorpholine and 1.8 g of methanesulfonic anhydride, and after another 6 h, EtOAc was added and the mixture obtained was washed with saturated NaHCO$_3$ solution and 1 M HCl. The organic phase obtained was dried and solvent was evaporated to dryness. 13.89 g of Example 7, Step B product in the form of a slightly yellow oil was obtained.

$^1$H-NMR (200 MHz, CDCl$_3$, δ, ppm, characteristic signals): 1.41 (m, 1H), 1.80 (m, 2H), 2.10 (m, 1H), 2.32 (m, 1H), 2.80 (m, 1H), 3.01 (s, 3H), 4.27 (t, 2H, J=6Hz), 5.63 and 5.77 (2×m, 2H). MS-ESI+ (m/z): 403 (2M+Na), 213 (M+Na), 208 (M+NH$_4$). TLC: toluene/EtOAc=3:1, Rf=0.65.

C. tert-Butyl (2-Cyclopent-2-enyl-ethyl)-carbamate

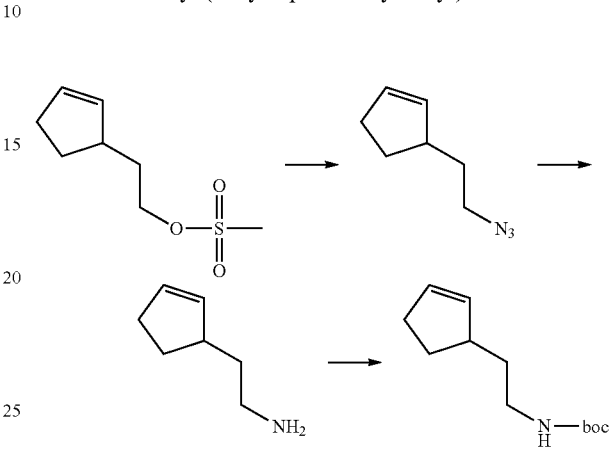

To 13.89 g of methanesulfonic acid cyclopent-3-enyl-ethyl ester from Example 7, Step B dissolved in 150 mL of DMF was added 18.9 g of sodium azide and the reaction mixture obtained was stirred at 60° C. for 20 h. To the mixture obtained diethylether was added, the mixture obtained was washed with water, dried and solvent was carefully evaporated using a cold water bath. The crude azide product obtained still contains DMF and is used for the next Step without further purification.

The 14.14 g of the crude azide from above was dissolved in 130 mL of THF and to the mixture obtained 5 mL of water was added. To the mixture obtained 22.98 g of triphenylphosphine was added and the reaction mixture obtained was stirred at 80° C. for 4 h. The mixture obtained was allowed to cool down to 4° C. using an ice bath and to the mixture obtained 17.5 g of Boc-anhydride dissolved in 50 mL of THF was added. The reaction mixture obtained was stirred at rt for 1.5 h, solvent was evaporated and the evaporation residue obtained was subjected to chromatography (silica, toluene/EtOAc=99:1-95:5). 2.05 g of the Example 7, Step C product in the form of a colorless oil was obtained.

$^1$H-NMR (200 MHz, CDCl$_3$, δ, ppm, characteristic signals): 1.25-1.62 (m, 3H), 1.37 (s, 9H), 2.02 (m, 1H), 2.25 (m, 1H), 2.62 (m, 1H), 3.11 (t, 2H, J=8Hz), 4.50 (bs, 1H), 5.54-5.70 (m, 2H). MS-ESI+ (m/z): 423 (2M+H). TLC: toluene/EtOAc=9:1, Rf=0.65.

D. Syn-[2-(6-Oxa-bicyclo[3.1.0]hex-2-yl)-ethyl]-carbamic acid tert-butyl ester

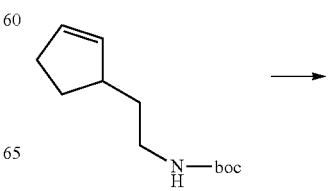

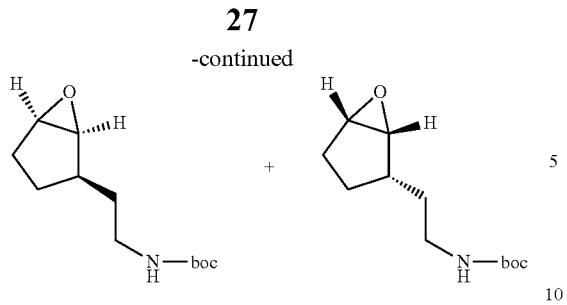

2.39 g of mCPBA (70%) was added at 0° C. to a solution of 1.95 g of Example 7, Step C product in 30 mL of DCM. The solution obtained was stirred at rt for 1.5 h, poured into 20% aqueous sodium thiosulfate solution and the mixture obtained was stirred for 10 min. To the mixture obtained DCM was added, the phases obtained were separated and the organic layer obtained was washed with aqueous saturated NaHCO$_3$ solution. The aqueous layer obtained was extracted with DCM and the combined organic layers obtained were dried over MgSO$_4$ and solvent was evaporated. The evaporation residue obtained was subjected to chromatography (silica, CyH/EtOAc=95:5-9:1). 1.8 g of Example 7, Step D products in the form of a colorless oil was obtained.

$^1$H-NMR (200 MHz, DMSO-d$_6$, δ, ppm, characteristic signals): 1.25-1.70 (m, 5H), 1.39 (s, 9H), 1.88 (m, 2H), 2.98 (m, 2H), 3.35 and 3.42 (2×m, 2H), 6.87 (bs, 1H). MS-ESI+ (m/z): 477 (2M+Na), 228 (M+H), 172 (M−tBu), 154 (M−OtBu). TLC: toluene/EtoAc=3:1, Rf=0.65.

E. Thiobenzoic acid S-[(1R, 2R, 5R)-5-(2-tert-bu-toxycarbonylamino-ethyl)-2-hydroxy-cyclopentyl) ester and the (1S, 2S, 5S) diastereomer thereof and Thiobenzoic acid S-[(1R, 2R, 3S)-3-(2-tert-butoxy-carbonylamino-ethyl)-2-hydroxy-cyclopentyl)ester and the (1S, 2S, 3R) diastereomer thereof

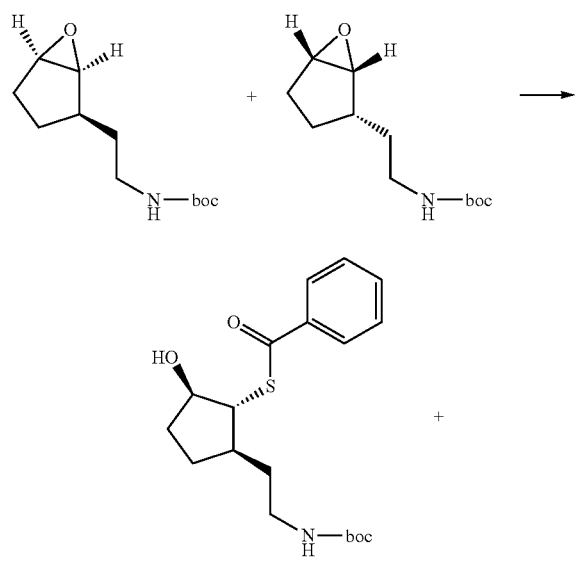

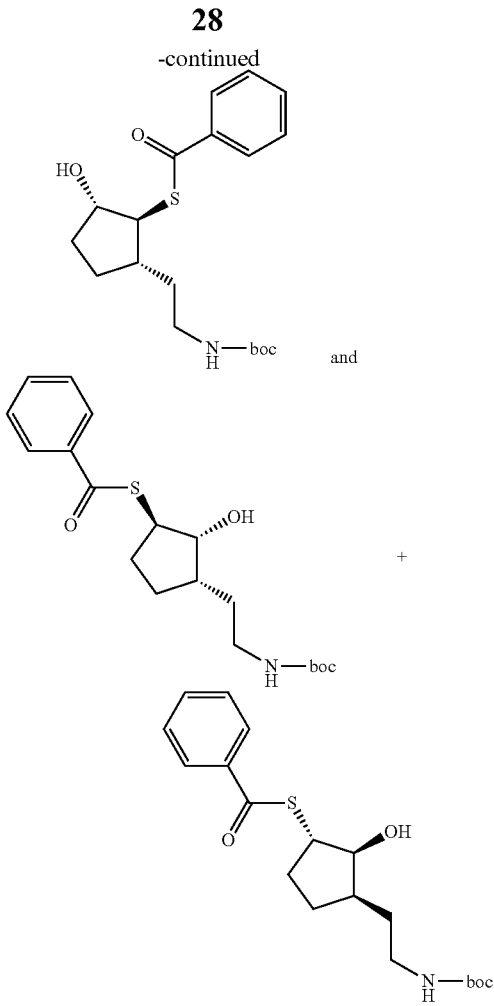

9.08 mL of thiobenzoic acid was added dropwise to a solution of 1.8 g of syn epoxides from Example 7, Step D in 40 mL of dry toluene containing 187 mg of Bu$_4$NCl. The reaction mixture was stirred for 20 h at rt. To the mixture obtained saturated NaHCO$_3$ solution was added and after 10 min the reaction mixture was charged with EtOAc. The organic phase obtained was washed 4 times with saturated NaHCO$_3$ solution, dried and solvent was evaporated. The evaporation residue obtained was subjected to chromatography (silica, toluene/EtOAc=95:5-8:1). 1.28 g of thiobenzoic acid S-[(1R, 2R, 5R)-5-(2-tert-butoxycarbonylamino-ethyl)-2-hydroxy-cyclopentyl]ester and the (1S, 2S, 5S) diasteromer thereof (late eluting compounds) in the form of a slightly yellow oil as well as 875 mg of thiobenzoic acid S-[(1R, 2R, 3S)-3-(2-tert-butoxycarbonylamino-ethyl)-2-hydroxy-cyclopentyl]ester and the (1S, 2S, 3R) diasteromer thereof (early eluting compounds) in the form of a colorless oil were obtained.

Late eluting products: $^1$H-NMR (200 MHz, DMSO-d$_6$, δ, ppm, characteristic signals): 1.30-1.95 (m, 7H), 1.38 (s, 9H), 2.93 (m, 2H), 3.45 (m, 1H), 3.99 (m, 1H), 5.11 (d, 1H, J=6Hz), 6.97 (t, 1H, J=6Hz), 7.50-7.98 (m, 5H). MS-ESI− (m/z): 410 (M+HCOO$^−$), MS-ESI+ (m/z): 366 (M+H). TLC: toluene/EtOAc=4:1, Rf=0.5.

Early eluting products: $^1$H-NMR (200 MHz, DMSO-d$_6$, δ, ppm, characteristic signals): 1.20-1.95 (m, 6H), 1.37 (s, 9H), 2.20-2.40 (m, 1H), 2.98 (m, 2H), 3.75 (m, 1H), 3.90 (bs, 1H), 5.10 (m, 1H), 6.77 (m, 1H), 7.45-7.95 (m, 5H). MS-ESI– (m/z): 410 (M+HCOO⁻), MS-ESI+ (m/z): 366 (M+H). TLC: toluene/EtOAc=4:1, Rf=0.55.

F. 14-O-{[(1R, 2R, 3S)-3-(2-tert-Butoxycarbony-lamino-ethyl)-2-hydroxy-cyclopentylsulfanyl]-acetyl}-mutilin and the (1S, 2S, 3R) diasteromer thereof

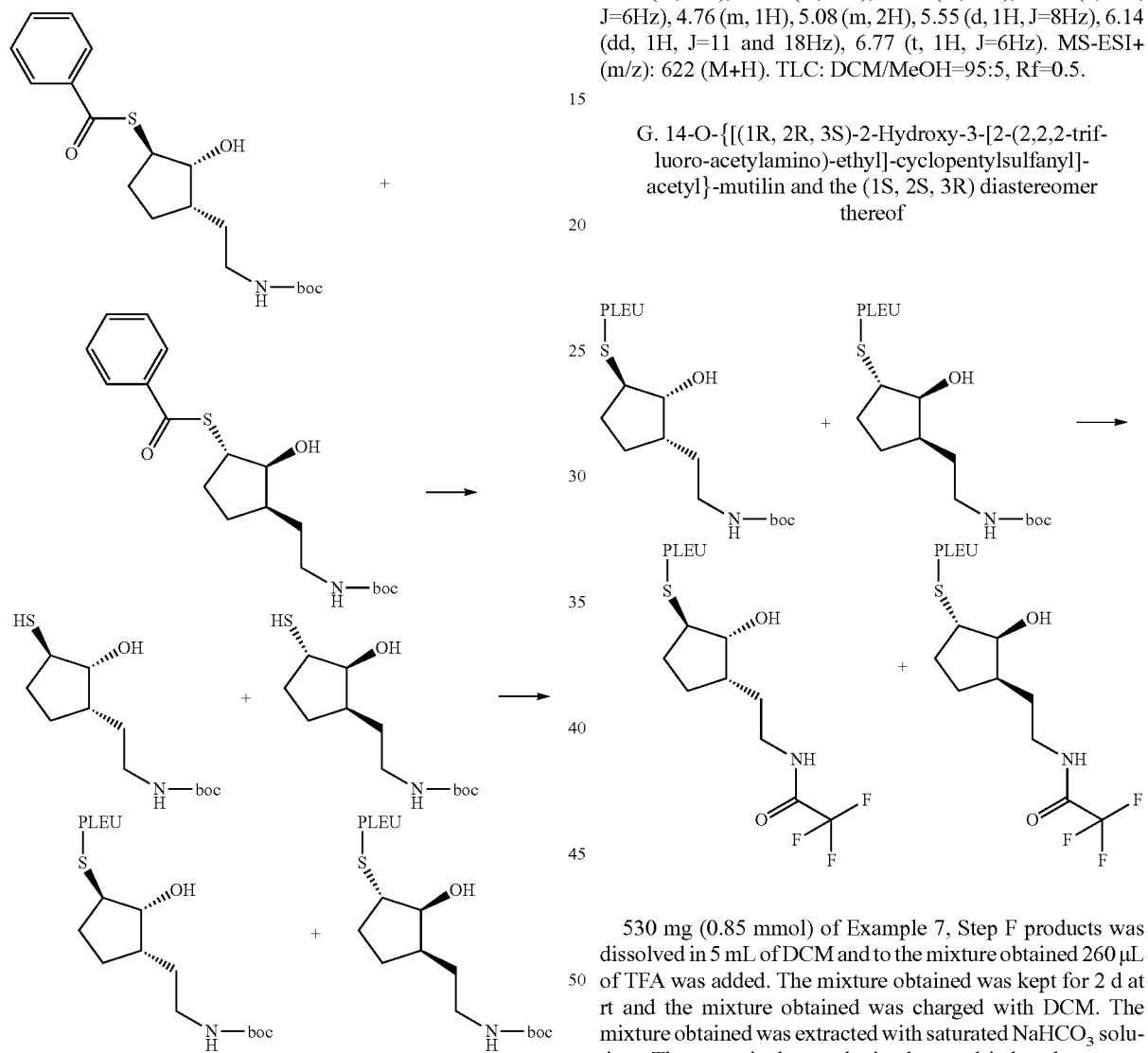

To a solution of 780 mg of thiobenzoic acid S-[(1R, 2R, 5R)-5-(2-tert-butoxycarbonylamino-ethyl)-2-hydroxy-cyclopentyl]ester and (1S, 2S, 5S) diasteromer thereof from Example 7, Step E in 10 mL of acetonitrile was added 210 μL of hydrazine monohydrate and the solution obtained was stirred for 30 min at rt. To the mixture obtained 25 mL of 1 M HCl was added, the mixture obtained was stirred for 5 min, diluted with DCM and the layers were separated. The organic layer obtained was washed with water and brine, dried and solvent was evaporated. The evaporation residue obtained was dissolved in 10 mL of acetonitrile. To the mixture obtained 279 μL of DBN and 1.13 g of pleuromutilin tosylate was added and the solution obtained was stirred for 1 h at rt. To the mixture obtained DCM was added and the mixture obtained was washed with brine, dried and solvent was evaporated. The evaporation residue obtained was subjected to chromatography (silica, DCM/MeOH=99:1). 546 mg of Example 7, Step F products in the form of a white foam was obtained.

¹H-NMR (200 MHz, DMSO-d₆, δ, ppm, characteristic signals): 0.63 (d, 3H, J=6Hz), 0.82 (d, 3H, J=6Hz), 1.06 (s, 3H), 1.37 (s, 12H), 2.42 (bs, 1H), 2.92 (m, 2H), 3.02 (m, 1H), 3.23 (m, 2H), 3.43 (m, 1H), 3.79 (m, 1H), 4.55 (d, 1H, J=6Hz), 4.76 (m, 1H), 5.08 (m, 2H), 5.55 (d, 1H, J=8Hz), 6.14 (dd, 1H, J=11 and 18Hz), 6.77 (t, 1H, J=6Hz). MS-ESI+ (m/z): 622 (M+H). TLC: DCM/MeOH=95:5, Rf=0.5.

G. 14-O-{[(1R, 2R, 3S)-2-Hydroxy-3-[2-(2,2,2-trifluoro-acetylamino)-ethyl]-cyclopentylsulfanyl]-acetyl}-mutilin and the (1S, 2S, 3R) diastereomer thereof 530 mg (0.85 mmol) of Example 7, Step F products was dissolved in 5 mL of DCM and to the mixture obtained 260 μL of TFA was added. The mixture obtained was kept for 2 d at rt and the mixture obtained was charged with DCM. The mixture obtained was extracted with saturated NaHCO₃ solution. The organic layer obtained was dried, solvent was evaporated and the evaporation residue obtained was subjected to chromatography (silica, DCM/MeOH/NH₄OH=9:1:0.1-4:1:0.1). 75 mg of Example 7, Step G products in the form of a white foam together with 384 mg of a mixed fraction containing starting material were obtained.

¹H-NMR (200 MHz, DMSO-d₆, δ, ppm, characteristic signals): 0.66 (d, 3H, J=6Hz), 0.84 (d, 3H, J=6Hz), 1.08 (s, 3H), 1.39 (s, 3H), 2.44 (bs, 1H), 3.06 (m, 1H), 3.20 (m, 2H), 3.30 (m, 2H), 3.45 (m, 1H), 3.83 (m, 1H), 4.57 (d, 1H, J=6Hz), 4.90 (m, 1H), 5.09 (m, 2H), 5.57 (d, 1H, J=8Hz), 6.16 (dd, 1H, J=11 and 18Hz), 9.43 (t, 1H, J=4Hz). MS-ESI– (m/z): 662 (M+HCOO⁻), MS-ESI+ (m/z): 635 (M+NH₄). TLC: DCM/MeOH=95:5, Rf=0.45.

EXAMPLE 8

14-O-{[(1R, 2R, 3S)-3-(2-Amino-ethyl)-2-hydroxy cyclopentylsulfanyl]-acetyl}-mutilin hydrochloride and the (1S, 2S, 3R) diastereomer A. 14-O-{[(1R, 2R, 3S)-3-(2-Amino-ethyl)-2-hydroxy cyclopentylsulfanyl]-acetyl}-mutilin and the (1S, 2S, 3R) diastereomer

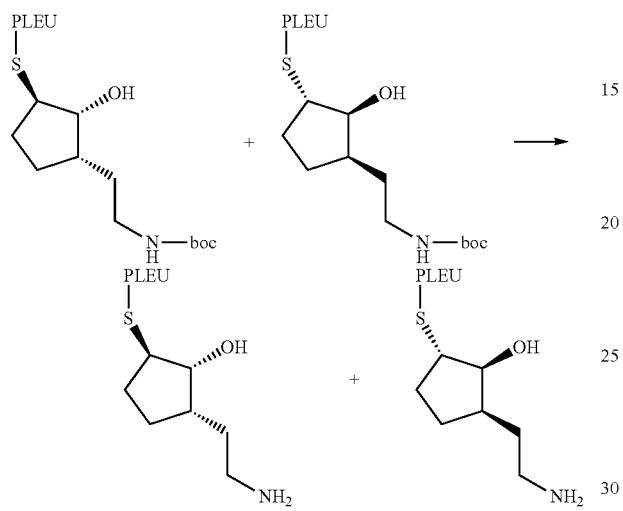

To a solution of 320 mg of Example 7, Step F products in 3 mL of MeOH was added 1 mL of 28% NH₄OH at rt, after 24 h a further 1 mL of 28% NH₄OH was added and the mixture obtained was stirred for additional 24 h. From the mixture obtained solvent was evaporated, the evaporation residue obtained was dissolved in DCM and the mixture obtained was extracted with saturated aqueous NaHCO₃ solution. The organic phase obtained was dried, solvent was evaporated and the evaporation residue obtained was subjected to chromatography (silica, DCM/MeOH=9:1-DCM/MeOH/NH₄OH=7:1:0.1). 88 mg of free base of Example 8, Step A products in the form of a white foam was obtained.

¹H-NMR (200 MHz, DMSO-d₆, δ, ppm, characteristic signals): 0.66 (d, 3H, J=6Hz), 0.84 (d, 3H, J=6Hz), 1.08 (s, 3H), 1.39 (s, 3H), 2.44 (bs, 1H), 3.07 (m, 1H), 3.28 (m, 2H), 3.45 (m, 1H), 3.81 (m, 1H), 4.58 (d, 1H, J=6Hz), 5.08 (m, 2H), 5.57 (d, 1H, J=8Hz), 6.16 (dd, 1H, J=11 and 18Hz). MS-ESI– (m/z): 566 (M+HCOO⁻), MS-ESI+ (m/z): 522 (M+H). TLC: DCM/MeOH=9:1+1% NH₄OH, Rf=0.30.

B. 14-O-{[(1R, 2R, 3S)-3-(2-Amino-ethyl)-2-hydroxy cyclopentylsulfanyl]-acetyl}-mutilin hydrochloride and the (1S, 2S, 3R) diastereomer

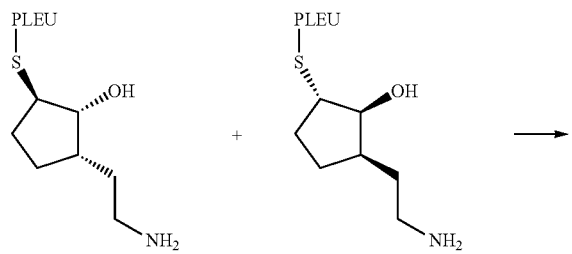

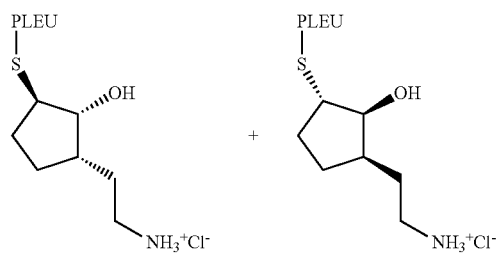

75 mg of the free base from Example 8 Step A was dissolved in DCM and to the mixture obtained HCl in diethyl-ether was added. From the mixture obtained solvent was evaporated and the hydrochlorides of the Example 8 title compounds were obtained in quantitative yield.

MS-ESI– (m/z): 556 (M+Cl⁻), MS-ESI+ (m/z): 522 (M+H). TLC: DCM/MeOH=9:1+1% NH₄OH, Rf=0.30.

EXAMPLE 9

14-O-{[(1R, 2R, 5R)-2-Hydroxy-5-[2-(2,2,2-trifluoro-acetylamino)-ethyl]-cyclopentylsulfanyl]-acetyl}-mutilin and the (1S, 2S, 5S) diastereomer thereof and 14-O-{[(1R, 2R, 5R)-5-(2-Amino-ethyl)-2-hydroxy-cyclopentylsulfanyl]-acetyl}-mutilin and the (1S, 2S, 5S) diastereomer thereof A. 14-O-{[(1R, 2R, 5R)-5-(2-tert-Butoxycarbonylamino-ethyl)-2-hydroxy-cyclopentylsulfanyl]-acetyl}-mutilin and the (1S, 2S, 5S) diastereomer thereof

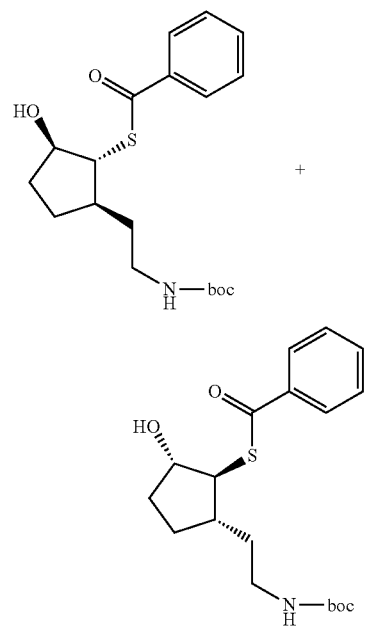

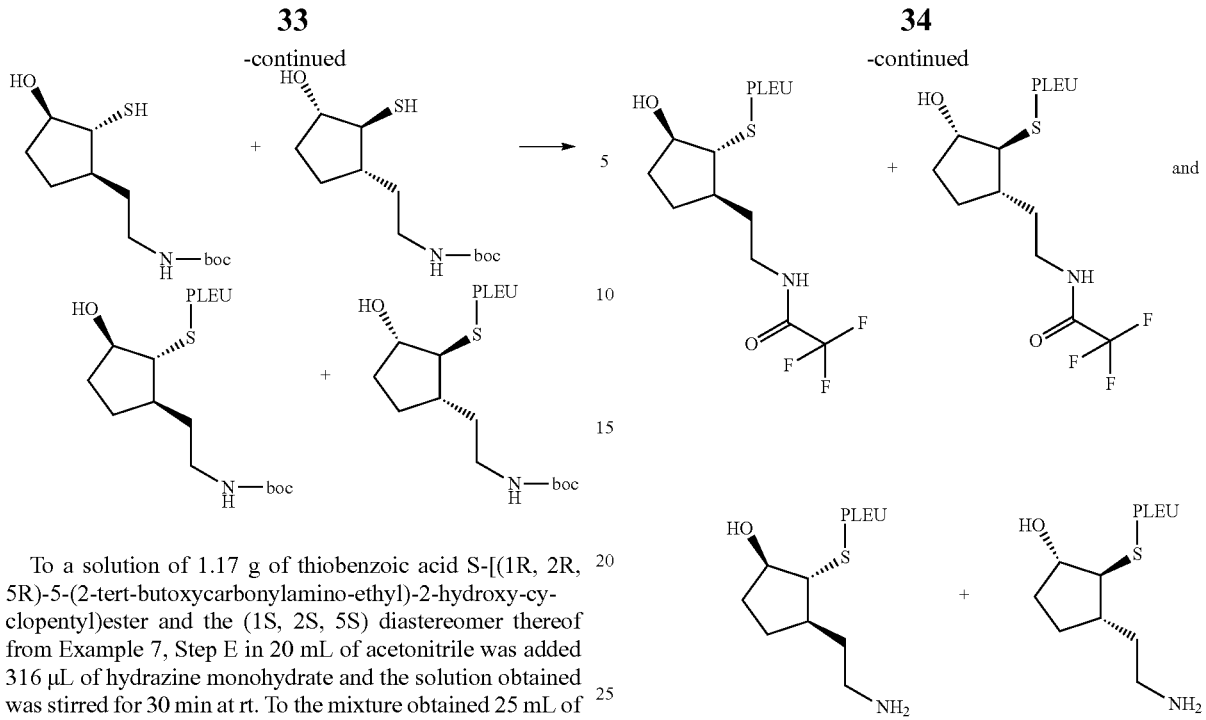

To a solution of 1.17 g of thiobenzoic acid S-[(1R, 2R, 5R)-5-(2-tert-butoxycarbonylamino-ethyl)-2-hydroxy-cyclopentyl)ester and the (1S, 2S, 5S) diastereomer thereof from Example 7, Step E in 20 mL of acetonitrile was added 316 μL of hydrazine monohydrate and the solution obtained was stirred for 30 min at rt. To the mixture obtained 25 mL of 1 M HCl was added, the mixture obtained was stirred, diluted with DCM and the layers obtained were separated. The organic layer obtained was washed with water and brine, dried and solvent was evaporated. The evaporation residue obtained was dissolved in 20 mL of acetonitrile. To the mixture obtained 420 μL of DBN and 1.53 g of pleuromutilin tosylate were added and the solution obtained was stirred for 2 h at rt. The mixture obtained was charged with DCM and the mixture obtained was washed with brine, dried and solvent was evaporated. The evaporation residue obtained was subjected to chromatography (silica, DCM/MeOH=98:2-95:5). 1.21 g of Example 9 Step A products in the form of a white foam was obtained.

$^1$H-NMR (200 MHz, DMSO-d$_6$, δ, ppm, characteristic signals): 0.65 (d, 3H, J=6Hz), 0.84 (d, 3H, J=6Hz), 1.08 (s, 3H), 1.38 (s, 12H), 2.43 (bs, 1H), 2.56 (m, 1H), 2.90 (m, 2H), 3.34 (m, 2H), 3.46 (m, 1H), 3.92 (m, 1H), 4.56 (d, 1H, J=6Hz), 4.92 (t, 1H, J=4Hz), 5.09 (m, 2H), 5.57 (d, 1H, J=8Hz), 6.16 (dd, 1H, J=11 and 18Hz), 6.81 (m, 1H). MS-ESI+ (m/z): 622 (M+H). TLC: DCM/MeOH=95:5, Rf=0.45.

B. 14-O-{[(1R, 2R, 5R)-2-Hydroxy-5-[2-(2,2,2-trifluoro-acetylamino)-ethyl]-cyclopentylsulfanyl]-acetyl}-mutilin and the (1S, 2S, 5S) diastereomer thereof and 14-O-{[(1R, 2R, 5R)-5-(2-Amino-ethyl)-2-hydroxy-cyclopentylsulfanyl]-acetyl}-mutilin and the (1S, 2S, 5S) diastereomer thereof

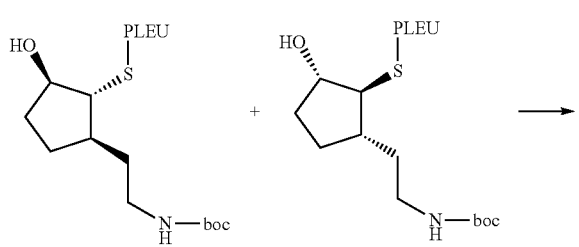

To a solution of 1.16 g (1.86 mmol) of the Example 9, Step A products from above in 10 mL of DCM was added 285 μL of TFA and the mixture obtained was stirred for 24 h at rt. To the mixture obtained 300 μL of TFA was added and the reaction mixture was stirred for additional 24 h at rt. To the mixture obtained DCM and saturated NaHCO$_3$ solution was added, and the phases obtained were separated. The organic phase obtained was dried and the solvent was evaporated. The evaporation residue obtained was subjected to chromatography (silica, DCM/MeOH=98:2-DCM/MeOH/NH$_4$OH=9:1: 0.1-DCM/MeOH/NH$_4$OH=4:1:0.1). 50 mg of 14-O-{[(1R, 2R, 5R)-2-Hydroxy-5-[2-(2,2,2-trifluoro-acetylamino)-ethyl]-cyclopentylsulfanyl]-acetyl}-mutilin and the (1S, 2S, 5S) diastereomer thereof in the form of a white foam as well as 142 mg of 14-O-{[(1R, 2R, 5R)-5-(2-Amino-ethyl)-2-hydroxy-cyclopentylsulfanyl]-acetyl}-mutilin and the (1S, 2S, 5S) diastereomer thereof in the form of a white foam were obtained.

Acetamide: $^1$H-NMR (200 MHz, DMSO-d$_6$, δ, ppm, characteristic signals): 0.65 (d, 3H, J=6Hz), 0.83 (d, 3H, J=6Hz), 1.07 (s, 3H), 1.39 (s, 3H), 2.43 (bs, 1H), 2.58 (m, 1H), 3.20 (m, 2H), 3.48 (m, 3H), 3.94 (m, 1H), 4.55 (m, 1H), 4.94 (t, 1H, J=4Hz), 5.09 (m, 2H), 5.57 (d, 1H, J=8Hz), 6.16 (dd, 1H, J=11 and 18Hz), 9.45 (m, 1H). MS-ESI− (m/z): 662 (M+HCOO$^−$), MS-ESI+ (m/z): 635 (M+NH$_4$). TLC: DCM/MeOH=95:5, Rf=0.4.

Free Base: $^1$H-NMR (200 MHz, DMSO-d$_6$, δ, ppm, characteristic signals): 0.66 (d, 3H, J=6Hz), 0.84 (d, 3H, J=6Hz), 1.08 (s, 3H), 1.40 (s, 3H), 2.44 (bs, 1H), 2.65 (m, 3H), AB-system ($υ_A$=3.44, $υ_B$=3.29, J=28Hz), 3.48 (m, 1H), 3.95 (m, 1H), 4.59 (bs, 2H, J=6Hz), 5.08 (m, 2H), 5.57 (d, 1H, J=8Hz), 6.17 (dd, 1H, J=11 and 18Hz). MS-ESI− (m/z): 566 (M+HCOO$^−$), MS-ESI+ (m/z): 522 (M+H). TLC: DCM/MeOH=95:5+1% NH$_4$OH, Rf=0.35.

EXAMPLE 10

14-O-{[(1R, 2R, 5R)-5-(2-Amino-ethyl)-2-hydroxy-cyclopentylsulfanyl]-acetyl}-mutilin hydrochloride and the (1S, 2S, 5S) diastereomer thereof

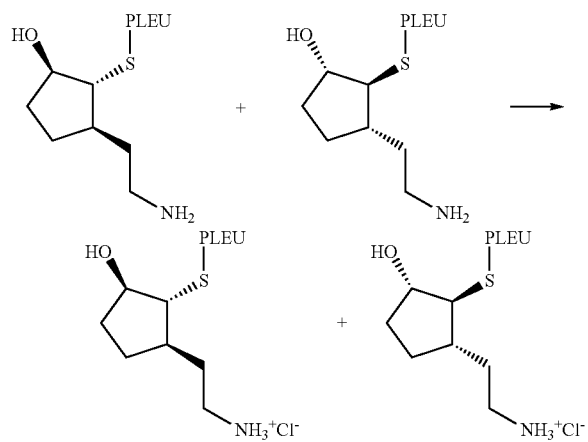

100 mg of the free base from Example 9, Step B was dissolved in DCM and to the mixture obtained 2 M HCl in diethylether was added. From the mixture obtained solvent was evaporated and the hydrochlorides of the Example 10 title compounds were obtained in quantitative yield.

MS-ESI− (m/z): 556 (M+Cl−), MS-ESI+ (m/z): 522 (M+H). TLC: DCM/MeOH=95:5+1% NH₄OH, Rf=0.35.

EXAMPLE 11

14-O-{[(1R, 2R, 5R)-5-[2-(2,2-Dimethyl-propylamino)-ethyl]-2-hydroxy-cyclopentylsulfanyl]-acetyl}-mutilin hydrochloride and the (1S, 2S, 5S) diastereomer thereof A. 14-O-{[(1R, 2R, 5R)-5-[2-(2,2-Dimethyl-propylamino)-ethyl]-2-hydroxy-cyclopentylsulfanyl]-acetyl}-mutilin and the (1S, 2S, 5S) diastereomer thereof

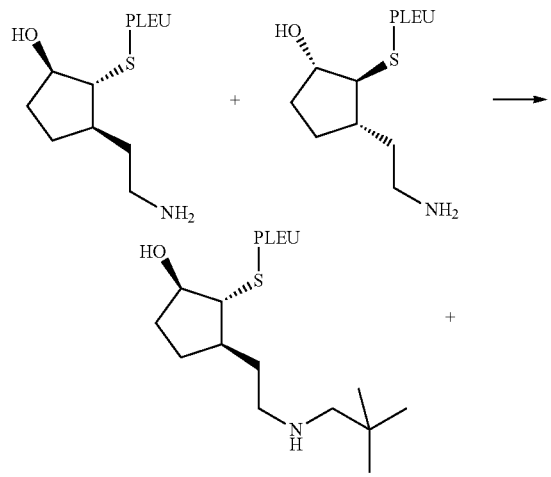

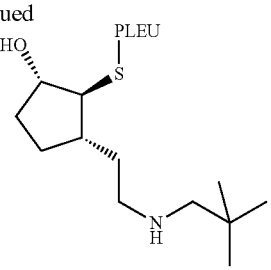

104 mg of 14-O-{[(1R, 2R, 5R)-5-(2-Amino-ethyl)-2-hydroxy-cyclopentylsulfanyl]-acetyl}-mutilin and the (1S, 2S, 5S) diastereomer thereof from Example 9, Step B was dissolved in 2 mL of DCM. To the mixture obtained 22 μl of pivalaldehyde was added at rt and the reaction mixture obtained was stirred for 2 h. To the mixture obtained 55 mg of sodium triacetoxyborohydride was added and stirring was continued for 18 h. To the mixture obtained DCM was added and the mixture obtained was washed with aqueous saturated NaHCO₃ solution, dried and solvent was evaporated. The evaporation residue obtained was subjected to chromatography (silica, DCM/MeOH=98:2-95:5-9:1). 58 mg of Example 11, Step A products was obtained in the form of a white foam.

¹H-NMR (200 MHz, DMSO-d₆, δ, ppm, characteristic signals): 0.66 (d, 3H, J=6Hz), 0.84 (d, 3H, J=6Hz), 0.91 (s, 9H), 1.09 (s, 3H), 1.40 (s, 3H), 2.44 (bs, 1H), 3.30-3.50 (m, 4H), 3.94 (m, 1H), 4.58 (d, 1H, J=6Hz), 4.97 (m, 1H), 5.10 (m, 2H), 5.58 (d, 1H, J=8Hz), 6.17 (dd, 1H, J=11 and 18Hz). MS-ESI+ (m/z): 592 (M+H). TLC: DCM/MeOH=9:1+1% NH₄OH, Rf=0.45.

B. 14-O-{[(1R, 2R, 5R)-5-[2-(2,2-Dimethyl-propylamino)-ethyl]-2-hydroxy-cyclopentylsulfanyl]-acetyl}-mutilin hydrochloride and the (1S, 2S, 5S) diastereomer thereof 47 mg of the free base from Example 11, Step A was dissolved in DCM and to the mixture obtained 2 M HCl in diethylether was added. The mixture obtained was stirred and solvent was evaporated. 48 mg of the hydrochloride Example 11 title compounds was obtained in the form of a white solid.

MS-ESI+ (m/z): 592 (M+H). TLC: DCM/MeOH=9:1+1% NH₄OH, Rf=0.45.

EXAMPLE 12

14-O-{[(1R, 2R, 5R)-5-Amino-2-hydroxy-cycloheptylsulfanyl]-acetyl}-mutilin hydrochloride and the (1S, 2S, 5S), (1R, 2R, 5S), (1S, 2S, 5R) diastereomers thereof A. tert-Butyl cyclohept-4-enyl-carbamate

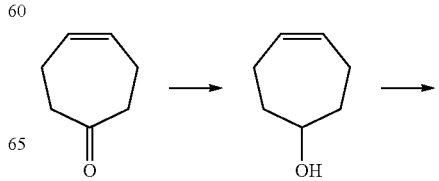

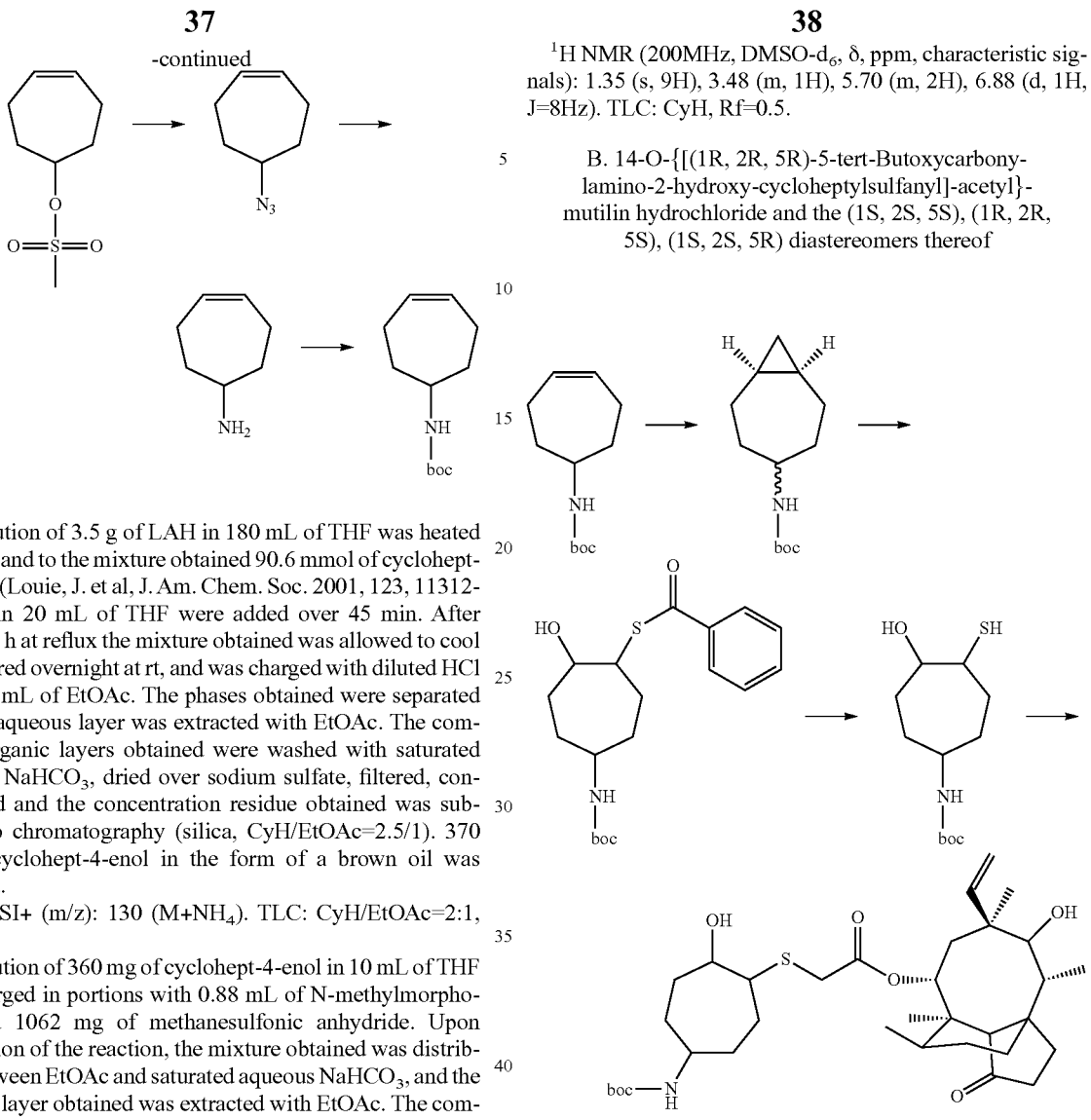

A solution of 3.5 g of LAH in 180 mL of THF was heated to reflux and to the mixture obtained 90.6 mmol of cyclohept-4-enone (Louie, J. et al, J. Am. Chem. Soc. 2001, 123, 11312-11313) in 20 mL of THF were added over 45 min. After further 4 h at reflux the mixture obtained was allowed to cool to rt, stirred overnight at rt, and was charged with diluted HCl and 100 mL of EtOAc. The phases obtained were separated and the aqueous layer was extracted with EtOAc. The combined organic layers obtained were washed with saturated aqueous NaHCO$_3$, dried over sodium sulfate, filtered, concentrated and the concentration residue obtained was subjected to chromatography (silica, CyH/EtOAc=2.5/1). 370 mg of cyclohept-4-enol in the form of a brown oil was obtained.

MS-ESI+ (m/z): 130 (M+NH$_4$). TLC: CyH/EtOAc=2:1, Rf=0.4.

A solution of 360 mg of cyclohept-4-enol in 10 mL of THF was charged in portions with 0.88 mL of N-methylmorpholine and 1062 mg of methanesulfonic anhydride. Upon completion of the reaction, the mixture obtained was distributed between EtOAc and saturated aqueous NaHCO$_3$, and the aqueous layer obtained was extracted with EtOAc. The combined organic layers obtained were washed with 1N HCl, water and brine, dried over sodium sulfate and filtered. The filtrate obtained was concentrated to dryness to give the corresponding mesylate in the form of a yellow oil in quantitative yield.

MS-ESI+ (m/z): 208 (M+NH$_4$), 398 (2M+NH$_4$). TLC: CyH/EtOAc=2:1, Rf=0.5.

3.2 mmol of the mesylate from above was heated to 60° C. overnight with 840 mg of sodium azide in 10 mL of DMF. The reaction mixture obtained was charged with water and extracted twice with diethylether. The combined organic layers obtained containing the crude azide were concentrated and used for the next Step.

MS-ESI– (m/z): 136 (M–H). TLC: CyH/EtOAc=3:1, Rf=0.9.

To the crude azide from above in 10 mL of THF and 0.5 mL of water was added 1 g of triphenylphosphine. The reaction mixture obtained was stirred at 80° C. for 4 h, cooled to rt and charged with 0.8 mL of Boc anhydride in 3 mL of THF. Upon completion of the reaction, 1 M HCl was added and the mixture obtained was extracted twice with EtOAc. The combined organic layers obtained were washed with water and brine, dried over sodium sulfate and filtered. From the filtrate obtained solvent was evaporated to dryness. Example 12 Step A product was obtained in the form of a yellow oil.

$^1$H NMR (200MHz, DMSO-d$_6$, δ, ppm, characteristic signals): 1.35 (s, 9H), 3.48 (m, 1H), 5.70 (m, 2H), 6.88 (d, 1H, J=8Hz). TLC: CyH, Rf=0.5.

B. 14-O-{[(1R, 2R, 5R)-5-tert-Butoxycarbonylamino-2-hydroxy-cycloheptylsulfanyl]-acetyl}-mutilin hydrochloride and the (1S, 2S, 5S), (1R, 2R, 5S), (1S, 2S, 5R) diastereomers thereof To a solution of 3.2 mmol of Example 12, Step A product in 20 mL of DCM was added at 0° C. 980 mg of mCPBA (70%) and 350 mg of NaHCO$_3$. The resulting suspension was stirred at rt overnight, then charged with 20% sodium thiosulfate and extracted with EtOAc. The combined organic layers obtained were washed with saturated aqueous NaHCO$_3$, water and brine, dried over sodium sulfate and filtered. The filtrate obtained was concentrated and dried to obtain crude epoxide in the form of a yellowish solid in quantitative yield.

TLC: CyH/EtOAc=1:1, Rf=0.7.

540 mg of the epoxide obtained above was dissolved in 10 mL of toluene, charged with 0.6 mL of thiobenzoic acid and 60 mg of Bu$_4$NCl and the mixture obtained was stirred at 50° C. overnight. Upon completion of the reaction, the mixture obtained was distributed between EtOAc and saturated aqueous NaHCO$_3$, and the aqueous layer obtained was extracted with EtOAc. The combined organic layers obtained were washed with water and brine, dried over sodium sulfate and filtered. The filtrate obtained was concentrated to dryness. A diastereomeric mixture of thiobenzoic acid S-((1R, 2R, 5R)-5-tert-butoxycarbonylamino-2-hydroxy-cycloheptyl)ester and the (1R, 2R, 5S), (1S, 2S, 5S), (1S, 2S, 5R) diastereomers in the form of a a brown oil was obtained.

TLC: CyH/EtOAc=1:1, Rf=0.7.

To a solution of the mixture of thiobenzoic esters obtained above in 10 mL of DCM was added 60 mg of DTT and 0.2 mL of hydrazine monohydrate and the mixture obtained was stirred for 6 h at rt. Upon completion of the reaction, 1 M phosphoric acid was added and the mixture obtained was extracted with EtOAc. The combined organic layers obtained were washed with 1% aqueous NaCl solution, dried over sodium sulfate, filtered, concentrated and immediately used for the next reaction.

To the crude thiol obtained above was added 1.2 g of pleuromutilin tosylate in 6 mL of MTBE, 75 mg benzyltributylammonium chloride and 2.5 mL of 1 M NaOH and the resulting biphasic mixture was stirred over the weekend at rt. The mixture obtained was extracted with EtOAc and water and the organic layer obtained was dried over sodium sulfate, filtered and concentrated. The concentrate obtained was subjected to chromatography (silica, CyH/EtOAc=5/1). 610 mg of a mixture of the Example 12, Step B products was obtained in the form of a colorless foam.

$^1$H NMR (200MHz, DMSO-d$_6$, δ, ppm, characteristic signals): 0.62 (d, 3H, J=6Hz), 0.82 (d, 3H, J=7Hz), 1.06 (s, 3H), 1.36 (s, 12H), 2.40 (bs, 1H), 3.56 (m, 1H), 4.56 (d, 1H, J=6Hz), 4.84 (d, 1H, J=6Hz), 5.05 (m, 2H), 5.56 (d, 1H, J=8Hz), 6.14 (dd, 1H, J=11Hz and 17Hz), 7.6 (m, 1H). MS-ESI– (m/z): 667 (M+HCOO—).

C. 14-O-{[(1R, 2R, 5R)-5-Amino-2-hydroxy-cycloheptylsulfanyl-acetyl}-mutilin hydrochloride and the (1S, 2S, 5S), (1R, 2R, 5S), (1S, 2S, 5R) diastereomers thereof

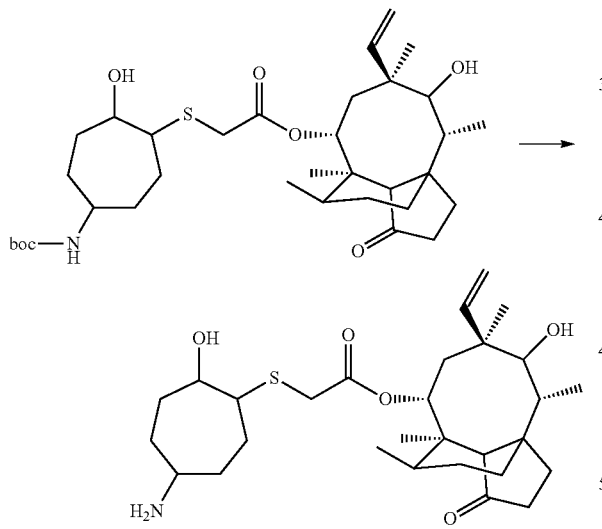

A solution of 600 mg of Example 12 Step B products in 10 mL of DCM was treated with 1 mL of TFA for 7 h at rt. To the mixture obtained 1 M NaOH was added and the resulting mixture was extracted twice with EtOAc. The combined organic layers obtained were washed with saturated aqueous NaHCO$_3$ solution, water and brine, dried over sodium sulfate, filtered and the filtrate obtained was concentrated under reduced pressure. The concentrate obtained was subjected to chromatography (silica, EtOAc/MeOH/NH$_4$OH=75/15/1). 44 mg of a mixture of the Example 12, Step C products was obtained in the form of a colorless foam.

$^1$H NMR (400MHz, DMSO-d$_6$, δ, ppm, characteristic signals): 0.62 (d, 3H, J=6Hz). 0.81 (d, 3H, J=7Hz), 1.05 (s, 3H), 1.36 (s, 3H), 2.40 (bs, 1H), 2.82 (m, 1H), 2.99 (m, 1H), 3.64 (m, 1H), 4.50 (m, 1H), 5.05 (m, 2H), 5.54 (d, 1H, J=8Hz), 6.13 (m, 1H). MS-ESI+ (m/z): 522 (M+H), MS-ESI– (m/z): 520 (M–H). TLC: EtOAc/MeOH=9:1+1% NH$_4$OH, Rf=0.3.

D. 14-O-{[(1R, 2R, 5R)-5-Amino-2-hydroxy-cycloheptylsulfanyl]-acetyl}-mutilin hydrochloride hydrochloride and the (1S, 2S, 5S), (1R, 2R, 5S), (1S, 2S, 5R) diastereomers thereof

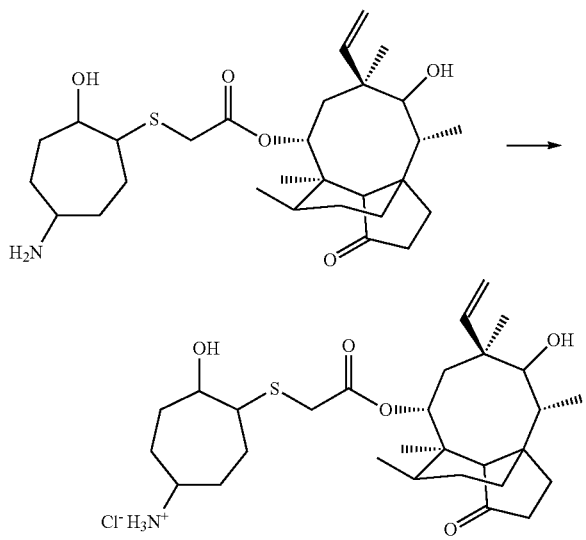

To a solution of 40 mg of Example 12, Step C products in 1 mL of dioxane was added 0.12 mL of 1 M HCl. The mixture obtained was stirred at rt for 10 minutes the solution obtained was lyophilized. Example 12, Step D products in the form of a colorless foam was obtained in quantitative yield.

MS-ESI+ (m/z): 522 (M+). TLC: EtOAc/MeOH=9:1+1% NH$_4$OH, Rf=0.3.

EXAMPLE 13

14-O-{[(1R, 2S, 3S, 5R, 6S)-6-Amino-2-hydroxy-bicyclo[3.2.0]hept-3-ylsulfanyl]-acetyl}-mutilin hydrochloride and the (1S, 2R, 3R, 5S, 6R) diastereomers thereof A. (1S, 5R, 6S)-Bicyclo[3.2.0]hept-2-en-6-yl-(2,4-dimethoxy-benzyl)-amine and the (1R, 5S, 6R) diasteromer thereof

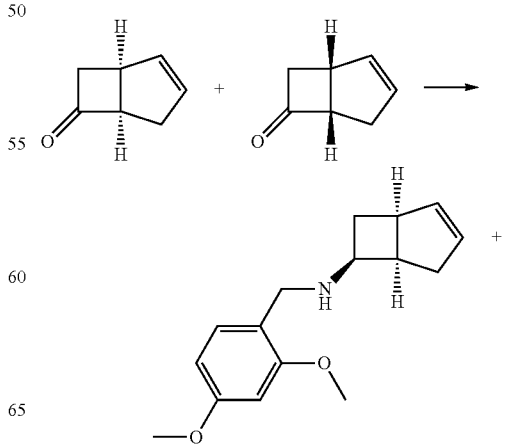

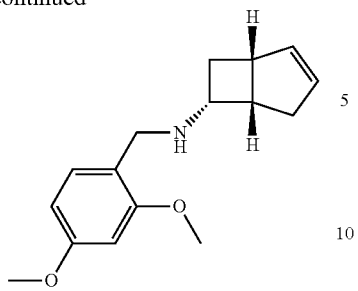

To a solution of 10 g of cis bicyclo[3.2.0]hept-2-en-6-one in 100 mL of dry DCM was added 185 mmol 2,4-dimethoxybenzylamine, 8 mL of acetic acid and 27 g of sodium triacetoxyborohydride at rt and the resulting reaction mixture was stirred overnight. To the mixture obtained EtOAc was added, the mixture obtained was washed with 1 N NaOH and the aqueous phase obtained was extracted with EtOAc. The combined organic layers obtained were washed with water and brine, dried and solvent was evaporated. The evaporation residue obtained was subjected to chromatography (silica, EtOAc/MeOH=5/1). 21.64 g of Example 13, Step A products was obtained in the form of a yellow oil.

$^1$H-NMR (200 MHz, DMSO-$d_6$, δ, ppm, characteristic signals): 1.70 (m, 1H), 2.10-2.70 (m, 4H), 2.95 (m, 2H), 3.40 (m, 2H), 3.73, 3.76 (2s, 6H), 5.77 (m, 2H), 6.40-7.20 (m, 3H). MS-ESI+ (m/z): 260 (M+H). TLC: EtOAc/MeOH=1:1, Rf=0.5.

B. tert-Butyl (1S, 5R, 6S)-Bicyclo[3.2.0]hept-2-en-6-yl-(2,4-dimethoxy-benzyl)-carbamate and the (1R, 5S, 6R) diastereomer thereof

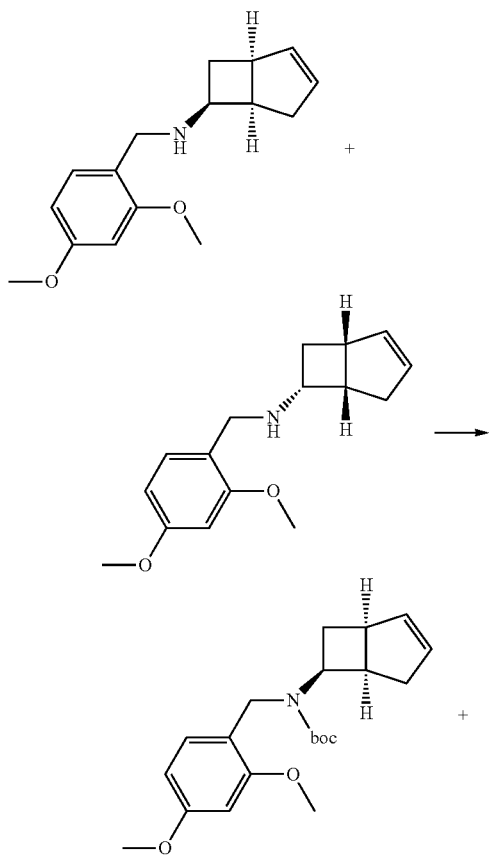

-continued

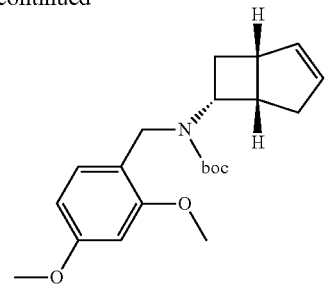

To a solution of 23.54 g of Example 13 Step A products in 150 mL of DCM was added 22 mL of Boc-anhydride and 25.3 mL of TEA and the resulting reaction mixture was stirred at rt overnight. From the mixture obtained solvent was evaporated and the evaporation residue obtained was charged with EtOAc. The mixture obtained was washed with 1 M HCl, the organic layer obtained was dried over sodium sulfate and solvent was evaporated to dryness. 30.46 g of Example 13, Step B products in the form of a yellow solid was obtained.

$^1$H-NMR (200 MHz, DMSO-$d_6$, δ, ppm, characteristic signals): 1.36 (s, 9H), 1.58 (m, 1H), 2.20-2.45 (m, 3H), 2.90 (m, 1H), 3.07 (m, 1H), 3.72, 3.75 (2s, 6H), 4.10 (d, 1H J=17Hz), 4.42 (m, 1H), 4.53 (d, 1H, J=17Hz), 5.73 (m, 1H), 5.83 (m, 1H), 6.40-6.84 (m, 3H). MS-ESI+ (m/z): 360 (M+H). TLC: CyH/EtOAc=3:1, Rf=0.65.

C. tert-Butyl (R)-(2,4-Dimethoxy-benzyl)-(1R, 3S, 6R, 7S)-3-oxa-tricyclo[4.2.0*2,4*]oct-7-yl-carbamate and the (1S, 3R, 6S, 7R) diastereomer thereof

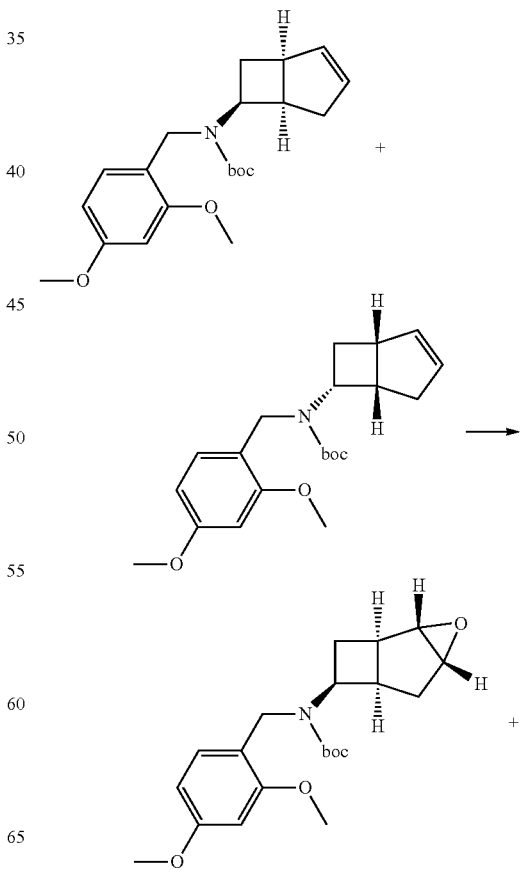

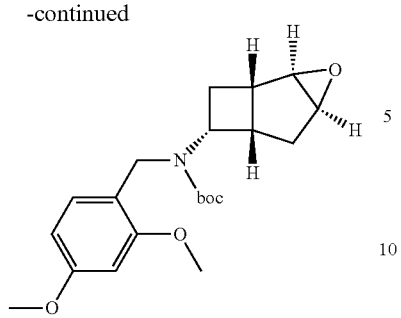

10.4 g of mCPBA (70%) was added at 0° C. to a solution of 15.2 g of Example 13, Step B products in 100 ml of DCM. To the mixture obtained 5.3 g of NaHCO₃ was added and the mixture obtained was stirred at rt for 2 days. The mixture obtained was charged with 20% sodium thiosulfate, stirred and extracted with EtOAc. The combined organic layers obtained were washed with saturated NaHCO₃ solution, water and brine, dried over sodium sulfate and solvent was evaporated. The crude evaporation residue obtained was dried under HV. 16.9 g of Example 13 Step C products in the form of a brown oil was obtained.

MS-ESI+ (m/z): 376 (M+H). TLC: CyH/EtOAc=2:1, Rf=0.5.

D. Thiobenzoic acid S-{[(1R, 2S, 3S, 5R, 6S)-6-[tert-butoxycarbonyl-(2,4-dimethoxy-benzyl)-amino]-2-hydroxy-bicyclo[3.2.0]hept-3-yl}ester and the (1S, 2R, 3R, 5S, 6R) diasteromer thereof

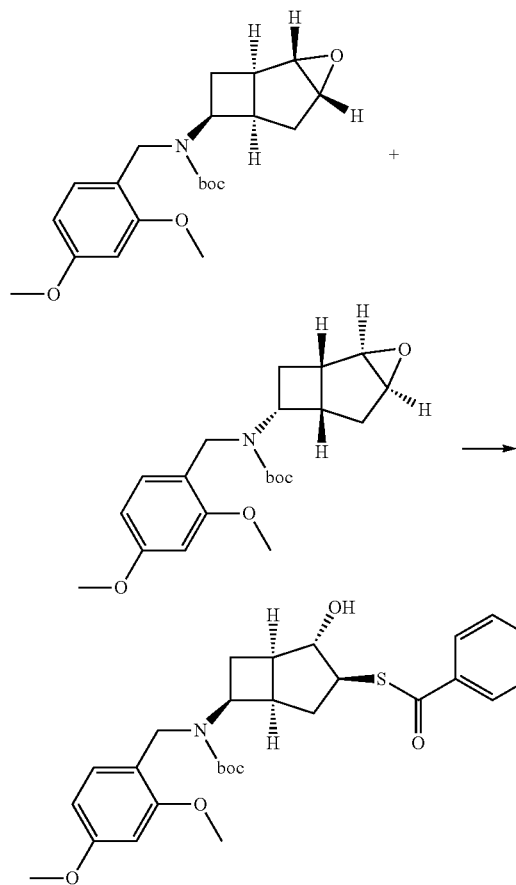

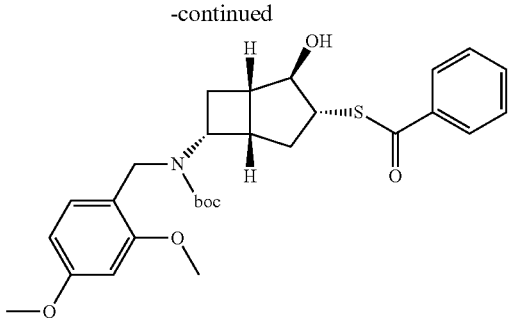

10.5 mL of thiobenzoic acid was added dropwise to a solution of 16.9 g of epoxide from Example 13, Step C in 100 mL of dry toluene containing 1 g of Bu₄NCl. The reaction mixture obtained was stirred for 20 h at rt and for 20 h at 55° C. To the mixture obtained saturated NaHCO₃ solution was added and after 20 min the reaction mixture was charged with EtOAc. The phases obtained were separated and the organic phase obtained was washed 3 times with saturated aqueous NaHCO₃ solution, dried and solvent was evaporated. The evaporation residue obtained was subjected to chromatography (silica, CyH/EtOAc=4:1). 6.49 g of Example 13 Step D products in the form of an oil was obtained.

¹H-NMR (200 MHz, DMSO-d₆, δ, ppm, characteristic signals): 1.37 (s, 9H), 3.72, 3.77 (2s, 6H), 3.86 (m, 2H), 4.21 (d, 1H J=17Hz), 4.38 (d, 1H, J=17Hz), 5.17 (d, 1H, J=5Hz), 6.40-6.95 (m, 3H), 7.50-7.95 (m, 5H). MS-ESI− (m/z): 558 (M+HCOO⁻), MS-ESI+ (m/z): 514 (M+H). TLC: CyH/EtOAc=2:1, Rf=0.35.

E. 14-O-{[(1R, 2S, 3S, 5R, 6S)-6-[tert-butoxycarbonyl-(2,4-dimethoxy-benzyl)-amino]-2-hydroxy-bicyclo[3.2.0]hept-3-ylsulfanyl]-acetyl}-mutilin and the (1S, 2R, 3R, 5S, 6R) diastereomers thereof

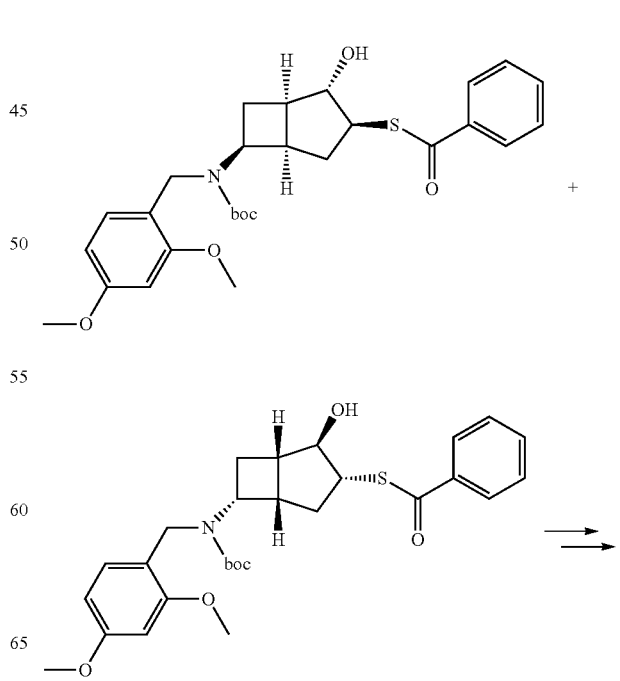

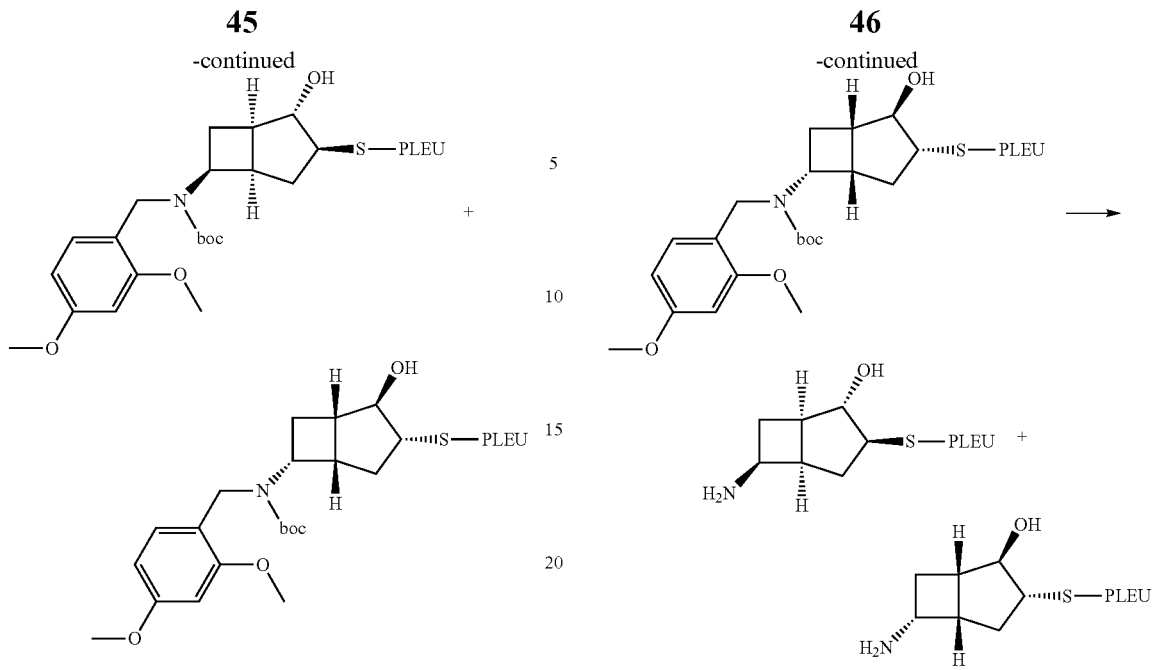

To a solution of 6.49 g of Step D products from above in 20 mL of DCM was added at 0° C. 649 mg of DTT and 0.9 mL of hydrazine monohydrate and the solution obtained was stirred for 2 h at rt. After addition of 1 M $H_3PO_4$ the mixture obtained was diluted with DCM and the layers were separated. The organic layer obtained was washed 3 times with 1 M $H_3PO_4$, once with 1% NaCl solution, dried over sodium sulfate and solvent was evaporated to dryness.

MS-ESI+ (m/z): 410 (M+H). MS-ESI− (m/z): 408 (M−H). TLC: CyH/EtOAc=1:1, Rf=0.4.

The evaporation residue obtained was dissolved in 50 mL of dry acetonitrile and 1.7 mL of DBN and 6.06 g of pleuromutilin tosylate were added. The resulting mixture was stirred for 2 days at rt, charged with EtOAc, the phases obtained were separated and the organic phase obtained was washed with brine, dried and the solvent was evaporated. The evaporation residue obtained was subjected to chromatography (silica, CyH/EtOAc=2:1). 4.98 g of Example 13 Step E products in the form of a white foam was obtained.

$^1$H-NMR (400 MHz, DMSO-$d_6$, δ, ppm, characteristic signals): 0.65 (d, 3H, J=8Hz), 0.83 (d, 3H, J=7Hz), 1.06 (s, 3H), 1.37 (s, 12H), 2.41 (bs, 1H), 2.93 (m, 1H), 3.05 (m, 1H), 3.44 (t, 1H, J=4Hz), 3.70 (t, 2H, J=5Hz), 3.80 (m, 1H), 4.15 (d, 1H, J=12Hz), 4.37 (d, 1H, J=12Hz), 4.51 (d, 1H, J=7Hz), 5.07 (m, 2H), 5.56 (d, 1H, J=8Hz), 6.15 (m, 1H), 6.45-6.90 (m, 3H). MS-ESI+ (m/z): 770 (M+H). TLC: CyH/EtOAc=1:2, Rf=0.55.

F. 14-O-{[(1R, 2S, 3S, 5R, 6S)-6-Amino-2-hydroxy-bicyclo[3.2.0]hept-3-ylsulfanyl]-acetyl}-mutilin and the (1S, 2R, 3R, 5S, 6R) diastereomers thereof

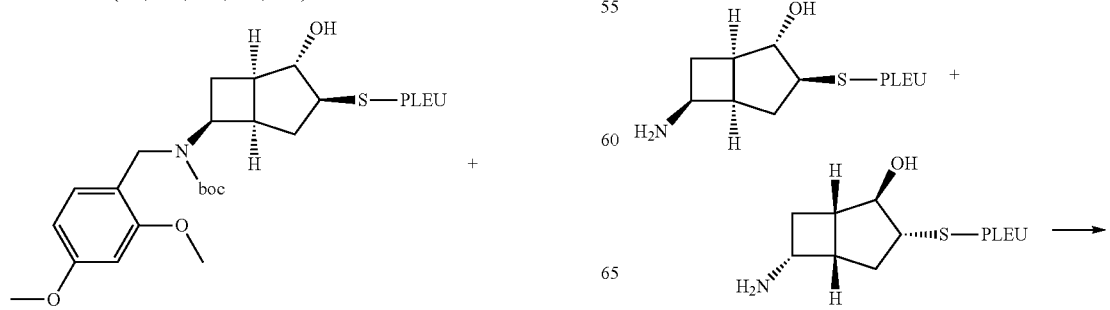

To a solution of 4.98 g of Example 13 Step E products from above in 20 mL of DCM was added at 0° C. 2.5 mL of TFA, 0.3 mL of thioanisole and 0.13 mL of methanesulfonic acid and the solution obtained was stirred for 6 h at rt. The reaction mixture obtained was added dropwise under stirring to cold DIPE and the resulting precipitate was filtered and dried. The solid was taken up in EtOAc, the pH adjusted to 12 with 5 M NaOH and the aqueous layer obtained was extracted with EtOAc. The combined organic layers obtained were dried over sodium sulfate and solvent was evaporated to dryness. 1.98 g of free base Example 13, Step F products in the form of a colorless foam was obtained.

$^1$H-NMR (200 MHz, DMSO-$d_6$, δ, ppm, characteristic signals): 0.64 (d, 3H, J=6Hz), 0.83 (d, 3H, J=7Hz), 1.06 (s, 3H), 1.36 (s, 3H), 2.41 (bs, 1H), 2.77 (m, 1H), 3.04 (m, 1H), 3.28 (m, 1H), 3.41 (m, 3H), 3.70 (m, 1H), 4.54 (bs, 1H), 5.06 (m, 2H), 5.56 (d, 1H, J=8Hz), 6.14 (dd, 1H, J=11 and 18Hz). MS-ESI+ (m/z): 520 (M+H). TLC: EtOAc/MeOH=10:1+1% $NH_4OH$, Rf=0.4.

G. 14-O-{[(1R, 2S, 3S, 5R, 6S)-6-Amino-2-hydroxy-bicyclo[3.2.0]hept-3-ylsulfanyl]-acetyl}-mutilin hydrochloride and the (1S, 2R, 3R, 5S, 6R) diastereomers thereof

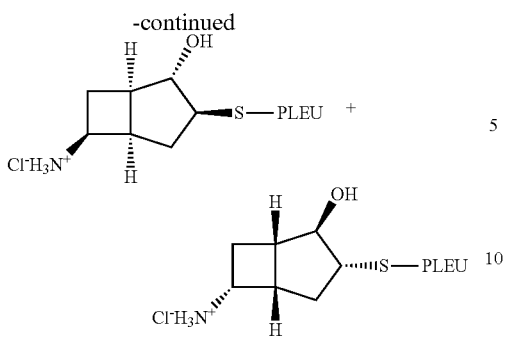

To a solution of 300 mg of free base Example 13, Step F products in 1 mL of dioxane was added 0.9 mL of 1 M HCl. The mixture obtained was stirred at rt for 15 minutes and the solution obtained was lyophilized. 301 mg of the Example 13 title compounds in the form of a colorless foam was obtained.

$^1$H-NMR (200 MHz, DMSO-$d_6$, δ, ppm, characteristic signals): 0.64 (d, 3H, J=6Hz), 0.83 (d, 3H, J=7Hz), 1.06 (s, 3H), 1.37 (s, 3H), 2.41 (bs, 1H), 2.92 (bm, 2H), 3.47 (m, 3H), 3.74 (m, 1H), 4.56 (bd, 1H), 5.10 (m, 3H), 5.56 (d, 1H, J=8Hz), 6.14 (dd, 1H, J=11 and 18Hz). MS-ESI− (m/z): 554 (M+Cl$^-$), 564 (M+HCOO$^-$), MS-ESI+ (m/z): 520 (M+H).

EXAMPLE 14

14-O-{[(1R, 2S, 3S, 5R, 6S)-6-Formylamino-2-hydroxy-bicyclo[3.2.0]hept-3-ylsulfanyl]-acetyl}-mutilin and the (1S, 2R, 3R, 5S, 6R) diastereomers thereof

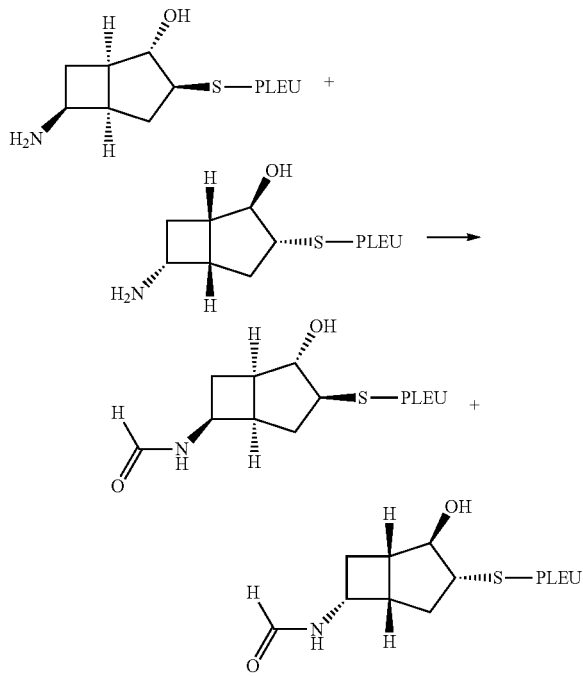

To a solution of 0.1 mL acetic formic anhydride in DCM was added 71 mg of DMAP and 300 mg of free base from Example 13, Step F. The mixture obtained was stirred at rt for 2 days, the solution obtained was charged with EtOAc, the mixture obtained was washed with brine, dried and solvent was evaporated. The evaporation residue obtained was subjected to chromatography (silica, CyH/EtOAc=1:10-EtOAc). 100 mg of the Example 14 title compounds in the form of a colorless solid was obtained.

$^1$H-NMR (200 MHz, DMSO-$d_6$, δ, ppm, characteristic signals): 0.63 (d, 3H, J=6Hz), 0.83 (d, 3H, J=7Hz), 1.05 (s, 3H), 1.37 (s, 3H), 2.41 (bs, 1H), 2.80-3.10 (m, 2H), 3.41 (m, 3H), 3.73 (m, 1H), 4.20 (m, 1H), 4.54 (d, 1H, J=6Hz), 5.07 (m, 3H), 5.56 (d, 1H, J=8Hz), 6.14 (dd, 1H, J=11 and 18Hz), 7.89 (s, 1H), 8.04 (d, 1H, J=7 Hz). MS-ESI− (m/z): 592 (M+HCOO$^-$), MS-ESI+ (m/z): 548 (M+H). TLC: toluene/EtOAc=1:10, Rf=0.2.

EXAMPLE 15

14-O-{[(1R, 2S, 3S, 5R, 6S)-6-(2-Amino-acetylamino)-2-hydroxy-bicyclo[3.2.0]hept-3-ylsulfanyl]-acetyl}-mutilin and the (1S, 2R, 3R, 5S, 6R) diastereomers thereof A. 14-O-{[(1R, 2S, 3S, 5R, 6S)-6-(2-tert-Butoxycarbonylamino-acetylamino)-2-hydroxy-bicyclo[3.2.0]hept-3-ylsulfanyl]-acetyl}-mutilin and the (1S, 2R, 3R, 5S, 6R) diastereomers thereof

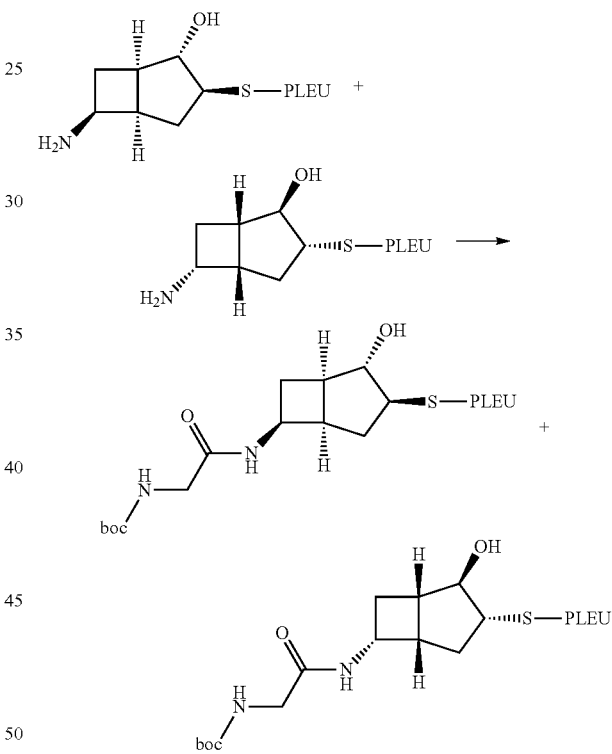

To a solution of 102 mg of Boc-glycine in dry DCM was added 78 mg of HOBT, 71 mg of DMAP, 111 mg of EDC and the resulting mixture was stirred for 30 min at rt. To the mixture obtained the 300 mg of free base from Example 13 Step F was added. The mixture obtained was stirred at rt for 2 days, the solution obtained was charged with EtOAc, the phases obtained were separated and the organic phase obtained was washed with brine, dried and solvent was evaporated. The evaporation residue obtained was subjected to chromatography (silica, toluene/EtOAc=1:20-EtOAc). 196 mg of the Example 15, Step A products in the form of a colorless foam was obtained.

$^1$H-NMR (200 MHz, DMSO-$d_6$, δ, ppm, characteristic signals): 0.63 (d, 3H, J=5Hz), 0.83 (d, 3H, J=7Hz), 1.06 (s, 3H), 1.37 (s, 12H), 2.41 (bs, 1H), 2.99 (m, 1H), 3.04 (m, 1H), 3.45 (m, 5H), 3.74 (m, 1H), 4.18 (m, 1H), 4.54 (d, 1H, J=6Hz), 5.07 (m, 3H), 5.56 (d, 1H, J=8Hz), 6.14 (dd, 1H, J=10 and 17Hz), 6.92 (m, 1H), 7.76 (d, 1H, J=8Hz). MS-ESI− (m/z): 721 (M+HCOO−), MS-ESI+ (m/z): 677 (M+H). TLC: toluene/EtOAc=1:10, Rf=0.25.

B. 14-O-{[(1R, 2S, 3S, 5R, 6S)-6-(2-Amino-acetylamino)-2-hydroxy-bicyclo[3.2.0]hept-3-ylsulfanyl]-acetyl}-mutilin and the (1S, 2R, 3R, 5S, 6R) diastereomers thereof

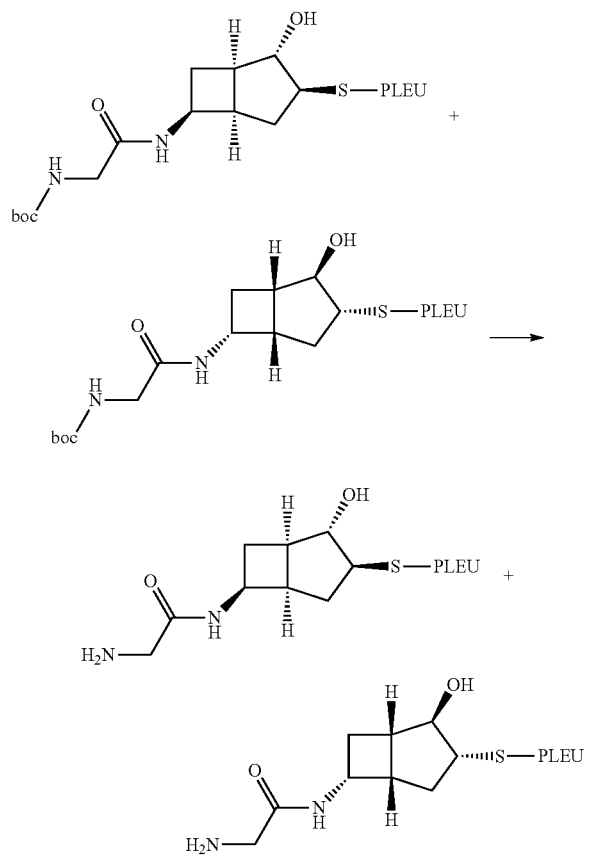

To a solution of 196 mg of the Example 15 Step A products from above in 3 mL of DCM was added 0.3 mL of TFA and the mixture obtained was stirred for 6 h at rt. To the mixture obtained EtOAc and 1 M NaOH were added, the phases obtained were separated and the aqueous phase obtained was extracted with EtOAc. The combined organic layers obtained were washed with water and brine, dried and solvent was evaporated. The evaporation residue obtained was subjected to chromatography (silica, EtOAc/MeOH/NH$_4$OH=90:3:1). 68 mg of the free base of Example 15, Step B products was obtained in the form of a colorless foam.

$^1$H-NMR (200 MHz, DMSO-d$_6$, δ, ppm, characteristic signals): 0.64 (d, 3H, J=6Hz), 0.83 (d, 3H, J=7Hz), 1.06 (s, 3H), 1.37 (s, 3H), 2.41 (bs, 1H), 2.92 (m, 1H), 3.05 (m, 3H), 3.40 (m, 3H), 3.76 (m, 1H), 4.22 (m, 1H), 4.54 (d, 1H, J=5Hz), 5.06 (m, 3H), 5.56 (d, 1H, J=8Hz), 6.15 (dd, 1H, J=11 and 18Hz), 7.95 (d, 1H, J=8Hz). MS-ESI− (m/z): 621 (M+HCOO−), MS-ESI+ (m/z): 577 (M+H). TLC: EtOAc/MeOH=10:1+1% NH$_4$OH, Rf=0.2.

C. 14-O-{[(1R, 2S, 3S, 5R, 6S)-6-(2-Amino-acetylamino)-2-hydroxy-bicyclo[3.2.0]hept-3-ylsulfanyl]-acetyl}-mutilin hydrochloride and the (1S, 2R, 3R, 5S, 6R) diastereomers thereof

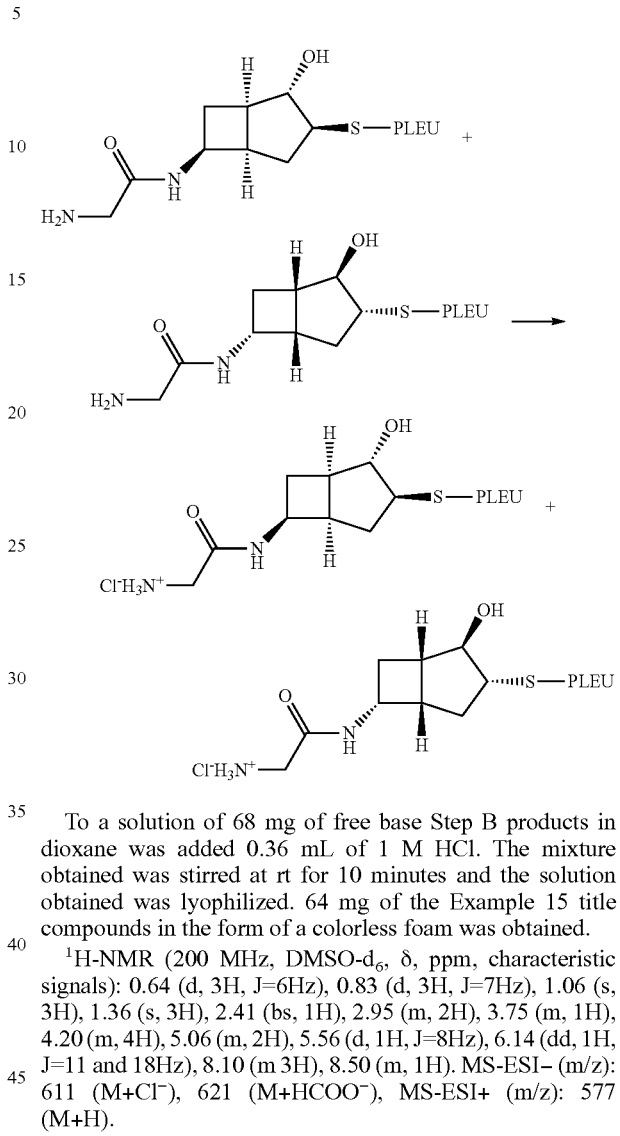

To a solution of 68 mg of free base Step B products in dioxane was added 0.36 mL of 1 M HCl. The mixture obtained was stirred at rt for 10 minutes and the solution obtained was lyophilized. 64 mg of the Example 15 title compounds in the form of a colorless foam was obtained.

$^1$H-NMR (200 MHz, DMSO-d$_6$, δ, ppm, characteristic signals): 0.64 (d, 3H, J=6Hz), 0.83 (d, 3H, J=7Hz), 1.06 (s, 3H), 1.36 (s, 3H), 2.41 (bs, 1H), 2.95 (m, 2H), 3.75 (m, 1H), 4.20 (m, 4H), 5.06 (m, 2H), 5.56 (d, 1H, J=8Hz), 6.14 (dd, 1H, J=11 and 18Hz), 8.10 (m 3H), 8.50 (m, 1H). MS-ESI− (m/z): 611 (M+Cl−), 621 (M+HCOO−), MS-ESI+ (m/z): 577 (M+H).

EXAMPLE 16

14-O-{[(1R, 2S, 3S, 5R, 6S)-6-Cyclopropylamino-2-hydroxy-bicyclo[3.2.0]hept-3-ylsulfanyl]-acetyl}-mutilin hydrochloride and the (1S, 2R, 3R, 5S, 6R) diastereomers thereof A. (1S, 5R, 6S)-Bicyclo[3.2.0]hept-2-en-6-yl-cyclopropyl-amine and the (1R, 5S, 6R) diasteromer thereof

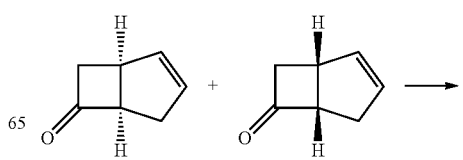

-continued

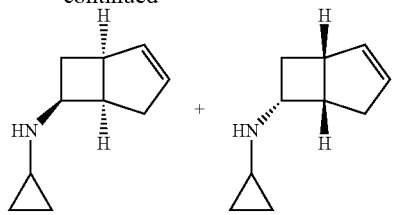

To a solution of 5 g of cis bicyclo[3.2.0]hept-2-en-6-one in 50 mL of dry DCM was added 3.22 mL of cyclopropylamine, 2.65 mL of acetic acid and 13.7 g of sodium triacetoxyborohydride at rt and after 18 h solvent was evaporated. To the evaporation residue obtained EtOAc was added, the mixture obtained was washed with 1 N NaOH and the aqueous phase obtained was extracted with EtOAc. The combined organic layers obtained were washed with water and brine, dried and solvent was evaporated. The evaporation residue obtained was subjected to chromatography (silica, EtOAc/MeOH=5/1). 4.02 g of Example 16, Step A products was obtained in the form of a colorless oil.

$^1$H-NMR (200 MHz, DMSO-d$_6$, δ, ppm, characteristic signals): 0.05-0.40 (m, 4H), 1.29 (m, 1H), 1.91 (m, 1H), 2.10-2.70 (m, 3H), 2.97 (m, 2H), 3.46 (m, 1H), 5.76 (m, 2H). MS-ESI+ (m/z): 150 (M+H). TLC: CyH/EtOAc=4:1, Rf=0.35.

B. tert-Butyl (1S, 5R, 6S)-Bicyclo[3.2.0]hept-2-en-6-yl-cyclopropyl-carbamate and the (1R, 5S, 6R) diasteromer thereof

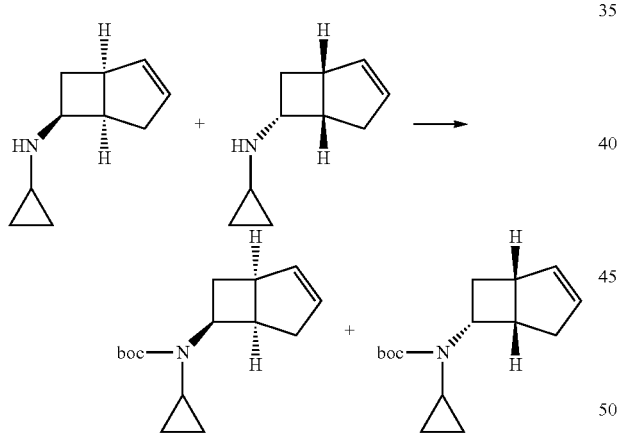

To a solution of 4.02 mg of Example 16, Step A products in 100 mL of DCM was added 6.2 g of Boc-anhydride and 7.5 mL of TEA and the resulting reaction mixture was stirred at rt overnight. The mixture obtained was evaporated and the evaporation residue obtained was charged with EtOAc and the mixture obtained was washed with 1 M HCl. Phases obtained were separated, the organic layer obtained was dried over sodium sulfate and solvent was evaporated to dryness. 7.14 g of Example 16, Step B products in the form of a colorless solid was obtained.

$^1$H-NMR (200 MHz, DMSO-d$_6$, δ, ppm, characteristic signals): 0.30-0.80 (m, 4H), 1.37 (s, 9H), 2.00-2.60 (m, 5H), 2.90 (m, 1H), 3.07 (m, 1H), 4.14 (q, 1H, J=9Hz), 5.80 (m, 2H).

TLC: CyH/EtOAc=4:1, Rf=0.75.

C. tert-Butyl (R)-Cyclopropyl-(1R, 3S, 6R, 7S)-3-oxa-tricyclo[4.2.0*2,4*]oct-7-yl-carbamate and the (1S, 3R, 6S, 7R) diasteromer thereof

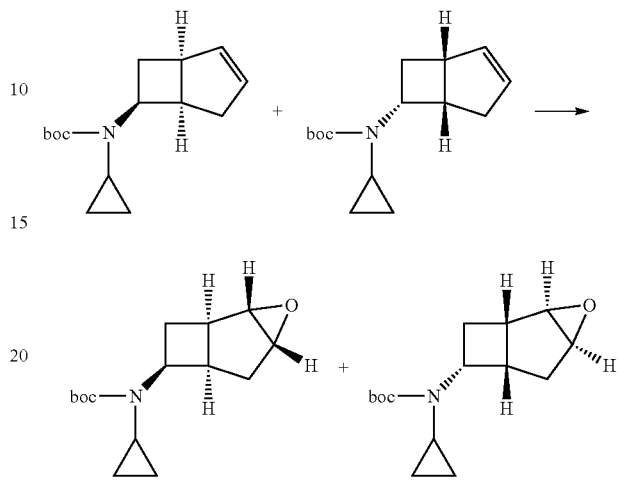

7.05 g of mCPBA (70%) was added at 0° C. to a solution of 7.14 g of Example 16, Step B products in 100 ml of DCM. To the mixture obtained 3.6 g of NaHCO$_3$ was added and the mixture obtained was stirred at rt for 3 days. The mixture obtained was charged with 20% sodium thiosulfate, and extracted with EtOAc. The combined organic layers obtained were washed with saturated aqueous NaHCO$_3$ solution, water and brine, dried over sodium sulfate and solvent was evaporated. The crude evaporation residue obtained was dried under HV. 5.73 g of Example 16, Step C products in the form of a colorless solid was obtained.

MS-ESI+ (m/z): 266 (M+H). TLC: CyH/EtOAc=2:1, Rf=0.45.

D. Thiobenzoic acid S-{[(1R, 2S, 3S, 5R, 6S)-6-(tert-butoxycarbonyl-cyclopropyl-amino)-2-hydroxy-bicyclo[3.2.0]hept-3-yl}ester and the (1S, 2R, 3R, 5S, 6R) diasteromer thereof

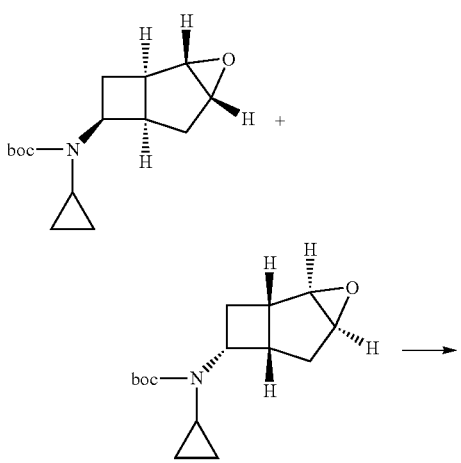

-continued

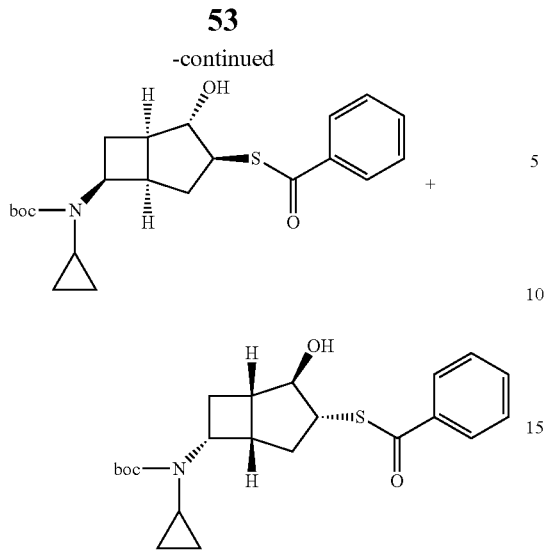

20.1 mL of thiobenzoic acid was added dropwise to a solution of 5.73 g of epoxide from Example 16, Step C in 50 mL of dry toluene containing 478 mg of Bu$_4$NCl. The reaction mixture obtained was stirred for 3 days at rt. To the mixture obtained saturated aqueous NaHCO$_3$ solution was added and after 15 min the mixture obtained was charged with EtOAc, the phases obtained were separated and the organic phase was washed 3 times with saturated NaHCO$_3$ solution, dried and solvent was evaporated. The evaporation residue obtained was subjected to chromatography (silica, CyH/EtOAc=5:1). 5.20 g of Example 16 Step D products was obtained.

$^1$H-NMR (200 MHz, DMSO-d$_6$, δ, ppm, characteristic signals): 0.42 (m, 2H), 0.67 (m, 2H), 1.36 (s, 9H), 1.72 (m, 1H), 2.25-2.50 (m, 5H), 3.10 (m, 1H), 3.80 (m, 2H), 3.97 (m, 1H), 5.71 (d, 1H, J=5Hz), 7.50-7.95 (m, 5H). MS-ESI− (m/z): 448 (M+HCOO$^-$). TLC: CyH/EtOAc=3:1, Rf=0.25.

E. 14-O-{[(1R, 2S, 3S, 5R, 6S)-6-[tert-butoxycarbonyl-cyclopropyl-amino]-2-hydroxy-bicyclo[3.2.0]hept-3-ylsulfanyl]-acetyl}-mutilin and the (1S, 2R, 3R, 5S, 6R) diastereomers thereof

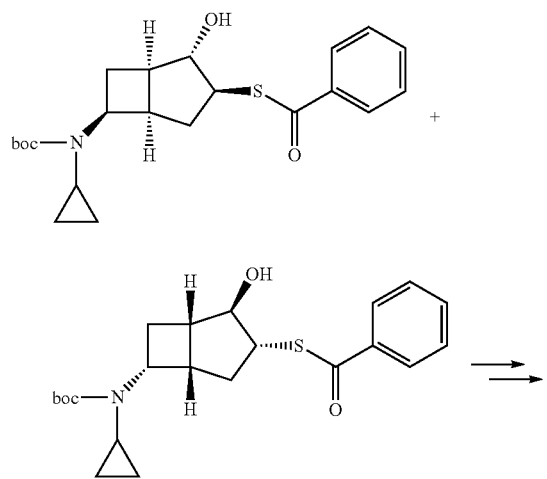

-continued

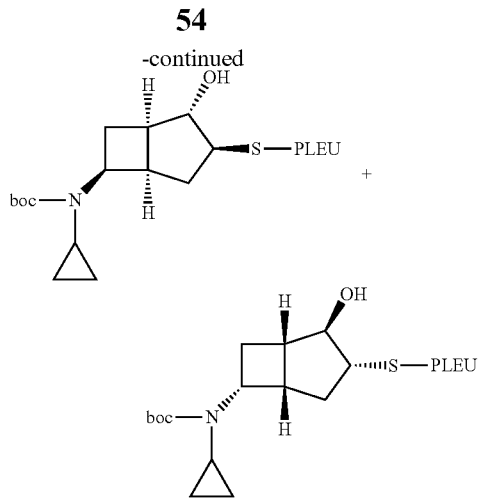

To a solution of 5.20 g of Example 16, Step D products in 50 mL of DCM was added at 0° C. 520 mg of DTT and 0.94 mL of hydrazine monohydrate and the solution obtained was stirred for 6 h at rt. To the mixture obtained was added 1 M H$_3$PO$_4$, the mixture obtained was diluted with DCM and the layers obtained were separated. The organic layer obtained was washed 3 times with 1 M H$_3$PO$_4$, once with 1% NaCl solution, dried over sodium sulfate and solvent was evaporated.

MS-ESI+ (m/z): 300 (M+H). TLC: CyH/EtOAc=3:1, Rf=0.2.

The evaporation residue obtained was dissolved in 50 mL of dry acetonitrile and 1.7 mL of DBN and 6.20 g of pleuromutilin tosylate were added. The resulting mixture was stirred overnight at rt, charged with EtOAc and washed with brine. The aqueous phase obtained was extracted with EtOAc and the combined organic layers obtained were washed twice with brine, dried and evaporated. The evaporation residue obtained was subjected to chromatography (silica, CyH/EtOAc=1:1). 4.60 g of Example 16, Step E products was obtained in the form of a white foam.

$^1$H-NMR (400 MHz, DMSO-d$_6$, δ, ppm, characteristic signals): 0.36 (m, 1H), 0.46 (m, 1H), 0.56-0.72 (m, 5H), 0.83 (d, 3H, J=7Hz), 1.06 (s, 3H), 1.37 (s, 12H), 2.41 (bs, 1H), 2.97 (m, 1H), 3.08 (m, 1H), 3.43 (m, 1H), 3.70-3.80 (m, 2H), 4.50 (d, 1H, J=6Hz), 4.99 (bs, 1H), 5.06 (m, 2H), 5.56 (d, 1H, J=8Hz), 6.14 (m, 1H). MS-ESI− (m/z): 704 (M+HCOO$^-$), MS-ESI+ (m/z): 660 (M+H). TLC: CyH/EtOAc=1:2, Rf=0.5.

F. 14-O-{[(1R, 2S, 3S, 5R, 6S)-6-Cyclopropylamino-2-hydroxy-bicyclo[3.2.0]hept-3-ylsulfanyl]-acetyl}-mutilin and the (1S, 2R, 3R, 5S, 6R) diastereomers thereof

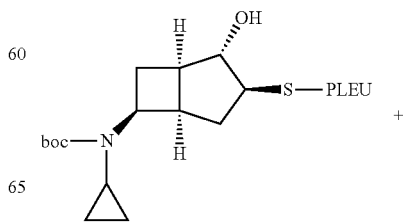

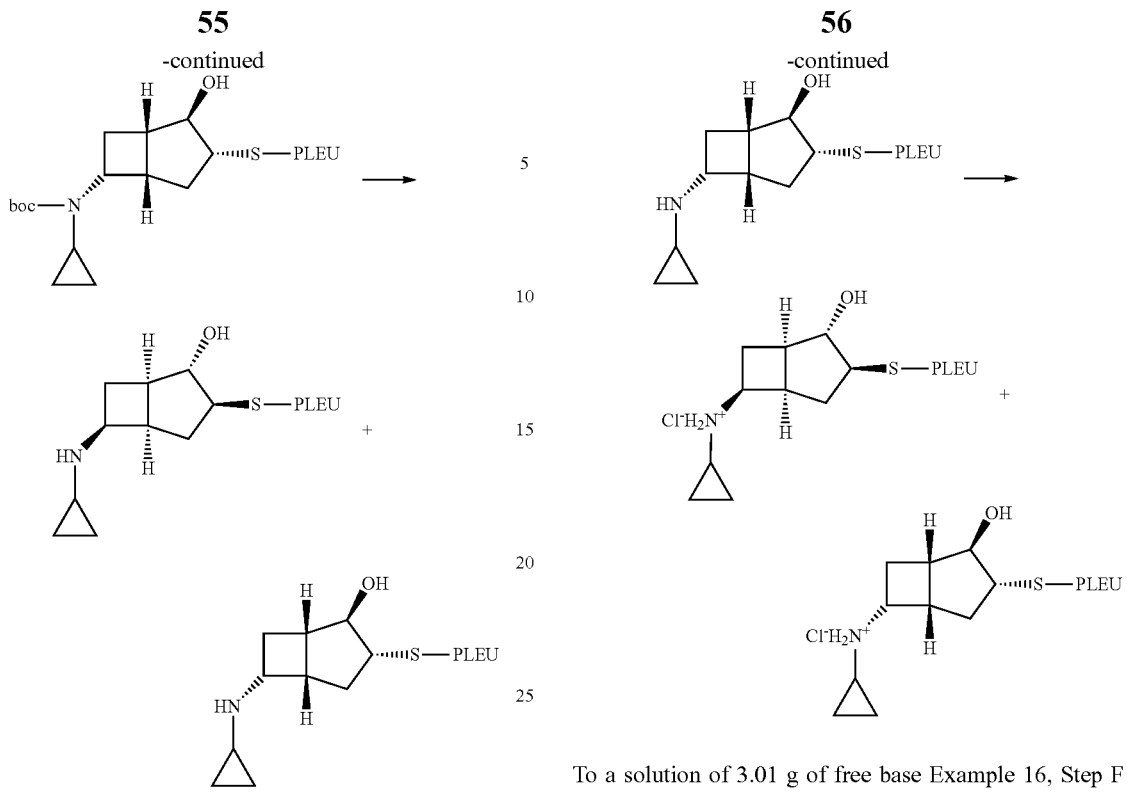

To a solution of 4.60 g of Example 16, Step E products from above in 30 mL of DCM was added at 0° C. 6.9 mL of TFA. The resulting mixture was stirred for 6 h at rt, charged with EtOAc and saturated aqueous NaHCO₃ solution. The aqueous phase obtained was extracted with EtOAc and the combined organic layers obtained were washed twice with water and with brine, dried and solvent was evaporated. The evaporation residue obtained was subjected to chromatography (silica, EtOAc/MeOH/NH₄OH=100:5:1). 3.00 g of Example 16 Step F products was obtained in the form of a colorless foam.

$^1$H-NMR (200 MHz, DMSO-d$_6$, δ, ppm, characteristic signals): 0.10-0.35 (m, 4H), 0.64 (d, 3H, J=6Hz), 0.83 (d, 3H, J=7Hz), 1.06 (s, 3H), 1.36 (s, 3H), 2.41 (bs, 1H), 2.84 (m, 1H), 3.02 (m, 1H), 3.20 (m, 1H), 3.58 (m, 1H), 4.53 (d, 1H, J=6 Hz), 5.04 (m, 3H), 5.56 (d, 1H, J=8Hz), 6.15 (m, 1H). MS-ESI+ (m/z): 560 (M+H). TLC: EtOAc/MeOH=10:1+1% NH₄OH, Rf=0.6.

G. 14-O-{[(1R, 2S, 3S, 5R, 6S)-6-Cyclopropylamino-2-hydroxy-bicyclo[3.2.0]hept-3-ylsulfanyl]-acetyl}-mutilin hydrochloride and the (1S, 2R, 3R, 5S, 6R) diastereomers thereof

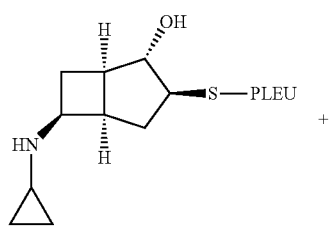

To a solution of 3.01 g of free base Example 16, Step F products in 10 mL of dioxane was added 8.06 mL of 1 M HCl. The mixture obtained was stirred at rt for 10 minutes and the solution obtained was lyophilized. The Example 16 title compounds in the form of a colorless foam were obtained in quantitative yield.

$^1$H-NMR (200 MHz, DMSO-d$_6$, δ, ppm, characteristic signals): 0.64 (m, 5H), 0.83 (m, 5H), 1.06 (s, 3H), 1.37 (s, 3H), 2.42 (bs, 1H), 2.94 (m, 2H), 3.73 (m, 2H), 4.57 (d, 1H, J=5Hz), 5.10 (m, 3H), 5.56 (d, 1H, J=7Hz), 6.15 (dd, 1H, J=11 and 18Hz). MS-ESI− (m/z): 594 (M+Cl⁻), 604 (M+HCOO⁻), MS-ESI+ (m/z): 560 (M+H).

EXAMPLE 17

14-O-{[4-Acetylamino-6a-hydroxy-octahydropentalen-1-ylsulfanyl]-acetyl}-mutilin

A. N-(4-Iodo-octahydropentalen-1-yl)-acetamide

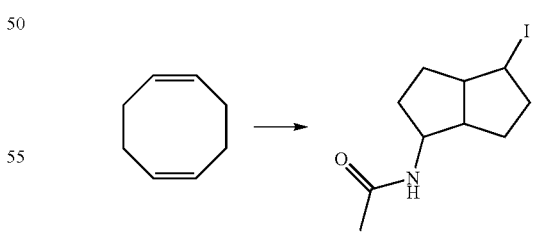

To a solution of 10.33 g of iodine in 200 mL of acetonitrile was added at 0° C. 10 mL of cis,cis-1,5-cyclooctadiene and the resulting solution was stirred at rt overnight (Uemura, S. et al, J. Org. Chem. 1983, 48, 270-273). From the mixture obtained solvent was evaporated and the evaporation residue obtained was taken up in EtOAc. The mixture obtained was washed with 20% thiosulfate solution and brine, dried over sodium sulfate and solvent was evaporated. The evaporation residue obtained was subjected to chromatography (silica, EtOAc->EtOAC/MeOH=5:1) and 2.4 g of the Example 17, Step A products was obtained in the form of a yellow solid.

¹H NMR (200MHz, DMSO-d₆, δ, ppm, characteristic signals): 1.20-2.20 (m, 8H), 1.80 (s, 3H), 3.60-4.50 (m, 1H), 7.85 (m, 1H). TLC: CyH/EtOAc=1:3, Rf=0.25.

B. N-(1,2,3,5,6,6a)-Hexahydro-pentalen-1-yl)-acetamide and N-(1,2,3,3a, 6,6a)-Hexahydro-pentalen-1-yl)-acetamide

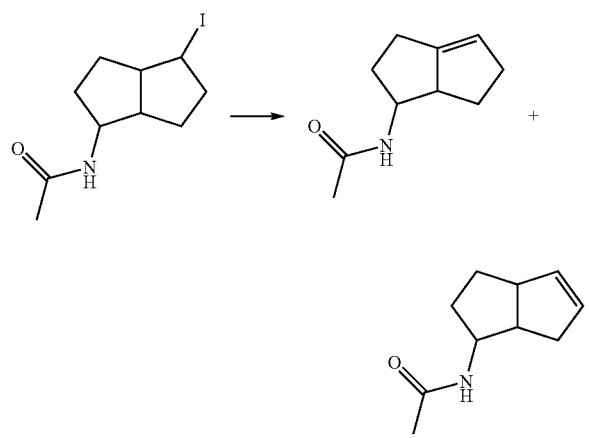

To a solution of 5.6 g of Example 17, Step A products in 50 ml of THF was added 2.14 g of potassium tert-butoxide and the resulting mixture was stirred at rt for 3 days. The mixture obtained was charged with EtOAc and washed with brine/water. The phases obtained were separated and the organic phase obtained was dried over sodium sulfate and solvent was evaporated to dryness. 4.3 g of crude Example 17, Step B products in the form of a yellow oil was obtained.

¹H NMR (200MHz, DMSO-d₆, δ, ppm, characteristic signals): 1.00-2.30 (m, 6H), 1.80 (s, 3H), 2.70 (m, 1H), 2.96 (m, 1H), 3.50 (m, 1H), 5.30 (m, 2H), 7.50, 7.90 (2d, 1H). TLC: CyH/EtOAc=1:3, Rf=0.3.

C. Thiobenzoic acid S-(Acetylamino-hydroxy-octahydropentalenyl)ester

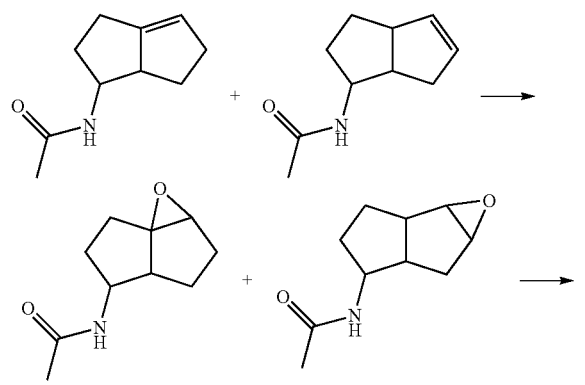

-continued

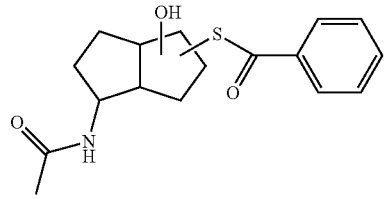

To a solution of 2 g of Example 17, Step B products in 50 ml of DCM was added 2.98 g of mCPBA (70%) and the resulting mixture was stirred at rt overnight. The mixture obtained was diluted with DCM, the mixture obtained was washed with 20% sodium thiosulfate solution, saturated NaHCO₃ solution and brine, dried over sodium sulfate and solvent was evaporated. The crude epoxides were obtained in the evaporation residue. The evaporation residue obtained was taken up in dry toluene and to the mixture obtained 2.85 mL of thiobenzoic acid and 107 mg of Bu₄NCl were added. The resulting mixture was stirred at rt overnight. Upon completion of the reaction, the mixture obtained was stirred for 30 min with aqueous saturated NaHCO₃ solution, the phases were separated and the aqueous layer obtained was extracted with EtOAc. The combined organic layers obtained were dried over sodium sulfate and filtered. The filtrate obtained was concentrated and the concentrate obtained was subjected to chromatography (silica, EtOAC/MeOH=20:1). 372 mg of the early eluting and 400 mg of the late eluting Example 17, Step C products were obtained in the form of solids.

Early eluting: ¹H-NMR (200 MHz, DMSO-d₆, δ, ppm, characteristic signals): 1.20-2.00 (m, 8H), 1.80 (s, 3H), 4.27 (m, 1H), 5.29 (d, 1H, J=4Hz), 7.40-8.10 (m, 6H). TLC: CyH/EtOAc=1:5, Rf=0.3.

Late eluting: ¹H-NMR (200 MHz, DMSO-d₆, δ, ppm, characteristic signals): 1.20-2.10 (m, 8H), 1.80 (s, 3H), 3.50-4.00 (m, 2H), 5.06 (s, 1H), 7.40-8.05 (m, 6H). TLC: TLC: CyH/EtOAc=1:5, Rf=0.2.

D. 14-O-{[4-Acetylamino-6a-hydroxy-octahydro-pentalen-1-ylsulfanyl]-acetyl}-mutilin

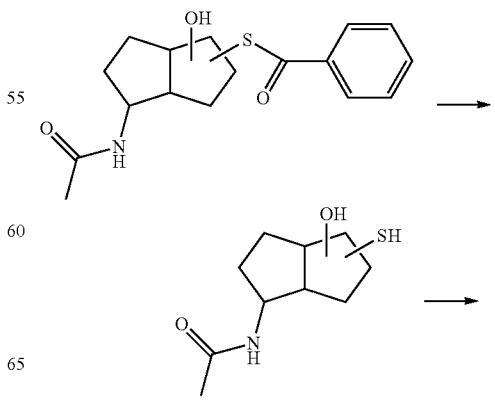

-continued

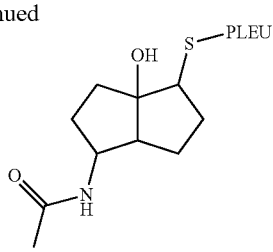

To a solution of 400 mg of Example 17, Step C late eluting products in 3 mL of dry DCM was added at 0° C. 20 mg of DTT and 88 µL of hydrazine monohydrate and the solution obtained was stirred for 5 h at rt. To the mixture obtained further 20 mg of DTT and 88 µL of hydrazine monohydrate were added and the mixture obtained was stirred for 5 h. To the mixture obtained 1 M $H_3PO_4$ was added and the mixture obtained was stirred for 30 min, diluted with DCM and the layers obtained were separated. The organic layer obtained was washed with brine, dried over magnesium sulfate and solvent was evaporated. To the evaporation residue obtained was added 3 mL of MTBE, 1.5 mL of 1 M NaOH, 15 mg of $BnBu_3NCl$ and 450 mg of pleuromutilin tosylate. The resulting mixture was stirred at rt overnight and the mixture obtained was diluted with EtOAc. The organic phase was separated, washed with 1 M NaOH, 0.1 M $H_3PO_4$, saturated $NaHCO_3$ solution and brine, dried over magnesium sulfate and solvent was evaporated. The evaporation residue obtained was subjected to chromatography (silica, CyH/EtOAc=3:1-EtOAc/MeOH/$NH_4OH$=500:25:1). 35 mg of the Example 17 title compounds was obtained in the form of a white solid.

$^1$H-NMR (200 MHz, DMSO-$d_6$, δ, ppm, characteristic signals): 0.63 (d, 3H, J=5Hz), 0.83 (d, 3H, J=6Hz), 1.06 (s, 3H), 1.36 (s, 3H), 1.77 (s, 3H), 2.41 (bs, 1H), 4.55 (d, 1H, J=6Hz), 4.85-5.17 (m, 3H), 5.55 (d, 1H, J=7Hz), 6.16 (dd, 1H, J=12 and 18Hz), 7.65, 7.90 (bd, 1H). MS-ESI+ (m/z): 598 (M+Na). TLC: EtOAc, Rf=0.45.

The invention claimed is:

1. A compound selected from the group consisting of N-unsubstituted, N-alkylated, and N-acylated
    14-O-[(amino($C_{0-4}$)alkyl-hydroxy-cyclobutylsulfanyl)-acetyl]-mutilins,
    14-O-[(amino($C_{0-4}$)alkyl-hydroxy-cyclopentylsulfanyl)-acetyl]-mutilins,
    14-O-[(amino($C_{0-4}$)alkyl-hydroxy-cycloheptylsulfanyl)-acetyl]-mutilins,
    14-O-[(amino($C_{0-4}$)alkyl-hydroxy-cyclooctylsulfanyl)-acetyl]-mutilins, and
    14-O-[(amino($C_{0-4}$)alkyl-hydroxy-bicycloalkylsulfanyl)-acetyl]-mutilins,
    wherein bicycloalkyl is a group of formula

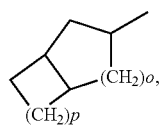

wherein o is 0, 1, 2, 3, or 4, and p is 0, 1, 2, 3, or 4.

2. A compound according to claim 1 which is an N-unsubstituted, N-alkylated, or N-acylated 14-O-[amino($C_{0-4}$)alkyl-hydroxy-cyclopentylsulfanyl)-acetyl]-mutilin or an N-unsubstituted, N-alkylated, or N-acylated 14-O-[amino($C_{0-4}$)alkyl-hydroxy-bicycloalkylsulfanyl)-acetyl]-mutilin,
    wherein one ring of the bicyclic alkyl is a cyclopentyl ring.

3. A compound of formula (I)

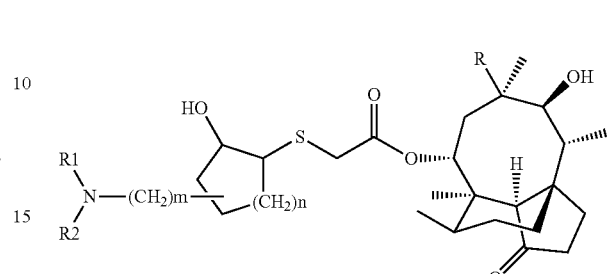

or of formula (II)

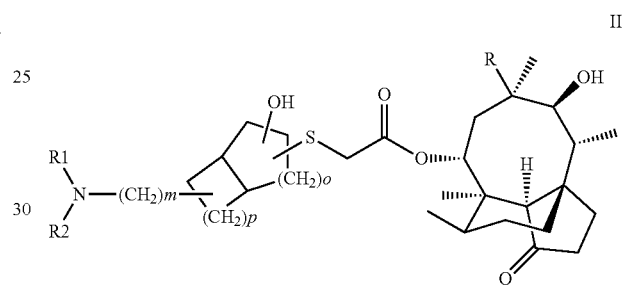

wherein m is 0, 1, 2, 3 or 4;

n is 0, 1, 3 or 4;

o is 0, 1, 2, 3 or 4;

p is 0, 1, 2, 3 or 4;

R is ethyl or vinyl;

$R_1$ is hydrogen or ($C_{1-6}$)alkyl;

$R_2$ is hydrogen, ($C_{3-6}$)cycloalkyl, unsubstituted ($C_{1-6}$) alkyl, or ($C_{1-6}$)alkyl substituted by one or more of hydroxy, methoxy, halogen, or ($C_{3-6}$)cycloalkyl, or $R_1$ and $R_2$ together with the nitrogen atom to which they are attached form a 5 to 7 membered heterocyclic ring containing at least 1 nitrogen atom or 1 nitrogen and 1 additional heteroatom, or $R_2$ is a group of formula

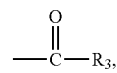

wherein $R_3$ is hydrogen, straight chain or branched ($C_{1-8}$)alkyl or ($C_{3-8}$)cycloalkyl, or $R_3$ is that part of a natural amino acid in D or in L form which remains if the carboxylic acid group is split off, or $R_3$ is that part of a non natural amino acid in D or in L form which remains if the carboxylic acid group is split off.

4. A compound according to claim 3 of formula (III)

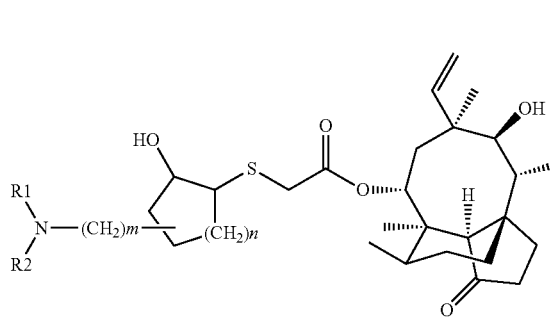

or of formula (IV)

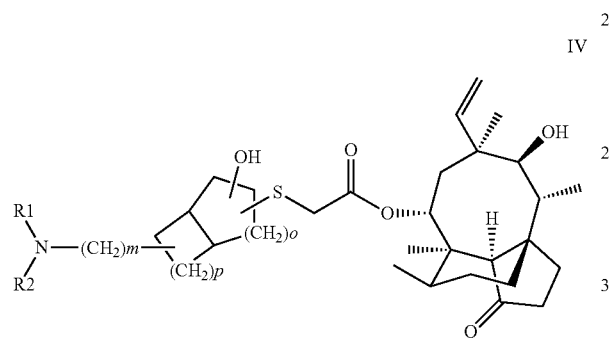

wherein m, n, o, p, R₁ and R₂ are as defined in claim 3.

5. A compound according to claim 3 of formula (V)

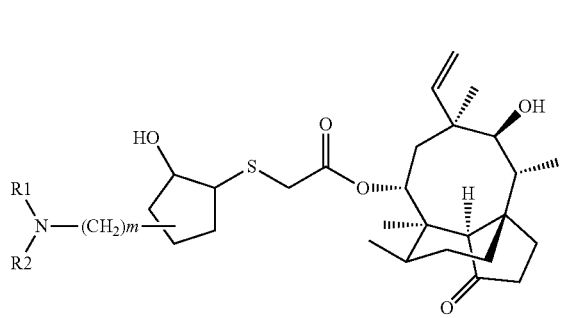

or of formula (VI)

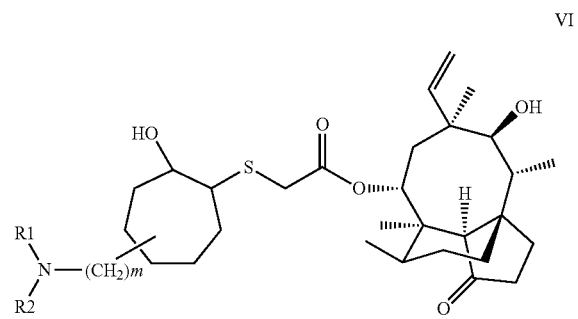

or of formula (VII)

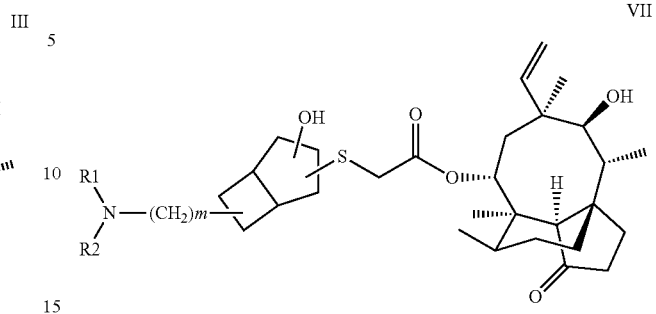

or of formula (VIII)

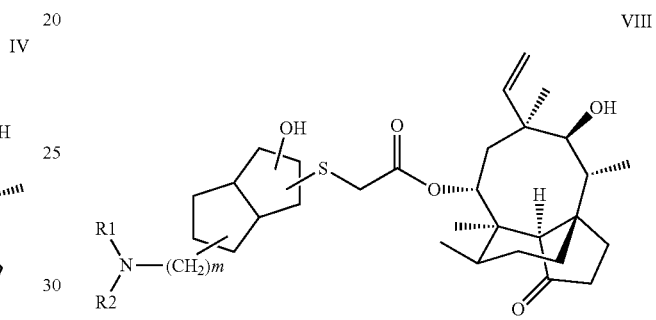

wherein m, R₁ and R₂ are as defined in claim 3.

6. A compound according to claim 1, selected from the group consisting of 14-O-{[(1R, 2R, 4R)-4-Amino-2-hydroxy-cyclopentyl-sulfanyl]-acetyl}-mutilin and the (1S, 2S, 4S) diastereomer thereof, 14-O-{[(1R, 2R, 4S)-4-Amino-2-hydroxy-cyclopentylsulfanyl]-acetyl}-mutilin and the (1S, 2S, 4R) diastereomer thereof, 14-O-{[(1R, 2R, 4R)-4-Aminomethyl-2-hydroxy-cyclopentylsulfanyl]-acetyl}-mutilin and the (1S, 2S, 4S) diastereomer thereof, 14-O-{[(1R, 2R, 4S)-4-Aminomethyl-2-hydroxy-cyclopentylsulfanyl]-acetyl}-mutilin and the (1S, 2S, 4R) diastereomer thereof, 14-O-{[(1R, 2R, 4S)-4-[(2,2-Dimethyl-propylamino)-methyl]-2-hydroxy-cyclopentylsulfanyl]-acetyl}-mutilin and the (1S, 2S, 4R) diastereomer thereof, 14-O-{[(1R, 2R, 4S)-2-Hydroxy-4-[(2,2,2-trifluoro-acetylamino)-methyl]-cyclopentylsulfanyl]-acetyl}-mutilin and the (1S, 2S, 4R) diastereomer thereof, 14-O-{[(1R, 2R, 3S)-2-Hydroxy 3-[2-(2,2,2-trifluoro-acetylamino)-ethyl]-cyclopentylsulfanyl]-acetyl}-mutilin and the (1S, 2S, 3R) diastereomer thereof, 14-O-{[(1R, 2R, 3S)-3-(2-Amino-ethyl)-2-hydroxy-cyclopentylsulfanyl]-acetyl}-mutilin and the (1S, 2S, 3R) diastereomer thereof, 14-O-{[(1R, 2R, 5R)-5-Hydroxy-2-[2-(2,2,2-trifluoro-acetylamino)-ethyl]-cyclopentylsulfanyl]-acetyl}-mutilin and the (1S, 2S, 5S) diastereomer thereof, 14-O-{[(1R, 2R, 5R)-2-(2-Amino-ethyl)-5-hydroxy-cyclopentylsulfanyl]-acetyl}-mutilin and the (1S, 2S, 5S) diastereomer thereof, 14-O-{[(1R, 2R, 5R)-2-[2-(2,2-Dimethyl-propylamino)-ethyl]-5-hydroxy-cyclopentylsulfanyl]-acetyl}-mutilin and the (1S, 2S, 5S) diastereomer thereof, 14-O-{[(1R, 2R, 5R)-5-Amino-2-hydroxy-cycloheptyl-sulfanyl]-acetyl}-mutilin and the (1S, 2S, 5S), (1R, 2R, 5S)-(1S, 2S, 5R) diastereomers thereof, 14-O-{[(1R, 2S, 3S, 5R, 6S)-6-Amino-2-hydroxy-bicyclo[3.2.0]hept-3-ylsulfanyl]-acetyl}-mutilin and the (1S, 2R, 3R, 5S, 6R) diastereomer thereof, 14-O-{[(1R, 2S, 3S, 5R, 6S)-6-Formylamino-2-hydroxy-bicyclo[3.2.0]hept-3-ylsulfanyl]-acetyl}-mutilin and the (1S, 2R, 3R, 5S, 6R) diastereomer thereof, 14-O-{[(1R, 2S, 3S, 5R, 6S)-6-(2-Amino-acetylamino)-2-hydroxy-bicyclo[3.2.0]hept-3-ylsulfanyl]-acetyl}-mutilin and the (1S, 2R, 3R, 5S, 6R) diastereomer thereof, 14-O-{[(1R, 2S, 3S, 5R, 6S)-6-Cyclopropylamino-2-hydroxy-bicyclo[3.2.0]hept-3-ylsulfanyl]-acetyl}-mutilin and the (1S, 2R, 3R, 5S, 6R) diastereomer thereof, and 14-O-{[4-Acetylamino-6a-hydroxy-octahydropentalen-1-ylsulfanyl]-acetyl}-mutilin.

7. A compound according to claim 1 in the form of a salt and/or solvate.

8. A pharmaceutical drug composition comprising a compound of claim 1, in association with at least one pharmaceutical excipient.

9. A pharmaceutical drug composition according to claim 8, further comprising another pharmaceutically active agent.

10. A compound according to claim 3, wherein $R_2$ is $(C_{1-6})$alkyl substituted by one hydroxy.

11. A compound according to claim 3, wherein $R_2$ is $(C_{1-6})$alkyl substituted by two hydroxy.

12. A compound according to claim 3, wherein $R_1$ and $R_2$ together with the nitrogen atom to which they are attached form a 5 to 7 membered heterocyclic ring containing 1 nitrogen and 1 additional heteroatom selected from the group consisting of nitrogen and oxygen.

* * * * *